US012606838B2

(12) United States Patent
Luo et al.

(10) Patent No.: US 12,606,838 B2
(45) Date of Patent: Apr. 21, 2026

(54) COMPOSITIONS AND METHODS FOR ENHANCED PROTEIN PRODUCTION IN FILAMENTOUS FUNGAL CELLS

(71) Applicant: DANISCO US INC., Palo Alto, CA (US)

(72) Inventors: Yun Luo, Palo Alto, CA (US); Igor Nikolaev, Oegstgeest (NL); Robert James Pratt, II, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 603 days.

(21) Appl. No.: 17/919,435

(22) PCT Filed: Apr. 9, 2021

(86) PCT No.: PCT/US2021/026551
§ 371 (c)(1),
(2) Date: Oct. 17, 2022

(87) PCT Pub. No.: WO2021/216302
PCT Pub. Date: Oct. 28, 2021

(65) Prior Publication Data
US 2023/0174998 A1 Jun. 8, 2023

Related U.S. Application Data

(60) Provisional application No. 63/013,741, filed on Apr. 22, 2020.

(51) Int. Cl.
*C12N 15/80* (2006.01)
*C07K 14/37* (2006.01)
*C12N 1/14* (2006.01)
*C12N 9/42* (2006.01)
*C12R 1/885* (2006.01)

(52) U.S. Cl.
CPC .............. *C12N 15/80* (2013.01); *C07K 14/37* (2013.01); *C12N 1/14* (2013.01); *C12N 9/2437* (2013.01); *C12R 2001/885* (2021.05)

(58) Field of Classification Search
None
See application file for complete search history.

(56) References Cited

U.S. PATENT DOCUMENTS 10,876,103 B2 * 12/2020 Ward ...................... C07K 14/37
2019/0309276 A1 * 10/2019 Ward ...................... C12P 21/02

FOREIGN PATENT DOCUMENTS

WO WO-2018067599 A1 * 4/2018 .............. C12P 21/02

OTHER PUBLICATIONS

Witkowski et al (Biochemistry 38:11643-11650, 1999 (Year: 1999).*
(Continued)

*Primary Examiner* — Jeanine A Goldberg

(57) ABSTRACT

The present disclosure is generally related to mutant and genetically modified filamentous fungal cells and methods thereof for use in the production of proteins of interest. More particularly, as described herein, the mutant and/or modified fungal cells (strains) of the disclosure are well-suited for use in industrial scale fermentation processes for the enhanced expression/production of proteins of interest in the absence and/or in the presence of an inducing substrate.

5 Claims, 21 Drawing Sheets

Specification includes a Sequence Listing.

(56) References Cited

OTHER PUBLICATIONS

Seffernick et al., (Bacteriol. 183(8): 2405-2410, 2001) (Year: 2001).*

Chen et al., "Engineering of Trichoderma reesei for enhanced degradation of lignocellulosic biomass by truncation of the cellulase activator ACE3", Biotechnol Biofuels 13:62, 2020.

Hakkinen et al., "Screening of candidate regulators for cellulase and hemicellulase production in Trichoderma reesei and identification of a factor essential for cellulase production", Biotechnol Biofuels 7, 14, 2014.

Zhang et al., "The transcription factor ACE3 controls cellulase activities and lactose metabolism via two additional regulators in the fungus Trichoderma reesei", J. Biol. Chem., 294(48):18435-18450, 2019.

International Search Report and Written Opinion from PCT App. No. PCT/US2021/026551 dated Aug. 6, 2021, 14 pages.

* cited by examiner

```
                    1           10          20          30          40          50          60
                    |           |           |           |           |           |           |
Ace3-S             ------------------------------------------------------------------------
Ace3-L             ---------------------------------------------------------MGSAAPAQGSVAAAA
Ace3-LC            ---------------------------------------------------------MGSAAPAQGSVAAAA

Ace3-S             ------------------MLRYSPVLHLDTLSLPPLTNALP-------------------------------------
Ace3-L             GGPPAAGAGAGAGAVHALTTSPESASASQPGSPTASTTPPQNSLVSAATSFHHHPRGRLVSR
Ace3-LC            GGPPAAGAGAGAGAVHALTTSPESASASQPGSPTASTTPPQNSLVSAATSFHHHPRGRLVSR

Ace3-S             ------RPKCEYLSAVDSCTHCRDAHVQCTFDLPLARRGPKARKKSDQPGQPPPDPSS
Ace3-L             ACDRCRRRKAKCEYLSAVDSCTHCRDAHVQCTFDLPLARRGPKARKKSDQPGQPPPDPSS
Ace3-LC            ACDRCRRRKAKCEYLSAVDSCTHCRDAHVQCTFDLPLARRGPKARKKSDQPGQPPPDPSS

Ace3-S             LSTAARPGQMPPPLTFSGPAVAALQPFASSSLSPDAAWEPVEPLSIDNGLPRQPLGDLPG
Ace3-L             LSTAARPGQMPPPLTFSGPAVAALQPFASSSLSPDAAWEPVEPLSIDNGLPRQPLGDLPG
Ace3-LC            LSTAARPGQMPPPLTFSGPAVAALQPFASSSLSPDAAWEPVEPLSIDNGLPRQPLGDLPG

Ace3-S             LSTIQNISTRQRWIHLANAMTLRNTTLERVSKRCIDLFFDYLYPLTPLVYEPALRDVLAY
Ace3-L             LSTIQNISTRQRWIHLANAMTLRNTTLERVSKRCIDLFFDYLYPLTPLVYEPALRDVLAY
Ace3-LC            LSTIQNISTRQRWIHLANAMTLRNTTLERVSKRCIDLFFDYLYPLTPLVYEPALRDVLAY

Ace3-S             IFSQPLPGVNQPSPLSQLTPDPTTGTTPLNAAESWAGFGQPSGSRTVGSRLAPWADSTFT
Ace3-L             IFSQPLPGVNQPSPLSQLTPDPTTGTTPLNAAESWAGFGQPSGSRTVGSRLAPWADSTFT
Ace3-LC            IFSQPLPGVNQPSPLSQLTPDPTTGTTPLNAAESWAGFGQPSGSRTVGSRLAPWADSTFT

Ace3-S             LVTAVCAEAAFMLPKDIFPEGESVSEILLEASRDCLHQHLEADLENPTANSIAIRYFHSN
Ace3-L             LVTAVCAEAAFMLPKDIFPEGESVSEILLEASRDCLHQHLEADLENPTANSIAIRYFHSN
Ace3-LC            LVTAVCAEAAFMLPKDIFPEGESVSEILLEASRDCLHQHLEADLENPTANSIAIRYFHSN

Ace3-S             CLHAAGKPKYSWHIFGEAIRLAQVMQLHEEAALEGLVPIEAEFRRRCFWILYLGDKSAAI
Ace3-L             CLHAAGKPKYSWHIFGEAIRLAQVMQLHEEAALEGLVPIEAEFRRRCFWILYLGDKSAAI
Ace3-LC            CLHAAGKPKYSWHIFGEAIRLAQVMQLHEEAALEGLVPIEAEFRRRCFWILYLGDKSAAI
```

FIG. 1A

```
Ace3-S   LNNRPITIHKYCFDAGITTLYPSGIEDEFLSTASEPPRKSFISGFNANVRLWQSAADLLL
Ace3-L   LNNRPITIHKYCFDAGITTLYPSGIEDEFLSTASEPPRKSFISGFNANVRLWQSAADLLL
Ace3-LC  LNNRPITIHKYCFDAGITTLYPSGIEDEFLSTASEPPRKSFISGFNANVRLWQSAADLLL

Ace3-S   EIRVLQDQMMQHFRGTMPPNHVLPSADRQHLDSLYVRFITCLDDLPPYLQSCTLAMAAMA
Ace3-L   EIRVLQDQMMQHFRGTMPPNHVLPSADRQHLDSLYVRFITCLDDLPPYLQSCTLAMAAMA
Ace3-LC  EIRVLQDQMMQHFRGTMPPNHVLPSADRQHLDSLYVRFITCLDDLPPYLQSCTLAMAAMA

Ace3-S   EGNGSAESKQYVIQCINLQVTFHCLRMVITQKFEDLSYFAPGVEQADLRKSEIVRDMLRV
Ace3-L   EGNGSAESKQYVIQCINLQVTFHCLRMVITQKFEDLSYFAPGVEQADLRKSEIVRDMLRV
Ace3-LC  EGNGSAESKQYVIQCINLQVTFHCLRMVITQKFEDLSYFAPGVEQADLRKSEIVRDMLRV

Ace3-S   MNEAPFWGLQANGEPNVEKIRLIGASLLAIIHRNQDSPLATRARSDFSVLLDILTRLDSK
Ace3-L   MNEAPFWGLQANGEPNVEKIRLIGASLLAIIHRNQDSPLATRARSDFSVLLDILTRLDSK
Ace3-LC  MNEAPFWGLQANGEPNVEKIRLIGASLLAIIHRNQDSPLATRARSDFSVLLDILTRLDSK

Ace3-S   ASDQLRNTSTTVVG   (SID NO:4)
Ace3-L   ASD-----------   (SID NO:6)
Ace3-LC  ASDQLRNTSTTVVG   (SID NO:2)
```

FIG. 1B

Wild-Type Ace3-LC (SEQ ID NO: 2)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT RLDSKASDQL RNTSTTVVG  (689)
```

Ace3 C-term-5 (SEQ ID NO: 7)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT RLDSKASDQL RNTS  (684)
```

Ace3 C-term-6 (SEQ ID NO: 8)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT RLDSKASDQL RNT  (683)
```

FIG. 2A

Ace3 C-term-7 (SEQ ID NO: 9)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT RLDSKASDQL RN
```

(682)

Ace3 C-term-8 (SEQ ID NO:10)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT RLDSKASDQL R
```

(681)

Ace3 C-term-9 (SEQ ID NO:11)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT RLDSKASDQL L
```

Ace3 C-term-10 (SEQ ID NO:12)

```
MGSAAPAQGS  VAAAAGGPPA  AGAGAGAVHA  LTTSPESASA  SQPGSPTAST  TPPQNSLVSA  ATSFHHHPRG  RLVSRACDRC  RRRKAKCEYL  SAVDSCTHCR
DAHVQCTFDL  PLARRGPKAR  KKSDQPGQPP  PDPSSLSTAA  RPGQMPPPIT  FSGPAVAALQ  PFASSSLSPD  AAWEPVEPLS  IDNGLPRQPL  GDLPGLSTIQ
NISTRQRWIH  LANAMTLRNT  TLERVSKRCI  DLFFDYLYPL  TPLVYEPALR  DVLAYIFSQP  LPGVNQPSPL  SQLTPDPTTG  TTPLNAAESW  AGFGQPSGSR
TVGSRLAPWA  DSTFTLVTAV  CAEAAFMLPK  DIFPEGESVS  EILLEASRDC  LHQHLEADLE  NPTANSIAIR  YFHSNCLHAA  GKPKYSWHIF  GEAIRLAQVM
QLHEEAALEG  LVPIEAEFRR  RCFWILYLGD  KSAAILNNRP  ITIHKYCFDA  GITTLYPSGI  EDEFLSTASE  PPRKSFISGF  NANVRLWQSA  ADLLLEIRVL
QDQMMQHFRG  TMPPNHVLPS  ADRQHLDSLY  VRFITCLDDL  PPYLQSCTLA  MAAMAEGNGS  AESKQYVIQC  INLQVTFHCL  RMVITQKFED  LSYFAPGVEQ
ADLRKSEIVR  DMLRVMNEAP  FWGLQANGEP  NVEKIRLIGA  SLLAIIHRNQ  DSPLATRARS  DFSVLLDILT  RLDSKASDQ                   (679)
```

Ace3 C-term-12 (SEQ ID NO:13)

```
MGSAAPAQGS  VAAAAGGPPA  AGAGAGAVHA  LTTSPESASA  SQPGSPTAST  TPPQNSLVSA  ATSFHHHPRG  RLVSRACDRC  RRRKAKCEYL  SAVDSCTHCR
DAHVQCTFDL  PLARRGPKAR  KKSDQPGQPP  PDPSSLSTAA  RPGQMPPPIT  FSGPAVAALQ  PFASSSLSPD  AAWEPVEPLS  IDNGLPRQPL  GDLPGLSTIQ
NISTRQRWIH  LANAMTLRNT  TLERVSKRCI  DLFFDYLYPL  TPLVYEPALR  DVLAYIFSQP  LPGVNQPSPL  SQLTPDPTTG  TTPLNAAESW  AGFGQPSGSR
TVGSRLAPWA  DSTFTLVTAV  CAEAAFMLPK  DIFPEGESVS  EILLEASRDC  LHQHLEADLE  NPTANSIAIR  YFHSNCLHAA  GKPKYSWHIF  GEAIRLAQVM
QLHEEAALEG  LVPIEAEFRR  RCFWILYLGD  KSAAILNNRP  ITIHKYCFDA  GITTLYPSGI  EDEFLSTASE  PPRKSFISGF  NANVRLWQSA  ADLLLEIRVL
QDQMMQHFRG  TMPPNHVLPS  ADRQHLDSLY  VRFITCLDDL  PPYLQSCTLA  MAAMAEGNGS  AESKQYVIQC  INLQVTFHCL  RMVITQKFED  LSYFAPGVEQ
ADLRKSEIVR  DMLRVMNEAP  FWGLQANGEP  NVEKIRLIGA  SLLAIIHRNQ  DSPLATRARS  DFSVLLDILT  RLDSKAS                     (677)
```

Ace3 C-term-13 (SEQ ID NO:14)

```
MGSAAPAQGS  VAAAAGGPPA  AGAGAGAVHA  LTTSPESASA  SQPGSPTAST  TPPQNSLVSA  ATSFHHHPRG  RLVSRACDRC  RRRKAKCEYL  SAVDSCTHCR
DAHVQCTFDL  PLARRGPKAR  KKSDQPGQPP  PDPSSLSTAA  RPGQMPPPIT  FSGPAVAALQ  PFASSSLSPD  AAWEPVEPLS  IDNGLPRQPL  GDLPGLSTIQ
NISTRQRWIH  LANAMTLRNT  TLERVSKRCI  DLFFDYLYPL  TPLVYEPALR  DVLAYIFSQP  LPGVNQPSPL  SQLTPDPTTG  TTPLNAAESW  AGFGQPSGSR
TVGSRLAPWA  DSTFTLVTAV  CAEAAFMLPK  DIFPEGESVS  EILLEASRDC  LHQHLEADLE  NPTANSIAIR  YFHSNCLHAA  GKPKYSWHIF  GEAIRLAQVM
QLHEEAALEG  LVPIEAEFRR  RCFWILYLGD  KSAAILNNRP  ITIHKYCFDA  GITTLYPSGI  EDEFLSTASE  PPRKSFISGF  NANVRLWQSA  ADLLLEIRVL
QDQMMQHFRG  TMPPNHVLPS  ADRQHLDSLY  VRFITCLDDL  PPYLQSCTLA  MAAMAEGNGS  AESKQYVIQC  INLQVTFHCL  RMVITQKFED  LSYFAPGVEQ
ADLRKSEIVR  DMLRVMNEAP  FWGLQANGEP  NVEKIRLIGA  SLLAIIHRNQ  DSPLATRARS  DFSVLLDILT  RLDSKA                      (676)
```

FIG. 2C

Ace3 C-term-14 (SEQ ID NO:15)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT RLDSK                          (675)
```

Ace3 C-term-15 (SEQ ID NO:16)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT RLDS                           (674)
```

Ace3 C-term-16 (SEQ ID NO:17)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT RLD                            (673)
```

FIG. 2D

Ace3 C-term-17 (SEQ ID NO:18)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT RL
                                                                                      (672)
```

Ace3 C-term-18 (SEQ ID NO:19)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT R
                                                                                     (671)
```

Ace3 C-term-19 (SEQ ID NO:20)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLLEIRVL
QDQMMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDILT T
                                                                                     (670)
```

FIG. 2E

Ace3 C-term-20 (SEQ ID NO:21)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLEIRVL
QDQMMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSVLLDIL
                                                                                                    (669)
```

Ace3 C-term-25 (SEQ ID NO:22)

```
MGSAAPAQGS VAAAAGGPPA AGAGAGAVHA LTTSPESASA SQPGSPTAST TPPQNSLVSA ATSFHHHPRG RLVSRACDRC RRRKAKCEYL SAVDSCTHCR
DAHVQCTFDL PLARRGPKAR KKSDQPGQPP PDPSSLSTAA RPGQMPPLT FSGPAVAALQ PFASSSLSPD AAWEPVEPLS IDNGLPRQPL GDLPGLSTIQ
NISTRQRWIH LANAMTLRNT TLERVSKRCI DLFFDYLYPL TPLVYEPALR DVLAYIFSQP LPGVNQPSPL SQLTPDPTTG TTPLNAAESW AGFGQPSGSR
TVGSRLAPWA DSTFTLVTAV CAEAAFMLPK DIFPEGESVS EILLEASRDC LHQHLEADLE NPTANSIAIR YFHSNCLHAA GKPKYSWHIF GEAIRLAQVM
QLHEEAALEG LVPIEAEFRR RCFWILYLGD KSAAILNNRP ITIHKYCFDA GITTLYPSGI EDEFLSTASE PPRKSFISGF NANVRLWQSA ADLLEIRVL
QDQMMQHFRG TMPPNHVLPS ADRQHLDSLY VRFITCLDDL PPYLQSCTLA MAAMAEGNGS AESKQYVIQC INLQVTFHCL RMVITQKFED LSYFAPGVEQ
ADLRKSEIVR DMLRVMNEAP FWGLQANGEP NVEKIRLIGA SLLAIIHRNQ DSPLATRARS DFSV
                                                                                                    (664)
```

FIG. 2F

Ace3 Binuclear Zinc (Zn₂Cys₆) Binding Domain

73-VSRACDRCRRRKAKCEYLSAVDSCTHCRDAHVQCTFD-109

FIG. 3

Ace3-LC Protein Sequence Showing Wild-Type C-Terminus Ending in Glycine (G)

MGSAAPAQGSVAAAAGGPPAAGAGAGAGAVHALTTSPESASASQPGSPTASTTPPQNSLVSAATSFHHHPRGRLVSRACDRCRRRKAKCEY

LSAVDSCTHCRDAHVQCTFDLPLARRGPKARKKSDQPGQPPPDPSSLSTAARPGQMPPPLTFSGPAVAALQPFASSSLSPDAAWEPVEP

LSIDNGLPRQPLGDLPGLSTIQNISTRQRWIHLANAMTLRNTTLERVSKRCIDLFFDYLYPLTPLVYEPALRDVLAYIFSQPLPGVNQP

SPLSQLTPDPTTGTTPLNAAESWAGFGQPSGSRTVGSRLAPWADSTFTLVTAVCAEAAFMLPKDIFPEGESVSEILLEASRDCLHQHLE

ADLENPTANSIAIRYFHSNCLHAAGKPKYSWHIFGEAIRLAQVMQLHEEAALEGLVPIEAEFRRCFWILYLGDKSAAILNNRPITIHK

YCFDAGITTLYPSGIEDEFLSTASEPPRKSFISGFNANVRLWQSAADLLLEIRVLQDQMQHFRGTMPPNHVLPSADRQHLDSLYVRFI

TCLDDLPPYLQSCTLAMAAMAEGNGSAESKQYVIQCINLQVTFHCLRMVITQKFEDLSYFAPGVEQADLRKSEIVRDMLRVMNEAPFWG

LQANGEPNVEKIRLIGASLLAIIHRNQDSPLATRARSDFSVLLDILTRLDSKASDQLRNTSTTVVG  (689)

|       |       |       |       |
-25     -20     -15     -10      -5

FIG. 4

Ace3 Wild-Type C-Terminus Relative to Ace3 C-Termini "C-term-7" and "C-term-17"

Ace3-LC C-terminus    641-SLLAIIHRNQDSPLATRARSDFSVLLDILTRLDSKASDQLRNTSTTVVG-689

Ace3-LC C-term-7      641-SLLAIIHRNQDSPLATRARSDFSVLLDILTRLDSKASDQLRN-682

Ace3-LC C-term-17     641-SLLAIIHRNQDSPLATRARSDFSVLLDILTRL-672

ALIGNMENT OF ACE3 C-TERMINAL VARIANTS

Ace3-LC

641-SLLAIIHRNQDSPLATRARSDFSVLLDILTRLDSKASDQLRNTSTTVVG-689

Ace3-L

641-SLLAIIHRNQDSPLATRARSDFSVLLDILTRLDSKASD-678

Ace3-LC-V5

641-SLLAIIHRNQDSPLATRARSDFSVLLDILTRLDSKASDGKPIPNPLLGLDST-692

Ace3-LC-V5-(6xHis)

641-SLLAIIHRNQDSPLATRARSDFSVLLDILTRLDSKASDGKPIPNPLLGLDSTRTGHHHHHH-701

FIG. 12

Amino Acid Positions 641-689 (SEQ ID NO: 30) of the Wild-Type Ace3-LC C-Terminus

SEQUENCE LISTING

<160> NUMBER OF SEQ ID NOS: 70

<210> SEQ ID NO 1
<211> LENGTH: 2641
<212> TYPE: DNA
<213> ORGANISM: Hypocrea jecorina

<400> SEQUENCE: 1

```
atgggctcag cagctccggc ccagggctct gtagctgcag ctgcaggcgg ccctccagct      60
gctggcgctg gcgctggcgc tgtccacgcc ctcaccacct cgcccgagtc tgcctcggcc     120
tcgcagcccg gctcgccaac cgcctcaacc acgccgccgc agaactcact cgtgtcggct     180
```

-continued

```
gcaacctcgt tccaccacca tcccagaggc cgtctggtga gcagagcctg cgaccgctgc      240
cgccggcgca aggccaaggt cagtctagcc cctttgctgt tgcttgcatc tctgttgtca      300
ttgctcctcc tcctgctgct gctgatgctg ctgctcctcc tcctcctcct cctccccgtc      360
tcctggtccc tggtccctgc tcttcatatg tccttactgc ccgtgtctcc tctccccgtt      420
cccgttcccc ctcctcccgt cctcttctcc tgcgtgtctg tcatgcgtac aaagcataca      480
tacaatacat cagcatacat ggcaagcgtt gtgttgtgtt gagagttgtg tgtattgtat      540
tgcactgcct tcacaactcg ttcatactgc tgcagcctca ccccaacacc gacctcgtct      600
tccatgctgc gctactcccc cgtcttacac ctggatactc tctccttgcc accactgacc      660
aatgctcttc cccgcccaaa gtgcgagtac ctcagcgctg tcgatagctg cacgcactgc      720
cgcgatgccc acgtgcagtg cactttcgac ctgcccctgg cgcgacgcgg ccccaaagcg      780
aggaagaaga gcgaccagcc cggccagccg cctcctgatc cgagctcgct ctccaccgcg      840
gctcgacccg gccagatgcc gccgccgctg accttctccg gccccgcagt agccgcgctg      900
cagcccttcg cctcgtcgtc gctgtcgccc gacgcggcc tgggagcccgt cgagccgctc      960 agcattgaca acggcctgcc ccggcagccg ctgggcgacc tgcccggcct ctccaccatc     1020
cagaacatct cgacgcgcca gcgatggata cacctggcca acgccatgac gctgcgcaac     1080
acgacgctag agcgcgtctc gaagcgatgt atcgacctct tcttcgacta cctctacccc     1140
ctcacccccc tggtgtacga gccggccctc cgggacgtgc tcgcatacat cttctcccag     1200
cccttgcctg gcgtcaacca accatcgccg ctgtcacagc tcacgccaga cccgaccacc     1260
ggcaccaccc ccctcaacgc tgccgagtcg tgggccggct ttggccagcc cagcggctcg     1320
cgaaccgtcg gcagcaggct ggctccctgg gccgactcga ccttcaccct ggtcacggcc     1380
gtctgcgcag aggcagcatt catgctaccc aaggacattt tccccgaagg agaatccgtc     1440
tctgagatct tgctcgaagc ctctcgggac tgcctgcacc agcacctcga ggccgacctg     1500
gagaatccga cggccaactc gattgccatt cgctacttcc actccaactg cctccacgct     1560
gcggggaagc ccaagtactc gtggcacata tttggcgagg ccatccgcct ggcgcaggtc     1620
atgcagctgc acgaggaggc tgccctcgag gggctcgtcc ccatcgaggc agagttccgc     1680
cgtcgctgct tttggatcct gtacttgggc gacaagtcag ccgctatact caacaatcgg     1740
cccatcacca tccacaagta ctgcttcgac gccggcatca ccacgctata cccgtcgggt     1800
atcgaggacg agttcctgag cacggcgtcc gagccgcccc ggaagagctt catatccggc     1860
ttcaacgcaa atgtgcggct ctggcagtcc gcggctgatt tgctgctgga aatccgcgtg     1920
ctgcaagatc agatgatgca gcactttcga gggaccatgc ccccgaacca tgtgctgccc     1980
tccgccgaca ggcagcatct cgattctctc tatgtccgct tcatcacctg cttggacgat     2040
ctcccgccgt acctccagtc gtgcactctg gcgatggcag cgatggcaga aggcaacggg     2100
tctgccgagt ccaagcagta cgtgatacag tgcatcaacc tgcaggtgac gtttcactgt     2160
ctgcgcatgg taattacgca gaaattcgaa gacctctctt attttgctcc tggcgttgag     2220
caggctgatc tcagaaagtc ggagattgtg cgagacatgc tgagggtgat gaacgaggcg     2280
cccttttggg gcctgcaggc caatggcgag ccaaacgtga gtcgtttcct tgtctcttct     2340
cttttctgca cacccttttc ttcgacgacc ccccctctct ctttatatcc ctgcggatat     2400
gtatatcatc aagcctcggc acttgttgct aatctgtcct gattatgttg tctggatgct     2460
gcaggttgaa aagattcgcc ttatcggagc tagtttgctg gccatcatcc atcgcaacca     2520 ggattcacccc ttggctacgc gagccaggag cgactttccc gtgcttttgg atattctcac     2580
```

-continued

```
gcggctggac tcgaaggcgt cggaccaact gaggaatacg tccactaccg ttgttggcta     2640
a                                                                     2641
```

<210> SEQ ID NO 2
<211> LENGTH: 689
<212> TYPE: PRT
<213> ORGANISM: Hypocrea jecorina

<400> SEQUENCE: 2

```
Met Gly Ser Ala Ala Pro Ala Gln Gly Ser Val Ala Ala Ala Ala Gly
1               5                   10                  15

Gly Pro Pro Ala Ala Gly Ala Gly Ala Gly Ala Val His Ala Leu Thr
            20                  25                  30

Thr Ser Pro Glu Ser Ala Ser Ala Ser Gln Pro Gly Ser Pro Thr Ala
        35                  40                  45

Ser Thr Thr Pro Pro Gln Asn Ser Leu Val Ser Ala Ala Thr Ser Phe
    50                  55                  60

His His His Pro Arg Gly Arg Leu Val Ser Arg Ala Cys Asp Arg Cys
65                  70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
            100                 105                 110

Ala Arg Arg Gly Pro Lys Ala Arg Lys Lys Ser Asp Gln Pro Gly Gln
        115                 120                 125

Pro Pro Pro Asp Pro Ser Ser Leu Ser Thr Ala Ala Arg Pro Gly Gln
    130                 135                 140

Met Pro Pro Pro Leu Thr Phe Ser Gly Pro Ala Val Ala Ala Leu Gln
145                 150                 155                 160

Pro Phe Ala Ser Ser Ser Leu Ser Pro Asp Ala Ala Trp Glu Pro Val
                165                 170                 175

Glu Pro Leu Ser Ile Asp Asn Gly Leu Pro Arg Gln Pro Leu Gly Asp
            180                 185                 190

Leu Pro Gly Leu Ser Thr Ile Gln Asn Ile Ser Thr Arg Gln Arg Trp
        195                 200                 205

Ile His Leu Ala Asn Ala Met Thr Leu Arg Asn Thr Thr Leu Glu Arg
    210                 215                 220

Val Ser Lys Arg Cys Ile Asp Leu Phe Phe Asp Tyr Leu Tyr Pro Leu
225                 230                 235                 240

Thr Pro Leu Val Tyr Glu Pro Ala Leu Arg Asp Val Leu Ala Tyr Ile
                245                 250                 255

Phe Ser Gln Pro Leu Pro Gly Val Asn Gln Pro Ser Pro Leu Ser Gln
            260                 265                 270

Leu Thr Pro Asp Pro Thr Thr Gly Thr Thr Pro Leu Asn Ala Ala Glu
        275                 280                 285

Ser Trp Ala Gly Phe Gly Gln Pro Ser Gly Ser Arg Thr Val Gly Ser
    290                 295                 300

Arg Leu Ala Pro Trp Ala Asp Ser Thr Phe Thr Leu Val Thr Ala Val
305                 310                 315                 320

Cys Ala Glu Ala Ala Phe Met Leu Pro Lys Asp Ile Phe Pro Glu Gly
                325                 330                 335

Glu Ser Val Ser Glu Ile Leu Leu Glu Ala Ser Arg Asp Cys Leu His
            340                 345                 350
```

-continued

```
Gln His Leu Glu Ala Asp Leu Glu Asn Pro Thr Ala Asn Ser Ile Ala
        355             360             365

Ile Arg Tyr Phe His Ser Asn Cys Leu His Ala Ala Gly Lys Pro Lys
    370             375             380

Tyr Ser Trp His Ile Phe Gly Glu Ala Ile Arg Leu Ala Gln Val Met
385             390             395             400

Gln Leu His Glu Glu Ala Ala Leu Glu Gly Leu Val Pro Ile Glu Ala
            405             410             415

Glu Phe Arg Arg Arg Cys Phe Trp Ile Leu Tyr Leu Gly Asp Lys Ser
        420             425             430

Ala Ala Ile Leu Asn Asn Arg Pro Ile Thr Ile His Lys Tyr Cys Phe
        435             440             445

Asp Ala Gly Ile Thr Thr Leu Tyr Pro Ser Gly Ile Glu Asp Glu Phe
    450             455             460

Leu Ser Thr Ala Ser Glu Pro Pro Arg Lys Ser Phe Ile Ser Gly Phe
465             470             475             480

Asn Ala Asn Val Arg Leu Trp Gln Ser Ala Ala Asp Leu Leu Leu Glu
            485             490             495

Ile Arg Val Leu Gln Asp Gln Met Met Gln His Phe Arg Gly Thr Met
        500             505             510

Pro Pro Asn His Val Leu Pro Ser Ala Asp Arg Gln His Leu Asp Ser
        515             520             525

Leu Tyr Val Arg Phe Ile Thr Cys Leu Asp Asp Leu Pro Pro Tyr Leu
    530             535             540

Gln Ser Cys Thr Leu Ala Met Ala Ala Met Ala Glu Gly Asn Gly Ser
545             550             555             560

Ala Glu Ser Lys Gln Tyr Val Ile Gln Cys Ile Asn Leu Gln Val Thr
            565             570             575

Phe His Cys Leu Arg Met Val Ile Thr Gln Lys Phe Glu Asp Leu Ser
        580             585             590

Tyr Phe Ala Pro Gly Val Glu Gln Ala Asp Leu Arg Lys Ser Glu Ile
        595             600             605

Val Arg Asp Met Leu Arg Val Met Asn Glu Ala Pro Phe Trp Gly Leu
    610             615             620

Gln Ala Asn Gly Glu Pro Asn Val Glu Lys Ile Arg Leu Ile Gly Ala
625             630             635             640

Ser Leu Leu Ala Ile Ile His Arg Asn Gln Asp Ser Pro Leu Ala Thr
            645             650             655

Arg Ala Arg Ser Asp Phe Ser Val Leu Leu Asp Ile Leu Thr Arg Leu
        660             665             670

Asp Ser Lys Ala Ser Asp Gln Leu Arg Asn Thr Ser Thr Thr Val Val
        675             680             685

Gly
```

<210> SEQ ID NO 3
<211> LENGTH: 2038
<212> TYPE: DNA
<213> ORGANISM: Hypocrea jecorina

<400> SEQUENCE: 3

```
atgctgcgct actcccccgt cttacacctg gatactctct ccttgccacc actgaccaat       60
gctcttcccc gcccaaagtg cgagtacctc agcgctgtcg atagctgcac gcactgccgc      120
gatgcccacg tgcagtgcac tttcgacctg cccctggcgc gacgcggccc caaagcgagg      180
```

-continued

```
aagaagagcg accagcccgg ccagccgcct cctgatccga gctcgctctc caccgcggct     240
cgacccggcc agatgccgcc gccgctgacc ttctccggcc ccgcagtagc cgcgctgcag     300
cccttcgcct cgtcgtcgct gtcgcccgac gcggcctggg agcccgtcga gccgctcagc     360
attgacaacg gcctgccccg gcagccgctg ggcgacctgc ccggcctctc caccatccag     420
aacatctcga cgcgccagcg atggatacac ctggccaacg ccatgacgct gcgcaacacg     480
acgctagagc gcgtctcgaa gcgatgtatc gacctcttct tcgactacct ctacccctc     540 acccccctgg tgtacgagcc ggccctccgg gacgtgctcg catacatctt ctcccagccc     600
ttgcctggcg tcaaccaacc atcgccgctg tcacagctca cgccagaccc gaccaccggc     660
accacccccc tcaacgctgc cgagtcgtgg gccggctttg gccagcccag cggctcgcga     720
accgtcggca gcaggctggc tccctgggcc gactcgacct tcaccctggt cacggccgtc     780
tgcgcagagg cagcattcat gctacccaag gacattttcc ccgaaggaga atccgtctct     840
gagatcttgc tcgaagcctc tcgggactgc ctgcaccagc acctcgaggc cgacctggag     900
aatccgacgg ccaactcgat tgccattcgc tacttccact ccaactgcct ccacgctgcg     960
gggaagccca agtactcgtg gcacatattt ggcgaggcca tccgcctggc gcaggtcatg    1020
cagctgcacg aggaggctgc cctcgagggg ctcgtcccca tcgaggcaga gttccgccgt    1080
cgctgctttt ggatcctgta cttgggcgac aagtcagccg ctatactcaa caatcggccc    1140
atcaccatcc acaagtactg cttcgacgcc ggcatcacca cgctataccc gtcgggtatc    1200
gaggacgagt tcctgagcac ggcgtccgag ccgccccgga agagcttcat atccggcttc    1260
aacgcaaatg tgcggctctg gcagtccgcg gctgatttgc tgctggaaat ccgcgtgctg    1320
caagatcaga tgatgcagca ctttcgaggg accatgcccc cgaaccatgt gctgccctcc    1380
gccgacaggc agcatctcga ttctctctat gtccgcttca tcacctgctt ggacgatctc    1440
ccgccgtacc tccagtcgtg cactctggcg atggcagcga tggcagaagg caacgggtct    1500
gccgagtcca agcagtacgt gatacagtgc atcaacctgc aggtgacgtt tcactgtctg    1560
cgcatggtaa ttacgcagaa attcgaagac ctctcttatt ttgctcctgg cgttgagcag    1620
gctgatctca gaaagtcgga gattgtgcga gacatgctga gggtgatgaa cgaggcgccc    1680
ttttggggcc tgcaggccaa tggcgagcca aacgtgagtc gtttccttgt ctcttctctt    1740
ttctgcacac ccttttcttc gacgacccccc cctctctctt tatatccctg cggatatgta    1800
tatcatcaag cctcggcact tgttgctaat ctgtcctgat tatgttgtct ggatgctgca    1860
ggttgaaaag attcgcctta tcggagctag tttgctggcc atcatccatc gcaaccagga    1920
ttcacccttg gctacgcgag ccaggagcga ctttccgtg cttttggata ttctcacgcg    1980
gctggactcg aaggcgtcgg accaactgag gaatacgtcc actaccgttg ttggctaa     2038
```

<210> SEQ ID NO 4
<211> LENGTH: 651
<212> TYPE: PRT
<213> ORGANISM: Hypocrea jecorina

<400> SEQUENCE: 4

```
Met Leu Arg Tyr Ser Pro Val Leu His Leu Asp Thr Leu Ser Leu Pro
1               5                   10                  15

Pro Leu Thr Asn Ala Leu Pro Arg Pro Lys Cys Glu Tyr Leu Ser Ala
            20                  25                  30

Val Asp Ser Cys Thr His Cys Arg Asp Ala His Val Gln Cys Thr Phe
        35                  40                  45
```

-continued

```
Asp Leu Pro Leu Ala Arg Arg Gly Pro Lys Ala Arg Lys Lys Ser Asp
    50                  55                  60

Gln Pro Gly Gln Pro Pro Pro Asp Pro Ser Ser Leu Ser Thr Ala Ala
65                  70                  75                  80

Arg Pro Gly Gln Met Pro Pro Pro Leu Thr Phe Ser Gly Pro Ala Val
                85                  90                  95

Ala Ala Leu Gln Pro Phe Ala Ser Ser Ser Leu Ser Pro Asp Ala Ala
            100                 105                 110

Trp Glu Pro Val Glu Pro Leu Ser Ile Asp Asn Gly Leu Pro Arg Gln
            115                 120                 125

Pro Leu Gly Asp Leu Pro Gly Leu Ser Thr Ile Gln Asn Ile Ser Thr
    130                 135                 140

Arg Gln Arg Trp Ile His Leu Ala Asn Ala Met Thr Leu Arg Asn Thr
145                 150                 155                 160

Thr Leu Glu Arg Val Ser Lys Arg Cys Ile Asp Leu Phe Phe Asp Tyr
                165                 170                 175

Leu Tyr Pro Leu Thr Pro Leu Val Tyr Glu Pro Ala Leu Arg Asp Val
            180                 185                 190

Leu Ala Tyr Ile Phe Ser Gln Pro Leu Pro Gly Val Asn Gln Pro Ser
            195                 200                 205

Pro Leu Ser Gln Leu Thr Pro Asp Pro Thr Thr Gly Thr Thr Pro Leu
    210                 215                 220

Asn Ala Ala Glu Ser Trp Ala Gly Phe Gly Gln Pro Ser Gly Ser Arg
225                 230                 235                 240

Thr Val Gly Ser Arg Leu Ala Pro Trp Ala Asp Ser Thr Phe Thr Leu
                245                 250                 255

Val Thr Ala Val Cys Ala Glu Ala Ala Phe Met Leu Pro Lys Asp Ile
            260                 265                 270

Phe Pro Glu Gly Glu Ser Val Ser Glu Ile Leu Leu Glu Ala Ser Arg
            275                 280                 285

Asp Cys Leu His Gln His Leu Glu Ala Asp Leu Glu Asn Pro Thr Ala
    290                 295                 300

Asn Ser Ile Ala Ile Arg Tyr Phe His Ser Asn Cys Leu His Ala Ala
305                 310                 315                 320

Gly Lys Pro Lys Tyr Ser Trp His Ile Phe Gly Glu Ala Ile Arg Leu
                325                 330                 335

Ala Gln Val Met Gln Leu His Glu Glu Ala Ala Leu Glu Gly Leu Val
            340                 345                 350

Pro Ile Glu Ala Glu Phe Arg Arg Arg Cys Phe Trp Ile Leu Tyr Leu
            355                 360                 365

Gly Asp Lys Ser Ala Ala Ile Leu Asn Asn Arg Pro Ile Thr Ile His
    370                 375                 380

Lys Tyr Cys Phe Asp Ala Gly Ile Thr Thr Leu Tyr Pro Ser Gly Ile
385                 390                 395                 400

Glu Asp Glu Phe Leu Ser Thr Ala Ser Glu Pro Pro Arg Lys Ser Phe
                405                 410                 415

Ile Ser Gly Phe Asn Ala Asn Val Arg Leu Trp Gln Ser Ala Ala Asp
            420                 425                 430

Leu Leu Leu Glu Ile Arg Val Leu Gln Asp Gln Met Met Gln His Phe
            435                 440                 445

Arg Gly Thr Met Pro Pro Asn His Val Leu Pro Ser Ala Asp Arg Gln
    450                 455                 460

His Leu Asp Ser Leu Tyr Val Arg Phe Ile Thr Cys Leu Asp Asp Leu
```

-continued

```
465               470               475               480

Pro Pro Tyr Leu Gln Ser Cys Thr Leu Ala Met Ala Ala Met Ala Glu
                485               490               495

Gly Asn Gly Ser Ala Glu Ser Lys Gln Tyr Val Ile Gln Cys Ile Asn
            500               505               510

Leu Gln Val Thr Phe His Cys Leu Arg Met Val Ile Thr Gln Lys Phe
            515               520               525

Glu Asp Leu Ser Tyr Phe Ala Pro Gly Val Glu Gln Ala Asp Leu Arg
        530               535               540

Lys Ser Glu Ile Val Arg Asp Met Leu Arg Val Met Asn Glu Ala Pro
545               550               555               560

Phe Trp Gly Leu Gln Ala Asn Gly Glu Pro Asn Val Ser Arg Phe Leu
                565               570               575

Pro Arg His Leu Leu Leu Ile Cys Pro Asp Tyr Val Val Trp Met Leu
            580               585               590

Gln Val Glu Lys Ile Arg Leu Ile Gly Ala Ser Leu Leu Ala Ile Ile
            595               600               605

His Arg Asn Gln Asp Ser Pro Leu Ala Thr Arg Ala Arg Ser Asp Phe
        610               615               620

Ser Val Leu Leu Asp Ile Leu Thr Arg Leu Asp Ser Lys Ala Ser Asp
625               630               635               640

Gln Leu Arg Asn Thr Ser Thr Thr Val Val Gly
                645               650
```

<210> SEQ ID NO 5
<211> LENGTH: 2608
<212> TYPE: DNA
<213> ORGANISM: Hypocrea jecorina

<400> SEQUENCE: 5

```
atgggctcag cagctccggc ccagggctct gtagctgcag ctgcaggcgg ccctccagct      60
gctggcgctg gcgctggcgc tgtccacgcc ctcaccacct cgcccgagtc tgcctcggcc     120
tcgcagcccg gctcgccaac cgcctcaacc acgccgccgc agaactcact cgtgtcggct     180
gcaacctcgt tccaccacca tcccagaggc cgtctggtga gcagagcctg cgaccgctgc     240
cgccggcgca aggccaaggt cagtctagcc cctttgctgt tgcttgcatc tctgttgtca     300
ttgctcctcc tcctgctgct gctgatgctg ctgctcctcc tcctcctcct cctccccgtc     360
tcctggtccc tggtccctgc tcttcatatg tccttactgc ccgtgtctcc tctccccgtt     420
cccgttcccc ctcctcccgt cctcttctcc tgcgtgtctg tcatgcgtac aaagcataca     480
tacaatacat cagcatacat ggcaagcgtt gtgttgtgtt gagagttgtg tgtattgtat     540
tgcactgcct tcacaactcg ttcatactgc tgcagcctca ccccaacacc gacctcgtct     600
tccatgctgc gctactcccc cgtcttacac ctggatactc tctccttgcc accactgacc     660
aatgctcttc cccgcccaaa gtgcgagtac ctcagcgctg tcgatagctg cacgcactgc     720
cgcgatgccc acgtgcagtg cactttcgac ctgcccctgg cgcgacgcgg ccccaaagcg     780
aggaagaaga cgaccagcc cggccagccg cctcctgatc cgagctcgct ctccaccgcg     840
gctcgacccg gccagatgcc gccgccgctg accttctccg ccccgcagt agccgcgctg     900 cagcccttcg cctcgtcgtc gctgtcgccc gacgcggcct gggagcccgt cgagccgctc     960
agcattgaca cggcctgccc cggcagccg ctgggcgacc tgcccggcct ctccaccatc    1020
cagaacatct cgacgcgcca gcgatggata cacctggcca cgccatgac gctgcgcaac    1080
```

-continued

```
acgacgctag agcgcgtctc gaagcgatgt atcgacctct tcttcgacta cctctacccc    1140
ctcacccccc tggtgtacga gccggccctc cgggacgtgc tcgcatacat cttctcccag    1200
cccttgcctg gcgtcaacca accatcgccg ctgtcacagc tcacgccaga cccgaccacc    1260
ggcaccaccc ccctcaacgc tgccgagtcg tgggccggct ttggccagcc cagcggctcg    1320
cgaaccgtcg gcagcaggct ggctccctgg gccgactcga ccttcaccct ggtcacggcc    1380
gtctgcgcag aggcagcatt catgctaccc aaggacattt tccccgaagg agaatccgtc    1440
tctgagatct tgctcgaagc ctctcgggac tgcctgcacc agcacctcga ggccgacctg    1500
gagaatccga cggccaactc gattgccatt cgctacttcc actccaactg cctccacgct    1560
gcggggaagc ccaagtactc gtggcacata tttggcgagg ccatccgcct ggcgcaggtc    1620
atgcagctgc acgaggaggc tgccctcgag gggctcgtcc ccatcgaggc agagttccgc    1680
cgtcgctgct tttggatcct gtacttgggc gacaagtcag ccgctatact caacaatcgg    1740
cccatcacca tccacaagta ctgcttcgac gccggcatca ccacgctata cccgtcgggt    1800
atcgaggacg agttcctgag cacggcgtcc gagccgcccc ggaagagctt catatccggc    1860
ttcaacgcaa atgtgcggct ctggcagtcc gcggctgatt tgctgctgga aatccgcgtg    1920
ctgcaagatc agatgatgca gcactttcga gggaccatgc ccccgaacca tgtgctgccc    1980
tccgccgaca ggcagcatct cgattctctc tatgtccgct tcatcacctg cttggacgat    2040
ctcccgccgt acctccagtc gtgcactctg gcgatggcag cgatggcaga aggcaacggg    2100
tctgccgagt ccaagcagta cgtgatacag tgcatcaacc tgcaggtgac gtttcactgt    2160
ctgcgcatgg taattacgca gaaattcgaa gacctctctt attttgctcc tggcgttgag    2220
caggctgatc tcagaaagtc ggagattgtg cgagacatgc tgagggtgat gaacgaggcg    2280
cccttttggg gcctgcaggc caatggcgag ccaaacgtga gtcgtttcct tgtctcttct    2340
cttttctgca cacccttttc ttcgacgacc cccctctct ctttatatcc ctgcggatat    2400
gtatatcatc aagcctcggc acttgttgct aatctgtcct gattatgttg tctggatgct    2460
gcaggttgaa aagattcgcc ttatcggagc tagtttgctg gccatcatcc atcgcaacca    2520
ggattcaccc ttggctacgc gagccaggag cgacttttcc gtgctttttgg atattctcac    2580 gcggctggac tcgaaggcgt cggactaa                                       2608
```

<210> SEQ ID NO 6
<211> LENGTH: 678
<212> TYPE: PRT
<213> ORGANISM: Hypocrea jecorina

<400> SEQUENCE: 6

```
Met Gly Ser Ala Ala Pro Ala Gln Gly Ser Val Ala Ala Ala Gly
1               5                   10                  15

Gly Pro Pro Ala Ala Gly Ala Gly Ala Gly Ala Val His Ala Leu Thr
            20                  25                  30

Thr Ser Pro Glu Ser Ala Ser Ala Ser Gln Pro Gly Ser Pro Thr Ala
        35                  40                  45

Ser Thr Thr Pro Pro Gln Asn Ser Leu Val Ser Ala Ala Thr Ser Phe
    50                  55                  60

His His His Pro Arg Gly Arg Leu Val Ser Arg Ala Cys Asp Arg Cys
65                  70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
```

-continued

```
                    100             105             110

Ala Arg Arg Gly Pro Lys Ala Arg Lys Lys Ser Asp Gln Pro Gly Gln
            115             120             125

Pro Pro Pro Asp Pro Ser Ser Leu Ser Thr Ala Ala Arg Pro Gly Gln
        130             135             140

Met Pro Pro Pro Leu Thr Phe Ser Gly Pro Ala Val Ala Ala Leu Gln
145             150             155             160

Pro Phe Ala Ser Ser Ser Leu Ser Pro Asp Ala Ala Trp Glu Pro Val
            165             170             175

Glu Pro Leu Ser Ile Asp Asn Gly Leu Pro Arg Gln Pro Leu Gly Asp
            180             185             190

Leu Pro Gly Leu Ser Thr Ile Gln Asn Ile Ser Thr Arg Gln Arg Trp
        195             200             205

Ile His Leu Ala Asn Ala Met Thr Leu Arg Asn Thr Thr Leu Glu Arg
        210             215             220

Val Ser Lys Arg Cys Ile Asp Leu Phe Phe Asp Tyr Leu Tyr Pro Leu
225             230             235             240

Thr Pro Leu Val Tyr Glu Pro Ala Leu Arg Asp Val Leu Ala Tyr Ile
            245             250             255

Phe Ser Gln Pro Leu Pro Gly Val Asn Gln Pro Ser Pro Leu Ser Gln
            260             265             270

Leu Thr Pro Asp Pro Thr Thr Gly Thr Thr Pro Leu Asn Ala Ala Glu
        275             280             285

Ser Trp Ala Gly Phe Gly Gln Pro Ser Gly Ser Arg Thr Val Gly Ser
    290             295             300

Arg Leu Ala Pro Trp Ala Asp Ser Thr Phe Thr Leu Val Thr Ala Val
305             310             315             320

Cys Ala Glu Ala Ala Phe Met Leu Pro Lys Asp Ile Phe Pro Glu Gly
            325             330             335

Glu Ser Val Ser Glu Ile Leu Leu Glu Ala Ser Arg Asp Cys Leu His
            340             345             350

Gln His Leu Glu Ala Asp Leu Glu Asn Pro Thr Ala Asn Ser Ile Ala
        355             360             365

Ile Arg Tyr Phe His Ser Asn Cys Leu His Ala Ala Gly Lys Pro Lys
    370             375             380

Tyr Ser Trp His Ile Phe Gly Glu Ala Ile Arg Leu Ala Gln Val Met
385             390             395             400

Gln Leu His Glu Glu Ala Ala Leu Glu Gly Leu Val Pro Ile Glu Ala
            405             410             415

Glu Phe Arg Arg Arg Cys Phe Trp Ile Leu Tyr Leu Gly Asp Lys Ser
            420             425             430

Ala Ala Ile Leu Asn Asn Arg Pro Ile Thr Ile His Lys Tyr Cys Phe
            435             440             445

Asp Ala Gly Ile Thr Thr Leu Tyr Pro Ser Gly Ile Glu Asp Glu Phe
        450             455             460

Leu Ser Thr Ala Ser Glu Pro Pro Arg Lys Ser Phe Ile Ser Gly Phe
465             470             475             480

Asn Ala Asn Val Arg Leu Trp Gln Ser Ala Ala Asp Leu Leu Leu Glu
            485             490             495

Ile Arg Val Leu Gln Asp Gln Met Met Gln His Phe Arg Gly Thr Met
            500             505             510

Pro Pro Asn His Val Leu Pro Ser Ala Asp Arg Gln His Leu Asp Ser
        515             520             525
```

-continued

```
Leu Tyr Val Arg Phe Ile Thr Cys Leu Asp Asp Leu Pro Pro Tyr Leu
    530                 535                 540

Gln Ser Cys Thr Leu Ala Met Ala Ala Met Ala Glu Gly Asn Gly Ser
545                 550                 555                 560

Ala Glu Ser Lys Gln Tyr Val Ile Gln Cys Ile Asn Leu Gln Val Thr
                565                 570                 575

Phe His Cys Leu Arg Met Val Ile Thr Gln Lys Phe Glu Asp Leu Ser
                580                 585                 590

Tyr Phe Ala Pro Gly Val Glu Gln Ala Asp Leu Arg Lys Ser Glu Ile
            595                 600                 605

Val Arg Asp Met Leu Arg Val Met Asn Glu Ala Pro Phe Trp Gly Leu
        610                 615                 620

Gln Ala Asn Gly Glu Pro Asn Val Glu Lys Ile Arg Leu Ile Gly Ala
625                 630                 635                 640

Ser Leu Leu Ala Ile Ile His Arg Asn Gln Asp Ser Pro Leu Ala Thr
                645                 650                 655

Arg Ala Arg Ser Asp Phe Ser Val Leu Leu Asp Ile Leu Thr Arg Leu
                660                 665                 670

Asp Ser Lys Ala Ser Asp
            675

<210> SEQ ID NO 7
<211> LENGTH: 684
<212> TYPE: PRT
<213> ORGANISM: Hypocrea jecorina

<400> SEQUENCE: 7

Met Gly Ser Ala Ala Pro Ala Gln Gly Ser Val Ala Ala Ala Ala Gly
1               5                   10                  15

Gly Pro Pro Ala Ala Gly Ala Gly Ala Gly Ala Val His Ala Leu Thr
                20                  25                  30

Thr Ser Pro Glu Ser Ala Ser Ala Ser Gln Pro Gly Ser Pro Thr Ala
            35                  40                  45

Ser Thr Thr Pro Pro Gln Asn Ser Leu Val Ser Ala Ala Thr Ser Phe
        50                  55                  60

His His His Pro Arg Gly Arg Leu Val Ser Arg Ala Cys Asp Arg Cys
65                  70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
                100                 105                 110

Ala Arg Arg Gly Pro Lys Ala Arg Lys Lys Ser Asp Gln Pro Gly Gln
            115                 120                 125

Pro Pro Pro Asp Pro Ser Ser Leu Ser Thr Ala Ala Arg Pro Gly Gln
        130                 135                 140

Met Pro Pro Pro Leu Thr Phe Ser Gly Pro Ala Val Ala Ala Leu Gln
145                 150                 155                 160

Pro Phe Ala Ser Ser Ser Leu Ser Pro Asp Ala Ala Trp Glu Pro Val
                165                 170                 175

Glu Pro Leu Ser Ile Asp Asn Gly Leu Pro Arg Gln Pro Leu Gly Asp
                180                 185                 190

Leu Pro Gly Leu Ser Thr Ile Gln Asn Ile Ser Thr Arg Gln Arg Trp
            195                 200                 205

Ile His Leu Ala Asn Ala Met Thr Leu Arg Asn Thr Thr Leu Glu Arg
```

-continued

```
            210              215              220

Val Ser Lys Arg Cys Ile Asp Leu Phe Phe Asp Tyr Leu Tyr Pro Leu
225              230              235              240

Thr Pro Leu Val Tyr Glu Pro Ala Leu Arg Asp Val Leu Ala Tyr Ile
             245              250              255

Phe Ser Gln Pro Leu Pro Gly Val Asn Gln Pro Ser Pro Leu Ser Gln
             260              265              270

Leu Thr Pro Asp Pro Thr Thr Gly Thr Thr Pro Leu Asn Ala Ala Glu
         275              280              285

Ser Trp Ala Gly Phe Gly Gln Pro Ser Gly Ser Arg Thr Val Gly Ser
    290              295              300

Arg Leu Ala Pro Trp Ala Asp Ser Thr Phe Thr Leu Val Thr Ala Val
305              310              315              320

Cys Ala Glu Ala Ala Phe Met Leu Pro Lys Asp Ile Phe Pro Glu Gly
             325              330              335

Glu Ser Val Ser Glu Ile Leu Leu Glu Ala Ser Arg Asp Cys Leu His
             340              345              350

Gln His Leu Glu Ala Asp Leu Glu Asn Pro Thr Ala Asn Ser Ile Ala
        355              360              365

Ile Arg Tyr Phe His Ser Asn Cys Leu His Ala Ala Gly Lys Pro Lys
    370              375              380

Tyr Ser Trp His Ile Phe Gly Glu Ala Ile Arg Leu Ala Gln Val Met
385              390              395              400

Gln Leu His Glu Glu Ala Ala Leu Glu Gly Leu Val Pro Ile Glu Ala
             405              410              415

Glu Phe Arg Arg Arg Cys Phe Trp Ile Leu Tyr Leu Gly Asp Lys Ser
         420              425              430

Ala Ala Ile Leu Asn Asn Arg Pro Ile Thr Ile His Lys Tyr Cys Phe
        435              440              445

Asp Ala Gly Ile Thr Thr Leu Tyr Pro Ser Gly Ile Glu Asp Glu Phe
    450              455              460

Leu Ser Thr Ala Ser Glu Pro Pro Arg Lys Ser Phe Ile Ser Gly Phe
465              470              475              480

Asn Ala Asn Val Arg Leu Trp Gln Ser Ala Ala Asp Leu Leu Leu Glu
             485              490              495

Ile Arg Val Leu Gln Asp Gln Met Met Gln His Phe Arg Gly Thr Met
         500              505              510

Pro Pro Asn His Val Leu Pro Ser Ala Asp Arg Gln His Leu Asp Ser
        515              520              525

Leu Tyr Val Arg Phe Ile Thr Cys Leu Asp Asp Leu Pro Pro Tyr Leu
    530              535              540

Gln Ser Cys Thr Leu Ala Met Ala Ala Met Ala Glu Gly Asn Gly Ser
545              550              555              560

Ala Glu Ser Lys Gln Tyr Val Ile Gln Cys Ile Asn Leu Gln Val Thr
             565              570              575

Phe His Cys Leu Arg Met Val Ile Thr Gln Lys Phe Glu Asp Leu Ser
         580              585              590

Tyr Phe Ala Pro Gly Val Glu Gln Ala Asp Leu Arg Lys Ser Glu Ile
        595              600              605

Val Arg Asp Met Leu Arg Val Met Asn Glu Ala Pro Phe Trp Gly Leu
    610              615              620

Gln Ala Asn Gly Glu Pro Asn Val Glu Lys Ile Arg Leu Ile Gly Ala
625              630              635              640
```

-continued

Ser Leu Leu Ala Ile Ile His Arg Asn Gln Asp Ser Pro Leu Ala Thr
            645             650             655

Arg Ala Arg Ser Asp Phe Ser Val Leu Leu Asp Ile Leu Thr Arg Leu
            660             665             670

Asp Ser Lys Ala Ser Asp Gln Leu Arg Asn Thr Ser
        675             680

<210> SEQ ID NO 8
<211> LENGTH: 683
<212> TYPE: PRT
<213> ORGANISM: Hypocrea jecorina

<400> SEQUENCE: 8

Met Gly Ser Ala Ala Pro Ala Gln Gly Ser Val Ala Ala Ala Ala Gly
1               5               10              15

Gly Pro Pro Ala Ala Gly Ala Gly Ala Gly Ala Val His Ala Leu Thr
            20              25              30

Thr Ser Pro Glu Ser Ala Ser Ala Ser Gln Pro Gly Ser Pro Thr Ala
        35              40              45

Ser Thr Thr Pro Pro Gln Asn Ser Leu Val Ser Ala Ala Thr Ser Phe
        50              55              60

His His His Pro Arg Gly Arg Leu Val Ser Arg Ala Cys Asp Arg Cys
65              70              75              80

Arg Arg Arg Lys Ala Lys Cys Glu Tyr Leu Ser Ala Val Asp Ser Cys
            85              90              95

Thr His Cys Arg Asp Ala His Val Gln Cys Thr Phe Asp Leu Pro Leu
            100             105             110

Ala Arg Arg Gly Pro Lys Ala Arg Lys Lys Ser Asp Gln Pro Gly Gln
            115             120             125

Pro Pro Pro Asp Pro Ser Ser Leu Ser Thr Ala Ala Arg Pro Gly Gln
        130             135             140

Met Pro Pro Pro Leu Thr Phe Ser Gly Pro Ala Val Ala Ala Leu Gln
145             150             155             160

Pro Phe Ala Ser Ser Ser Leu Ser Pro Asp Ala Ala Trp Glu Pro Val
            165             170             175

Glu Pro Leu Ser Ile Asp Asn Gly Leu Pro Arg Gln Pro Leu Gly Asp
            180             185             190

Leu Pro Gly Leu Ser Thr Ile Gln Asn Ile Ser Thr Arg Gln Arg Trp
            195             200             205

Ile His Leu Ala Asn Ala Met Thr Leu Arg Asn Thr Thr Leu Glu Arg
        210             215             220

Val Ser Lys Arg Cys Ile Asp Leu Phe Phe Asp Tyr Leu Tyr Pro Leu
225             230             235             240

Thr Pro Leu Val Tyr Glu Pro Ala Leu Arg Asp Val Leu Ala Tyr Ile
            245             250             255

Phe Ser Gln Pro Leu Pro Gly Val Asn Gln Pro Ser Pro Leu Ser Gln
            260             265             270

Leu Thr Pro Asp Pro Thr Thr Gly Thr Thr Pro Leu Asn Ala Ala Glu
            275             280             285

Ser Trp Ala Gly Phe Gly Gln Pro Ser Gly Ser Arg Thr Val Gly Ser
        290             295             300

Arg Leu Ala Pro Trp Ala Asp Ser Thr Phe Thr Leu Val Thr Ala Val
305             310             315             320

Cys Ala Glu Ala Ala Phe Met Leu Pro Lys Asp Ile Phe Pro Glu Gly

-continued

```
                325                   330                   335

Glu Ser Val Ser Glu Ile Leu Leu Glu Ala Ser Arg Asp Cys Leu His
            340                   345                   350

Gln His Leu Glu Ala Asp Leu Glu Asn Pro Thr Ala Asn Ser Ile Ala
            355                   360                   365

Ile Arg Tyr Phe His Ser Asn Cys Leu His Ala Ala Gly Lys Pro Lys
            370                   375                   380

Tyr Ser Trp His Ile Phe Gly Glu Ala Ile Arg Leu Ala Gln Val Met
385                   390                   395                   400

Gln Leu His Glu Glu Ala Ala Leu Glu Gly Leu Val Pro Ile Glu Ala
                405                   410                   415

Glu Phe Arg Arg Arg Cys Phe Trp Ile Leu Tyr Leu Gly Asp Lys Ser
            420                   425                   430

Ala Ala Ile Leu Asn Asn Arg Pro Ile Thr Ile His Lys Tyr Cys Phe
            435                   440                   445

Asp Ala Gly Ile Thr Thr Leu Tyr Pro Ser Gly Ile Glu Asp Glu Phe
            450                   455                   460

Leu Ser Thr Ala Ser Glu Pro Pro Arg Lys Ser Phe Ile Ser Gly Phe
465                   470                   475                   480

Asn Ala Asn Val Arg Leu Trp Gln Ser Ala Ala Asp Leu Leu Leu Glu
                485                   490                   495

Ile Arg Val Leu Gln Asp Gln Met Met Gln His Phe Arg Gly Thr Met
            500                   505                   510

Pro Pro Asn His Val Leu Pro Ser Ala Asp Arg Gln His Leu Asp Ser
            515                   520                   525

Leu Tyr Val Arg Phe Ile Thr Cys Leu Asp Asp Leu Pro Pro Tyr Leu
            530                   535                   540

Gln Ser Cys Thr Leu Ala Met Ala Ala Met Ala Glu Gly Asn Gly Ser
545                   550                   555                   560

Ala Glu Ser Lys Gln Tyr Val Ile Gln Cys Ile Asn Leu Gln Val Thr
                565                   570                   575

Phe His Cys Leu Arg Met Val Ile Thr Gln Lys Phe Glu Asp Leu Ser
            580                   585                   590

Tyr Phe Ala Pro Gly Val Glu Gln Ala Asp Leu Arg Lys Ser Glu Ile
            595                   600                   605

Val Arg Asp Met Leu Arg Val Met Asn Glu Ala Pro Phe Trp Gly Leu
            610                   615                   620

Gln Ala Asn Gly Glu Pro Asn Val Glu Lys Ile Arg Leu Ile Gly Ala
625                   630                   635                   640

Ser Leu Leu Ala Ile Ile His Arg Asn Gln Asp Ser Pro Leu Ala Thr
                645                   650                   655

Arg Ala Arg Ser Asp Phe Ser Val Leu Leu Asp Ile Leu Thr Arg Leu
            660                   665                   670

Asp Ser Lys Ala Ser Asp Gln Leu Arg Asn Thr
            675                   680

<210> SEQ ID NO 9
<211> LENGTH: 682
<212> TYPE: PRT
<213> ORGANISM: Hypocrea jecorina

<400> SEQUENCE: 9

Met Gly Ser Ala Ala Pro Ala Gln Gly Ser Val Ala Ala Ala Ala Gly
1               5                   10                  15
```

-continued

```
Gly Pro Pro Ala Ala Gly Ala Gly Ala Gly Ala Val His Ala Leu Thr
            20              25              30

Thr Ser Pro Glu Ser Ala Ser Ala Ser Gln Pro Gly Ser Pro Thr Ala
            35              40              45

Ser Thr Thr Pro Pro Gln Asn Ser Leu Val Ser Ala Ala Thr Ser Phe
        50              55              60

His His His Pro Arg Gly Arg Leu Val Ser Arg Ala Cys Asp Arg Cys
65              70              75              80

Arg Arg Arg Lys Ala Lys Cys Glu Tyr Leu Ser Ala Val Asp Ser Cys
            85              90              95

Thr His Cys Arg Asp Ala His Val Gln Cys Thr Phe Asp Leu Pro Leu
            100             105             110

Ala Arg Arg Gly Pro Lys Ala Arg Lys Lys Ser Asp Gln Pro Gly Gln
            115             120             125

Pro Pro Pro Asp Pro Ser Ser Leu Ser Thr Ala Ala Arg Pro Gly Gln
        130             135             140

Met Pro Pro Pro Leu Thr Phe Ser Gly Pro Ala Val Ala Ala Leu Gln
145             150             155             160

Pro Phe Ala Ser Ser Ser Leu Ser Pro Asp Ala Ala Trp Glu Pro Val
            165             170             175

Glu Pro Leu Ser Ile Asp Asn Gly Leu Pro Arg Gln Pro Leu Gly Asp
            180             185             190

Leu Pro Gly Leu Ser Thr Ile Gln Asn Ile Ser Thr Arg Gln Arg Trp
            195             200             205

Ile His Leu Ala Asn Ala Met Thr Leu Arg Asn Thr Thr Leu Glu Arg
        210             215             220

Val Ser Lys Arg Cys Ile Asp Leu Phe Phe Asp Tyr Leu Tyr Pro Leu
225             230             235             240

Thr Pro Leu Val Tyr Glu Pro Ala Leu Arg Asp Val Leu Ala Tyr Ile
            245             250             255

Phe Ser Gln Pro Leu Pro Gly Val Asn Gln Pro Ser Pro Leu Ser Gln
            260             265             270

Leu Thr Pro Asp Pro Thr Thr Gly Thr Thr Pro Leu Asn Ala Ala Glu
            275             280             285

Ser Trp Ala Gly Phe Gly Gln Pro Ser Gly Ser Arg Thr Val Gly Ser
        290             295             300

Arg Leu Ala Pro Trp Ala Asp Ser Thr Phe Thr Leu Val Thr Ala Val
305             310             315             320

Cys Ala Glu Ala Ala Phe Met Leu Pro Lys Asp Ile Phe Pro Glu Gly
            325             330             335

Glu Ser Val Ser Glu Ile Leu Leu Glu Ala Ser Arg Asp Cys Leu His
            340             345             350

Gln His Leu Glu Ala Asp Leu Glu Asn Pro Thr Ala Asn Ser Ile Ala
            355             360             365

Ile Arg Tyr Phe His Ser Asn Cys Leu His Ala Ala Gly Lys Pro Lys
        370             375             380

Tyr Ser Trp His Ile Phe Gly Glu Ala Ile Arg Leu Ala Gln Val Met
385             390             395             400

Gln Leu His Glu Glu Ala Ala Leu Glu Gly Leu Val Pro Ile Glu Ala
            405             410             415

Glu Phe Arg Arg Arg Cys Phe Trp Ile Leu Tyr Leu Gly Asp Lys Ser
            420             425             430

Ala Ala Ile Leu Asn Asn Arg Pro Ile Thr Ile His Lys Tyr Cys Phe
```

-continued

```
              435                440                445

Asp Ala Gly Ile Thr Thr Leu Tyr Pro Ser Gly Ile Glu Asp Glu Phe
    450                455                460

Leu Ser Thr Ala Ser Glu Pro Pro Arg Lys Ser Phe Ile Ser Gly Phe
465                470                475                480

Asn Ala Asn Val Arg Leu Trp Gln Ser Ala Ala Asp Leu Leu Leu Glu
                485                490                495

Ile Arg Val Leu Gln Asp Gln Met Met Gln His Phe Arg Gly Thr Met
            500                505                510

Pro Pro Asn His Val Leu Pro Ser Ala Asp Arg Gln His Leu Asp Ser
            515                520                525

Leu Tyr Val Arg Phe Ile Thr Cys Leu Asp Asp Leu Pro Pro Tyr Leu
    530                535                540

Gln Ser Cys Thr Leu Ala Met Ala Ala Met Ala Glu Gly Asn Gly Ser
545                550                555                560

Ala Glu Ser Lys Gln Tyr Val Ile Gln Cys Ile Asn Leu Gln Val Thr
                565                570                575

Phe His Cys Leu Arg Met Val Ile Thr Gln Lys Phe Glu Asp Leu Ser
            580                585                590

Tyr Phe Ala Pro Gly Val Glu Gln Ala Asp Leu Arg Lys Ser Glu Ile
            595                600                605

Val Arg Asp Met Leu Arg Val Met Asn Glu Ala Pro Phe Trp Gly Leu
    610                615                620

Gln Ala Asn Gly Glu Pro Asn Val Glu Lys Ile Arg Leu Ile Gly Ala
625                630                635                640

Ser Leu Leu Ala Ile Ile His Arg Asn Gln Asp Ser Pro Leu Ala Thr
                645                650                655

Arg Ala Arg Ser Asp Phe Ser Val Leu Leu Asp Ile Leu Thr Arg Leu
            660                665                670

Asp Ser Lys Ala Ser Asp Gln Leu Arg Asn
            675                680

<210> SEQ ID NO 10
<211> LENGTH: 681
<212> TYPE: PRT
<213> ORGANISM: Hypocrea jecorina

<400> SEQUENCE: 10

Met Gly Ser Ala Ala Pro Ala Gln Gly Ser Val Ala Ala Ala Gly
1               5                10                15

Gly Pro Pro Ala Ala Gly Ala Gly Ala Gly Ala Val His Ala Leu Thr
            20                25                30

Thr Ser Pro Glu Ser Ala Ser Ala Ser Gln Pro Gly Ser Pro Thr Ala
            35                40                45

Ser Thr Thr Pro Pro Gln Asn Ser Leu Val Ser Ala Ala Thr Ser Phe
    50                55                60

His His His Pro Arg Gly Arg Leu Val Ser Arg Ala Cys Asp Arg Cys
65                70                75                80

Arg Arg Arg Lys Ala Lys Cys Glu Tyr Leu Ser Ala Val Asp Ser Cys
                85                90                95

Thr His Cys Arg Asp Ala His Val Gln Cys Thr Phe Asp Leu Pro Leu
            100                105                110

Ala Arg Arg Gly Pro Lys Ala Arg Lys Lys Ser Asp Gln Pro Gly Gln
            115                120                125
```

-continued

```
Pro Pro Pro Asp Pro Ser Ser Leu Ser Thr Ala Ala Arg Pro Gly Gln
    130             135             140

Met Pro Pro Pro Leu Thr Phe Ser Gly Pro Ala Val Ala Ala Leu Gln
145             150             155             160

Pro Phe Ala Ser Ser Ser Leu Ser Pro Asp Ala Ala Trp Glu Pro Val
                165             170             175

Glu Pro Leu Ser Ile Asp Asn Gly Leu Pro Arg Gln Pro Leu Gly Asp
            180             185             190

Leu Pro Gly Leu Ser Thr Ile Gln Asn Ile Ser Thr Arg Gln Arg Trp
        195             200             205

Ile His Leu Ala Asn Ala Met Thr Leu Arg Asn Thr Thr Leu Glu Arg
    210             215             220

Val Ser Lys Arg Cys Ile Asp Leu Phe Phe Asp Tyr Leu Tyr Pro Leu
225             230             235             240

Thr Pro Leu Val Tyr Glu Pro Ala Leu Arg Asp Val Leu Ala Tyr Ile
            245             250             255

Phe Ser Gln Pro Leu Pro Gly Val Asn Gln Pro Ser Pro Leu Ser Gln
        260             265             270

Leu Thr Pro Asp Pro Thr Thr Gly Thr Thr Pro Leu Asn Ala Ala Glu
        275             280             285

Ser Trp Ala Gly Phe Gly Gln Pro Ser Gly Ser Arg Thr Val Gly Ser
    290             295             300

Arg Leu Ala Pro Trp Ala Asp Ser Thr Phe Thr Leu Val Thr Ala Val
305             310             315             320

Cys Ala Glu Ala Ala Phe Met Leu Pro Lys Asp Ile Phe Pro Glu Gly
            325             330             335

Glu Ser Val Ser Glu Ile Leu Leu Glu Ala Ser Arg Asp Cys Leu His
            340             345             350

Gln His Leu Glu Ala Asp Leu Glu Asn Pro Thr Ala Asn Ser Ile Ala
        355             360             365

Ile Arg Tyr Phe His Ser Asn Cys Leu His Ala Ala Gly Lys Pro Lys
    370             375             380

Tyr Ser Trp His Ile Phe Gly Glu Ala Ile Arg Leu Ala Gln Val Met
385             390             395             400

Gln Leu His Glu Glu Ala Ala Leu Glu Gly Leu Val Pro Ile Glu Ala
            405             410             415

Glu Phe Arg Arg Arg Cys Phe Trp Ile Leu Tyr Leu Gly Asp Lys Ser
        420             425             430

Ala Ala Ile Leu Asn Asn Arg Pro Ile Thr Ile His Lys Tyr Cys Phe
        435             440             445

Asp Ala Gly Ile Thr Thr Leu Tyr Pro Ser Gly Ile Glu Asp Glu Phe
    450             455             460

Leu Ser Thr Ala Ser Glu Pro Pro Arg Lys Ser Phe Ile Ser Gly Phe
465             470             475             480

Asn Ala Asn Val Arg Leu Trp Gln Ser Ala Ala Asp Leu Leu Leu Glu
            485             490             495

Ile Arg Val Leu Gln Asp Gln Met Met Gln His Phe Arg Gly Thr Met
            500             505             510

Pro Pro Asn His Val Leu Pro Ser Ala Asp Arg Gln His Leu Asp Ser
        515             520             525

Leu Tyr Val Arg Phe Ile Thr Cys Leu Asp Asp Leu Pro Pro Tyr Leu
    530             535             540

Gln Ser Cys Thr Leu Ala Met Ala Ala Met Ala Glu Gly Asn Gly Ser
```

-continued

```
545                 550                 555                 560

Ala Glu Ser Lys Gln Tyr Val Ile Gln Cys Ile Asn Leu Gln Val Thr
                565                 570                 575

Phe His Cys Leu Arg Met Val Ile Thr Gln Lys Phe Glu Asp Leu Ser
            580                 585                 590

Tyr Phe Ala Pro Gly Val Glu Gln Ala Asp Leu Arg Lys Ser Glu Ile
            595                 600                 605

Val Arg Asp Met Leu Arg Val Met Asn Glu Ala Pro Phe Trp Gly Leu
        610                 615                 620

Gln Ala Asn Gly Glu Pro Asn Val Glu Lys Ile Arg Leu Ile Gly Ala
625                 630                 635                 640

Ser Leu Leu Ala Ile Ile His Arg Asn Gln Asp Ser Pro Leu Ala Thr
                645                 650                 655

Arg Ala Arg Ser Asp Phe Ser Val Leu Leu Asp Ile Leu Thr Arg Leu
            660                 665                 670

Asp Ser Lys Ala Ser Asp Gln Leu Arg
            675                 680

<210> SEQ ID NO 11
<211> LENGTH: 680
<212> TYPE: PRT
<213> ORGANISM: Hypocrea jecorina

<400> SEQUENCE: 11

Met Gly Ser Ala Ala Pro Ala Gln Gly Ser Val Ala Ala Ala Ala Gly
1               5                   10                  15

Gly Pro Pro Ala Ala Gly Ala Gly Ala Gly Ala Val His Ala Leu Thr
            20                  25                  30

Thr Ser Pro Glu Ser Ala Ser Ala Ser Gln Pro Gly Ser Pro Thr Ala
            35                  40                  45

Ser Thr Thr Pro Pro Gln Asn Ser Leu Val Ser Ala Ala Thr Ser Phe
        50                  55                  60

His His His Pro Arg Gly Arg Leu Val Ser Arg Ala Cys Asp Arg Cys
65                  70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
            100                 105                 110

Ala Arg Arg Gly Pro Lys Ala Arg Lys Lys Ser Asp Gln Pro Gly Gln
            115                 120                 125

Pro Pro Pro Asp Pro Ser Ser Leu Ser Thr Ala Ala Arg Pro Gly Gln
        130                 135                 140

Met Pro Pro Pro Leu Thr Phe Ser Gly Pro Ala Val Ala Ala Leu Gln
145                 150                 155                 160

Pro Phe Ala Ser Ser Ser Leu Ser Pro Asp Ala Ala Trp Glu Pro Val
                165                 170                 175

Glu Pro Leu Ser Ile Asp Asn Gly Leu Pro Arg Gln Pro Leu Gly Asp
            180                 185                 190

Leu Pro Gly Leu Ser Thr Ile Gln Asn Ile Ser Thr Arg Gln Arg Trp
            195                 200                 205

Ile His Leu Ala Asn Ala Met Thr Leu Arg Asn Thr Thr Leu Glu Arg
        210                 215                 220

Val Ser Lys Arg Cys Ile Asp Leu Phe Phe Asp Tyr Leu Tyr Pro Leu
225                 230                 235                 240
```

```
Thr Pro Leu Val Tyr Glu Pro Ala Leu Arg Asp Val Leu Ala Tyr Ile
            245             250             255

Phe Ser Gln Pro Leu Pro Gly Val Asn Gln Pro Ser Pro Leu Ser Gln
        260             265             270

Leu Thr Pro Asp Pro Thr Thr Gly Thr Thr Pro Leu Asn Ala Ala Glu
        275             280             285

Ser Trp Ala Gly Phe Gly Gln Pro Ser Gly Ser Arg Thr Val Gly Ser
    290             295             300

Arg Leu Ala Pro Trp Ala Asp Ser Thr Phe Thr Leu Val Thr Ala Val
305             310             315             320

Cys Ala Glu Ala Ala Phe Met Leu Pro Lys Asp Ile Phe Pro Glu Gly
            325             330             335

Glu Ser Val Ser Glu Ile Leu Leu Glu Ala Ser Arg Asp Cys Leu His
            340             345             350

Gln His Leu Glu Ala Asp Leu Glu Asn Pro Thr Ala Asn Ser Ile Ala
        355             360             365

Ile Arg Tyr Phe His Ser Asn Cys Leu His Ala Ala Gly Lys Pro Lys
    370             375             380

Tyr Ser Trp His Ile Phe Gly Glu Ala Ile Arg Leu Ala Gln Val Met
385             390             395             400

Gln Leu His Glu Glu Ala Ala Leu Glu Gly Leu Val Pro Ile Glu Ala
            405             410             415

Glu Phe Arg Arg Arg Cys Phe Trp Ile Leu Tyr Leu Gly Asp Lys Ser
            420             425             430

Ala Ala Ile Leu Asn Asn Arg Pro Ile Thr Ile His Lys Tyr Cys Phe
            435             440             445

Asp Ala Gly Ile Thr Thr Leu Tyr Pro Ser Gly Ile Glu Asp Glu Phe
    450             455             460

Leu Ser Thr Ala Ser Glu Pro Pro Arg Lys Ser Phe Ile Ser Gly Phe
465             470             475             480

Asn Ala Asn Val Arg Leu Trp Gln Ser Ala Ala Asp Leu Leu Leu Glu
            485             490             495

Ile Arg Val Leu Gln Asp Gln Met Met Gln His Phe Arg Gly Thr Met
            500             505             510

Pro Pro Asn His Val Leu Pro Ser Ala Asp Arg Gln His Leu Asp Ser
            515             520             525

Leu Tyr Val Arg Phe Ile Thr Cys Leu Asp Asp Leu Pro Pro Tyr Leu
        530             535             540

Gln Ser Cys Thr Leu Ala Met Ala Ala Met Ala Glu Gly Asn Gly Ser
545             550             555             560

Ala Glu Ser Lys Gln Tyr Val Ile Gln Cys Ile Asn Leu Gln Val Thr
            565             570             575

Phe His Cys Leu Arg Met Val Ile Thr Gln Lys Phe Glu Asp Leu Ser
            580             585             590

Tyr Phe Ala Pro Gly Val Glu Gln Ala Asp Leu Arg Lys Ser Glu Ile
        595             600             605

Val Arg Asp Met Leu Arg Val Met Asn Glu Ala Pro Phe Trp Gly Leu
    610             615             620

Gln Ala Asn Gly Glu Pro Asn Val Glu Lys Ile Arg Leu Ile Gly Ala
625             630             635             640

Ser Leu Leu Ala Ile Ile His Arg Asn Gln Asp Ser Pro Leu Ala Thr
            645             650             655

Arg Ala Arg Ser Asp Phe Ser Val Leu Leu Asp Ile Leu Thr Arg Leu
```

-continued

```
              660              665              670
Asp Ser Lys Ala Ser Asp Gln Leu
        675              680

<210> SEQ ID NO 12
<211> LENGTH: 679
<212> TYPE: PRT
<213> ORGANISM: Hypocrea jecorina

<400> SEQUENCE: 12

Met Gly Ser Ala Ala Pro Ala Gln Gly Ser Val Ala Ala Ala Gly
1               5               10              15

Gly Pro Pro Ala Ala Gly Ala Gly Ala Gly Ala Val His Ala Leu Thr
        20              25              30

Thr Ser Pro Glu Ser Ala Ser Ala Ser Gln Pro Gly Ser Pro Thr Ala
        35              40              45

Ser Thr Thr Pro Pro Gln Asn Ser Leu Val Ser Ala Ala Thr Ser Phe
        50              55              60

His His His Pro Arg Gly Arg Leu Val Ser Arg Ala Cys Asp Arg Cys
65              70              75              80

Arg Arg Arg Lys Ala Lys Cys Glu Tyr Leu Ser Ala Val Asp Ser Cys
                85              90              95

Thr His Cys Arg Asp Ala His Val Gln Cys Thr Phe Asp Leu Pro Leu
                100             105             110

Ala Arg Arg Gly Pro Lys Ala Arg Lys Lys Ser Asp Gln Pro Gly Gln
        115             120             125

Pro Pro Pro Asp Pro Ser Ser Leu Ser Thr Ala Ala Arg Pro Gly Gln
        130             135             140

Met Pro Pro Pro Leu Thr Phe Ser Gly Pro Ala Val Ala Ala Leu Gln
145             150             155             160

Pro Phe Ala Ser Ser Ser Leu Ser Pro Asp Ala Ala Trp Glu Pro Val
                165             170             175

Glu Pro Leu Ser Ile Asp Asn Gly Leu Pro Arg Gln Pro Leu Gly Asp
                180             185             190

Leu Pro Gly Leu Ser Thr Ile Gln Asn Ile Ser Thr Arg Gln Arg Trp
        195             200             205

Ile His Leu Ala Asn Ala Met Thr Leu Arg Asn Thr Thr Leu Glu Arg
        210             215             220

Val Ser Lys Arg Cys Ile Asp Leu Phe Phe Asp Tyr Leu Tyr Pro Leu
225             230             235             240

Thr Pro Leu Val Tyr Glu Pro Ala Leu Arg Asp Val Leu Ala Tyr Ile
                245             250             255

Phe Ser Gln Pro Leu Pro Gly Val Asn Gln Pro Ser Pro Leu Ser Gln
        260             265             270

Leu Thr Pro Asp Pro Thr Thr Gly Thr Thr Pro Leu Asn Ala Ala Glu
        275             280             285

Ser Trp Ala Gly Phe Gly Gln Pro Ser Gly Ser Arg Thr Val Gly Ser
        290             295             300

Arg Leu Ala Pro Trp Ala Asp Ser Thr Phe Thr Leu Val Thr Ala Val
305             310             315             320

Cys Ala Glu Ala Ala Phe Met Leu Pro Lys Asp Ile Phe Pro Glu Gly
                325             330             335

Glu Ser Val Ser Glu Ile Leu Leu Glu Ala Ser Arg Asp Cys Leu His
        340             345             350
```

-continued

```
Gln His Leu Glu Ala Asp Leu Glu Asn Pro Thr Ala Asn Ser Ile Ala
        355                 360                 365

Ile Arg Tyr Phe His Ser Asn Cys Leu His Ala Ala Gly Lys Pro Lys
        370                 375                 380

Tyr Ser Trp His Ile Phe Gly Glu Ala Ile Arg Leu Ala Gln Val Met
385                 390                 395                 400

Gln Leu His Glu Glu Ala Ala Leu Glu Gly Leu Val Pro Ile Glu Ala
                405                 410                 415

Glu Phe Arg Arg Arg Cys Phe Trp Ile Leu Tyr Leu Gly Asp Lys Ser
                420                 425                 430

Ala Ala Ile Leu Asn Asn Arg Pro Ile Thr Ile His Lys Tyr Cys Phe
                435                 440                 445

Asp Ala Gly Ile Thr Thr Leu Tyr Pro Ser Gly Ile Glu Asp Glu Phe
        450                 455                 460

Leu Ser Thr Ala Ser Glu Pro Pro Arg Lys Ser Phe Ile Ser Gly Phe
465                 470                 475                 480

Asn Ala Asn Val Arg Leu Trp Gln Ser Ala Ala Asp Leu Leu Leu Glu
                485                 490                 495

Ile Arg Val Leu Gln Asp Gln Met Met Gln His Phe Arg Gly Thr Met
                500                 505                 510

Pro Pro Asn His Val Leu Pro Ser Ala Asp Arg Gln His Leu Asp Ser
        515                 520                 525

Leu Tyr Val Arg Phe Ile Thr Cys Leu Asp Asp Leu Pro Pro Tyr Leu
        530                 535                 540

Gln Ser Cys Thr Leu Ala Met Ala Ala Met Ala Glu Gly Asn Gly Ser
545                 550                 555                 560

Ala Glu Ser Lys Gln Tyr Val Ile Gln Cys Ile Asn Leu Gln Val Thr
                565                 570                 575

Phe His Cys Leu Arg Met Val Ile Thr Gln Lys Phe Glu Asp Leu Ser
                580                 585                 590

Tyr Phe Ala Pro Gly Val Glu Gln Ala Asp Leu Arg Lys Ser Glu Ile
                595                 600                 605

Val Arg Asp Met Leu Arg Val Met Asn Glu Ala Pro Phe Trp Gly Leu
        610                 615                 620

Gln Ala Asn Gly Glu Pro Asn Val Glu Lys Ile Arg Leu Ile Gly Ala
625                 630                 635                 640

Ser Leu Leu Ala Ile Ile His Arg Asn Gln Asp Ser Pro Leu Ala Thr
                645                 650                 655

Arg Ala Arg Ser Asp Phe Ser Val Leu Leu Asp Ile Leu Thr Arg Leu
                660                 665                 670

Asp Ser Lys Ala Ser Asp Gln
        675

<210> SEQ ID NO 13
<211> LENGTH: 677
<212> TYPE: PRT
<213> ORGANISM: Hypocrea jecorina

<400> SEQUENCE: 13

Met Gly Ser Ala Ala Pro Ala Gln Gly Ser Val Ala Ala Ala Ala Gly
1                 5                   10                  15

Gly Pro Pro Ala Ala Gly Ala Gly Ala Gly Ala Val His Ala Leu Thr
                20                  25                  30

Thr Ser Pro Glu Ser Ala Ser Ala Ser Gln Pro Gly Ser Pro Thr Ala
        35                  40                  45
```

-continued

```
Ser Thr Thr Pro Pro Gln Asn Ser Leu Val Ser Ala Ala Thr Ser Phe
    50                  55                  60

His His His Pro Arg Gly Arg Leu Val Ser Arg Ala Cys Asp Arg Cys
65                  70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
            100                 105                 110

Ala Arg Arg Gly Pro Lys Ala Arg Lys Lys Ser Asp Gln Pro Gly Gln
            115                 120                 125

Pro Pro Pro Asp Pro Ser Ser Leu Ser Thr Ala Ala Arg Pro Gly Gln
    130                 135                 140

Met Pro Pro Pro Leu Thr Phe Ser Gly Pro Ala Val Ala Ala Leu Gln
145                 150                 155                 160

Pro Phe Ala Ser Ser Ser Leu Ser Pro Asp Ala Ala Trp Glu Pro Val
            165                 170                 175

Glu Pro Leu Ser Ile Asp Asn Gly Leu Pro Arg Gln Pro Leu Gly Asp
            180                 185                 190

Leu Pro Gly Leu Ser Thr Ile Gln Asn Ile Ser Thr Arg Gln Arg Trp
            195                 200                 205

Ile His Leu Ala Asn Ala Met Thr Leu Arg Asn Thr Thr Leu Glu Arg
    210                 215                 220

Val Ser Lys Arg Cys Ile Asp Leu Phe Phe Asp Tyr Leu Tyr Pro Leu
225                 230                 235                 240

Thr Pro Leu Val Tyr Glu Pro Ala Leu Arg Asp Val Leu Ala Tyr Ile
            245                 250                 255

Phe Ser Gln Pro Leu Pro Gly Val Asn Gln Pro Ser Pro Leu Ser Gln
            260                 265                 270

Leu Thr Pro Asp Pro Thr Thr Gly Thr Thr Pro Leu Asn Ala Ala Glu
            275                 280                 285

Ser Trp Ala Gly Phe Gly Gln Pro Ser Gly Ser Arg Thr Val Gly Ser
    290                 295                 300

Arg Leu Ala Pro Trp Ala Asp Ser Thr Phe Thr Leu Val Thr Ala Val
305                 310                 315                 320

Cys Ala Glu Ala Ala Phe Met Leu Pro Lys Asp Ile Phe Pro Glu Gly
            325                 330                 335

Glu Ser Val Ser Glu Ile Leu Leu Glu Ala Ser Arg Asp Cys Leu His
            340                 345                 350

Gln His Leu Glu Ala Asp Leu Glu Asn Pro Thr Ala Asn Ser Ile Ala
            355                 360                 365

Ile Arg Tyr Phe His Ser Asn Cys Leu His Ala Ala Gly Lys Pro Lys
    370                 375                 380

Tyr Ser Trp His Ile Phe Gly Glu Ala Ile Arg Leu Ala Gln Val Met
385                 390                 395                 400

Gln Leu His Glu Glu Ala Ala Leu Glu Gly Leu Val Pro Ile Glu Ala
            405                 410                 415

Glu Phe Arg Arg Arg Cys Phe Trp Ile Leu Tyr Leu Gly Asp Lys Ser
            420                 425                 430

Ala Ala Ile Leu Asn Asn Arg Pro Ile Thr Ile His Lys Tyr Cys Phe
            435                 440                 445

Asp Ala Gly Ile Thr Thr Leu Tyr Pro Ser Gly Ile Glu Asp Glu Phe
    450                 455                 460
```

-continued

```
Leu Ser Thr Ala Ser Glu Pro Pro Arg Lys Ser Phe Ile Ser Gly Phe
465                 470                 475                 480

Asn Ala Asn Val Arg Leu Trp Gln Ser Ala Ala Asp Leu Leu Leu Glu
                485                 490                 495

Ile Arg Val Leu Gln Asp Gln Met Met Gln His Phe Arg Gly Thr Met
            500                 505                 510

Pro Pro Asn His Val Leu Pro Ser Ala Asp Arg Gln His Leu Asp Ser
            515                 520                 525

Leu Tyr Val Arg Phe Ile Thr Cys Leu Asp Asp Leu Pro Pro Tyr Leu
    530                 535                 540

Gln Ser Cys Thr Leu Ala Met Ala Ala Met Ala Glu Gly Asn Gly Ser
545                 550                 555                 560

Ala Glu Ser Lys Gln Tyr Val Ile Gln Cys Ile Asn Leu Gln Val Thr
                565                 570                 575

Phe His Cys Leu Arg Met Val Ile Thr Gln Lys Phe Glu Asp Leu Ser
                580                 585                 590

Tyr Phe Ala Pro Gly Val Glu Gln Ala Asp Leu Arg Lys Ser Glu Ile
                595                 600                 605

Val Arg Asp Met Leu Arg Val Met Asn Glu Ala Pro Phe Trp Gly Leu
    610                 615                 620

Gln Ala Asn Gly Glu Pro Asn Val Glu Lys Ile Arg Leu Ile Gly Ala
625                 630                 635                 640

Ser Leu Leu Ala Ile Ile His Arg Asn Gln Asp Ser Pro Leu Ala Thr
                645                 650                 655

Arg Ala Arg Ser Asp Phe Ser Val Leu Leu Asp Ile Leu Thr Arg Leu
                660                 665                 670

Asp Ser Lys Ala Ser
            675

<210> SEQ ID NO 14
<211> LENGTH: 676
<212> TYPE: PRT
<213> ORGANISM: Hypocrea jecorina

<400> SEQUENCE: 14

Met Gly Ser Ala Ala Pro Ala Gln Gly Ser Val Ala Ala Ala Ala Gly
1               5                   10                  15

Gly Pro Pro Ala Ala Gly Ala Gly Ala Gly Ala Val His Ala Leu Thr
            20                  25                  30

Thr Ser Pro Glu Ser Ala Ser Ala Ser Gln Pro Gly Ser Pro Thr Ala
            35                  40                  45

Ser Thr Thr Pro Pro Gln Asn Ser Leu Val Ser Ala Ala Thr Ser Phe
    50                  55                  60

His His His Pro Arg Gly Arg Leu Val Ser Arg Ala Cys Asp Arg Cys
65                  70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
            100                 105                 110

Ala Arg Arg Gly Pro Lys Ala Arg Lys Lys Ser Asp Gln Pro Gly Gln
            115                 120                 125

Pro Pro Pro Asp Pro Ser Ser Leu Ser Thr Ala Ala Arg Pro Gly Gln
    130                 135                 140

Met Pro Pro Pro Leu Thr Phe Ser Gly Pro Ala Val Ala Ala Leu Gln
145                 150                 155                 160
```

-continued

```
Pro Phe Ala Ser Ser Ser Leu Ser Pro Asp Ala Ala Trp Glu Pro Val
            165             170             175

Glu Pro Leu Ser Ile Asp Asn Gly Leu Pro Arg Gln Pro Leu Gly Asp
            180             185             190

Leu Pro Gly Leu Ser Thr Ile Gln Asn Ile Ser Thr Arg Gln Arg Trp
        195             200             205

Ile His Leu Ala Asn Ala Met Thr Leu Arg Asn Thr Thr Leu Glu Arg
    210             215             220

Val Ser Lys Arg Cys Ile Asp Leu Phe Phe Asp Tyr Leu Tyr Pro Leu
225             230             235             240

Thr Pro Leu Val Tyr Glu Pro Ala Leu Arg Asp Val Leu Ala Tyr Ile
            245             250             255

Phe Ser Gln Pro Leu Pro Gly Val Asn Gln Pro Ser Pro Leu Ser Gln
            260             265             270

Leu Thr Pro Asp Pro Thr Thr Gly Thr Thr Pro Leu Asn Ala Ala Glu
        275             280             285

Ser Trp Ala Gly Phe Gly Gln Pro Ser Gly Ser Arg Thr Val Gly Ser
    290             295             300

Arg Leu Ala Pro Trp Ala Asp Ser Thr Phe Thr Leu Val Thr Ala Val
305             310             315             320

Cys Ala Glu Ala Ala Phe Met Leu Pro Lys Asp Ile Phe Pro Glu Gly
            325             330             335

Glu Ser Val Ser Glu Ile Leu Leu Glu Ala Ser Arg Asp Cys Leu His
        340             345             350

Gln His Leu Glu Ala Asp Leu Glu Asn Pro Thr Ala Asn Ser Ile Ala
        355             360             365

Ile Arg Tyr Phe His Ser Asn Cys Leu His Ala Ala Gly Lys Pro Lys
        370             375             380

Tyr Ser Trp His Ile Phe Gly Glu Ala Ile Arg Leu Ala Gln Val Met
385             390             395             400

Gln Leu His Glu Glu Ala Ala Leu Glu Gly Leu Val Pro Ile Glu Ala
            405             410             415

Glu Phe Arg Arg Arg Cys Phe Trp Ile Leu Tyr Leu Gly Asp Lys Ser
            420             425             430

Ala Ala Ile Leu Asn Asn Arg Pro Ile Thr Ile His Lys Tyr Cys Phe
        435             440             445

Asp Ala Gly Ile Thr Thr Leu Tyr Pro Ser Gly Ile Glu Asp Glu Phe
    450             455             460

Leu Ser Thr Ala Ser Glu Pro Pro Arg Lys Ser Phe Ile Ser Gly Phe
465             470             475             480

Asn Ala Asn Val Arg Leu Trp Gln Ser Ala Ala Asp Leu Leu Leu Glu
            485             490             495

Ile Arg Val Leu Gln Asp Gln Met Met Gln His Phe Arg Gly Thr Met
            500             505             510

Pro Pro Asn His Val Leu Pro Ser Ala Asp Arg Gln His Leu Asp Ser
            515             520             525

Leu Tyr Val Arg Phe Ile Thr Cys Leu Asp Asp Leu Pro Pro Tyr Leu
        530             535             540

Gln Ser Cys Thr Leu Ala Met Ala Ala Met Ala Glu Gly Asn Gly Ser
545             550             555             560

Ala Glu Ser Lys Gln Tyr Val Ile Gln Cys Ile Asn Leu Gln Val Thr
            565             570             575
```

```
Phe His Cys Leu Arg Met Val Ile Thr Gln Lys Phe Glu Asp Leu Ser
            580             585             590

Tyr Phe Ala Pro Gly Val Glu Gln Ala Asp Leu Arg Lys Ser Glu Ile
            595             600             605

Val Arg Asp Met Leu Arg Val Met Asn Glu Ala Pro Phe Trp Gly Leu
            610             615             620

Gln Ala Asn Gly Glu Pro Asn Val Glu Lys Ile Arg Leu Ile Gly Ala
625             630             635             640

Ser Leu Leu Ala Ile Ile His Arg Asn Gln Asp Ser Pro Leu Ala Thr
            645             650             655

Arg Ala Arg Ser Asp Phe Ser Val Leu Leu Asp Ile Leu Thr Arg Leu
            660             665             670

Asp Ser Lys Ala
            675

<210> SEQ ID NO 15
<211> LENGTH: 675
<212> TYPE: PRT
<213> ORGANISM: Hypocrea jecorina

<400> SEQUENCE: 15

Met Gly Ser Ala Ala Pro Ala Gln Gly Ser Val Ala Ala Ala Ala Gly
1               5               10              15

Gly Pro Pro Ala Ala Gly Ala Gly Ala Gly Ala Val His Ala Leu Thr
            20              25              30

Thr Ser Pro Glu Ser Ala Ser Ala Ser Gln Pro Gly Ser Pro Thr Ala
            35              40              45

Ser Thr Thr Pro Pro Gln Asn Ser Leu Val Ser Ala Ala Thr Ser Phe
            50              55              60

His His His Pro Arg Gly Arg Leu Val Ser Arg Ala Cys Asp Arg Cys
65              70              75              80

Arg Arg Arg Lys Ala Lys Cys Glu Tyr Leu Ser Ala Val Asp Ser Cys
                85              90              95

Thr His Cys Arg Asp Ala His Val Gln Cys Thr Phe Asp Leu Pro Leu
            100             105             110

Ala Arg Arg Gly Pro Lys Ala Arg Lys Lys Ser Asp Gln Pro Gly Gln
            115             120             125

Pro Pro Pro Asp Pro Ser Ser Leu Ser Thr Ala Ala Arg Pro Gly Gln
            130             135             140

Met Pro Pro Pro Leu Thr Phe Ser Gly Pro Ala Val Ala Ala Leu Gln
145             150             155             160

Pro Phe Ala Ser Ser Ser Leu Ser Pro Asp Ala Ala Trp Glu Pro Val
            165             170             175

Glu Pro Leu Ser Ile Asp Asn Gly Leu Pro Arg Gln Pro Leu Gly Asp
            180             185             190

Leu Pro Gly Leu Ser Thr Ile Gln Asn Ile Ser Thr Arg Gln Arg Trp
            195             200             205

Ile His Leu Ala Asn Ala Met Thr Leu Arg Asn Thr Thr Leu Glu Arg
            210             215             220

Val Ser Lys Arg Cys Ile Asp Leu Phe Phe Asp Tyr Leu Tyr Pro Leu
225             230             235             240

Thr Pro Leu Val Tyr Glu Pro Ala Leu Arg Asp Val Leu Ala Tyr Ile
            245             250             255

Phe Ser Gln Pro Leu Pro Gly Val Asn Gln Pro Ser Pro Leu Ser Gln
            260             265             270
```

-continued

```
Leu Thr Pro Asp Pro Thr Thr Gly Thr Thr Pro Leu Asn Ala Ala Glu
        275             280             285

Ser Trp Ala Gly Phe Gly Gln Pro Ser Gly Ser Arg Thr Val Gly Ser
    290             295             300

Arg Leu Ala Pro Trp Ala Asp Ser Thr Phe Thr Leu Val Thr Ala Val
305             310             315             320

Cys Ala Glu Ala Ala Phe Met Leu Pro Lys Asp Ile Phe Pro Glu Gly
            325             330             335

Glu Ser Val Ser Glu Ile Leu Leu Glu Ala Ser Arg Asp Cys Leu His
            340             345             350

Gln His Leu Glu Ala Asp Leu Glu Asn Pro Thr Ala Asn Ser Ile Ala
        355             360             365

Ile Arg Tyr Phe His Ser Asn Cys Leu His Ala Ala Gly Lys Pro Lys
    370             375             380

Tyr Ser Trp His Ile Phe Gly Glu Ala Ile Arg Leu Ala Gln Val Met
385             390             395             400

Gln Leu His Glu Glu Ala Ala Leu Glu Gly Leu Val Pro Ile Glu Ala
            405             410             415

Glu Phe Arg Arg Arg Cys Phe Trp Ile Leu Tyr Leu Gly Asp Lys Ser
            420             425             430

Ala Ala Ile Leu Asn Asn Arg Pro Ile Thr Ile His Lys Tyr Cys Phe
            435             440             445

Asp Ala Gly Ile Thr Thr Leu Tyr Pro Ser Gly Ile Glu Asp Glu Phe
    450             455             460

Leu Ser Thr Ala Ser Glu Pro Pro Arg Lys Ser Phe Ile Ser Gly Phe
465             470             475             480

Asn Ala Asn Val Arg Leu Trp Gln Ser Ala Ala Asp Leu Leu Leu Glu
            485             490             495

Ile Arg Val Leu Gln Asp Gln Met Met Gln His Phe Arg Gly Thr Met
            500             505             510

Pro Pro Asn His Val Leu Pro Ser Ala Asp Arg Gln His Leu Asp Ser
    515             520             525

Leu Tyr Val Arg Phe Ile Thr Cys Leu Asp Asp Leu Pro Pro Tyr Leu
    530             535             540

Gln Ser Cys Thr Leu Ala Met Ala Ala Met Ala Glu Gly Asn Gly Ser
545             550             555             560

Ala Glu Ser Lys Gln Tyr Val Ile Gln Cys Ile Asn Leu Gln Val Thr
            565             570             575

Phe His Cys Leu Arg Met Val Ile Thr Gln Lys Phe Glu Asp Leu Ser
            580             585             590

Tyr Phe Ala Pro Gly Val Glu Gln Ala Asp Leu Arg Lys Ser Glu Ile
            595             600             605

Val Arg Asp Met Leu Arg Val Met Asn Glu Ala Pro Phe Trp Gly Leu
    610             615             620

Gln Ala Asn Gly Glu Pro Asn Val Glu Lys Ile Arg Leu Ile Gly Ala
625             630             635             640

Ser Leu Leu Ala Ile Ile His Arg Asn Gln Asp Ser Pro Leu Ala Thr
            645             650             655

Arg Ala Arg Ser Asp Phe Ser Val Leu Leu Asp Ile Leu Thr Arg Leu
            660             665             670

Asp Ser Lys
        675
```

-continued

```
<210> SEQ ID NO 16
<211> LENGTH: 674
<212> TYPE: PRT
<213> ORGANISM: Hypocrea jecorina

<400> SEQUENCE: 16

Met Gly Ser Ala Ala Pro Ala Gln Gly Ser Val Ala Ala Ala Ala Gly
1               5                   10                  15

Gly Pro Pro Ala Ala Gly Ala Gly Ala Gly Ala Val His Ala Leu Thr
            20                  25                  30

Thr Ser Pro Glu Ser Ala Ser Ala Ser Gln Pro Gly Ser Pro Thr Ala
        35                  40                  45

Ser Thr Thr Pro Pro Gln Asn Ser Leu Val Ser Ala Ala Thr Ser Phe
    50                  55                  60

His His His Pro Arg Gly Arg Leu Val Ser Arg Ala Cys Asp Arg Cys
65                  70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
            100                 105                 110

Ala Arg Arg Gly Pro Lys Ala Arg Lys Lys Ser Asp Gln Pro Gly Gln
            115                 120                 125

Pro Pro Pro Asp Pro Ser Ser Leu Ser Thr Ala Ala Arg Pro Gly Gln
    130                 135                 140

Met Pro Pro Pro Leu Thr Phe Ser Gly Pro Ala Val Ala Ala Leu Gln
145                 150                 155                 160

Pro Phe Ala Ser Ser Ser Leu Ser Pro Asp Ala Ala Trp Glu Pro Val
                165                 170                 175

Glu Pro Leu Ser Ile Asp Asn Gly Leu Pro Arg Gln Pro Leu Gly Asp
            180                 185                 190

Leu Pro Gly Leu Ser Thr Ile Gln Asn Ile Ser Thr Arg Gln Arg Trp
            195                 200                 205

Ile His Leu Ala Asn Ala Met Thr Leu Arg Asn Thr Thr Leu Glu Arg
    210                 215                 220

Val Ser Lys Arg Cys Ile Asp Leu Phe Phe Asp Tyr Leu Tyr Pro Leu
225                 230                 235                 240

Thr Pro Leu Val Tyr Glu Pro Ala Leu Arg Asp Val Leu Ala Tyr Ile
                245                 250                 255

Phe Ser Gln Pro Leu Pro Gly Val Asn Gln Pro Ser Pro Leu Ser Gln
            260                 265                 270

Leu Thr Pro Asp Pro Thr Thr Gly Thr Thr Pro Leu Asn Ala Ala Glu
            275                 280                 285

Ser Trp Ala Gly Phe Gly Gln Pro Ser Gly Ser Arg Thr Val Gly Ser
    290                 295                 300

Arg Leu Ala Pro Trp Ala Asp Ser Thr Phe Thr Leu Val Thr Ala Val
305                 310                 315                 320

Cys Ala Glu Ala Ala Phe Met Leu Pro Lys Asp Ile Phe Pro Glu Gly
                325                 330                 335

Glu Ser Val Ser Glu Ile Leu Leu Glu Ala Ser Arg Asp Cys Leu His
            340                 345                 350

Gln His Leu Glu Ala Asp Leu Glu Asn Pro Thr Ala Asn Ser Ile Ala
            355                 360                 365

Ile Arg Tyr Phe His Ser Asn Cys Leu His Ala Ala Gly Lys Pro Lys
    370                 375                 380
```

-continued

```
Tyr Ser Trp His Ile Phe Gly Glu Ala Ile Arg Leu Ala Gln Val Met
385                 390                 395                 400

Gln Leu His Glu Glu Ala Ala Leu Glu Gly Leu Val Pro Ile Glu Ala
                405                 410                 415

Glu Phe Arg Arg Arg Cys Phe Trp Ile Leu Tyr Leu Gly Asp Lys Ser
            420                 425                 430

Ala Ala Ile Leu Asn Asn Arg Pro Ile Thr Ile His Lys Tyr Cys Phe
            435                 440                 445

Asp Ala Gly Ile Thr Thr Leu Tyr Pro Ser Gly Ile Glu Asp Glu Phe
        450                 455                 460

Leu Ser Thr Ala Ser Glu Pro Pro Arg Lys Ser Phe Ile Ser Gly Phe
465                 470                 475                 480

Asn Ala Asn Val Arg Leu Trp Gln Ser Ala Ala Asp Leu Leu Leu Glu
                485                 490                 495

Ile Arg Val Leu Gln Asp Gln Met Met Gln His Phe Arg Gly Thr Met
            500                 505                 510

Pro Pro Asn His Val Leu Pro Ser Ala Asp Arg Gln His Leu Asp Ser
            515                 520                 525

Leu Tyr Val Arg Phe Ile Thr Cys Leu Asp Asp Leu Pro Pro Tyr Leu
        530                 535                 540

Gln Ser Cys Thr Leu Ala Met Ala Ala Met Ala Glu Gly Asn Gly Ser
545                 550                 555                 560

Ala Glu Ser Lys Gln Tyr Val Ile Gln Cys Ile Asn Leu Gln Val Thr
                565                 570                 575

Phe His Cys Leu Arg Met Val Ile Thr Gln Lys Phe Glu Asp Leu Ser
            580                 585                 590

Tyr Phe Ala Pro Gly Val Glu Gln Ala Asp Leu Arg Lys Ser Glu Ile
            595                 600                 605

Val Arg Asp Met Leu Arg Val Met Asn Glu Ala Pro Phe Trp Gly Leu
        610                 615                 620

Gln Ala Asn Gly Glu Pro Asn Val Glu Lys Ile Arg Leu Ile Gly Ala
625                 630                 635                 640

Ser Leu Leu Ala Ile Ile His Arg Asn Gln Asp Ser Pro Leu Ala Thr
                645                 650                 655

Arg Ala Arg Ser Asp Phe Ser Val Leu Leu Asp Ile Leu Thr Arg Leu
            660                 665                 670

Asp Ser
```

```
<210> SEQ ID NO 17
<211> LENGTH: 673
<212> TYPE: PRT
<213> ORGANISM: Hypocrea jecorina

<400> SEQUENCE: 17
```

```
Met Gly Ser Ala Ala Pro Ala Gln Gly Ser Val Ala Ala Ala Ala Gly
1               5                   10                  15

Gly Pro Pro Ala Ala Gly Ala Gly Ala Gly Ala Val His Ala Leu Thr
                20                  25                  30

Thr Ser Pro Glu Ser Ala Ser Ala Ser Gln Pro Gly Ser Pro Thr Ala
            35                  40                  45

Ser Thr Thr Pro Pro Gln Asn Ser Leu Val Ser Ala Ala Thr Ser Phe
        50                  55                  60

His His His Pro Arg Gly Arg Leu Val Ser Arg Ala Cys Asp Arg Cys
65                  70                  75                  80
```

-continued

```
Arg Arg Arg Lys Ala Lys Cys Glu Tyr Leu Ser Ala Val Asp Ser Cys
             85              90              95

Thr His Cys Arg Asp Ala His Val Gln Cys Thr Phe Asp Leu Pro Leu
            100             105             110

Ala Arg Arg Gly Pro Lys Ala Arg Lys Lys Ser Asp Gln Pro Gly Gln
            115             120             125

Pro Pro Pro Asp Pro Ser Ser Leu Ser Thr Ala Ala Arg Pro Gly Gln
        130             135             140

Met Pro Pro Pro Leu Thr Phe Ser Gly Pro Ala Val Ala Ala Leu Gln
145             150             155             160

Pro Phe Ala Ser Ser Ser Leu Ser Pro Asp Ala Ala Trp Glu Pro Val
            165             170             175

Glu Pro Leu Ser Ile Asp Asn Gly Leu Pro Arg Gln Pro Leu Gly Asp
            180             185             190

Leu Pro Gly Leu Ser Thr Ile Gln Asn Ile Ser Thr Arg Gln Arg Trp
            195             200             205

Ile His Leu Ala Asn Ala Met Thr Leu Arg Asn Thr Thr Leu Glu Arg
        210             215             220

Val Ser Lys Arg Cys Ile Asp Leu Phe Phe Asp Tyr Leu Tyr Pro Leu
225             230             235             240

Thr Pro Leu Val Tyr Glu Pro Ala Leu Arg Asp Val Leu Ala Tyr Ile
            245             250             255

Phe Ser Gln Pro Leu Pro Gly Val Asn Gln Pro Ser Pro Leu Ser Gln
            260             265             270

Leu Thr Pro Asp Pro Thr Thr Gly Thr Thr Pro Leu Asn Ala Ala Glu
            275             280             285

Ser Trp Ala Gly Phe Gly Gln Pro Ser Gly Ser Arg Thr Val Gly Ser
    290             295             300

Arg Leu Ala Pro Trp Ala Asp Ser Thr Phe Thr Leu Val Thr Ala Val
305             310             315             320

Cys Ala Glu Ala Ala Phe Met Leu Pro Lys Asp Ile Phe Pro Glu Gly
            325             330             335

Glu Ser Val Ser Glu Ile Leu Leu Glu Ala Ser Arg Asp Cys Leu His
            340             345             350

Gln His Leu Glu Ala Asp Leu Glu Asn Pro Thr Ala Asn Ser Ile Ala
            355             360             365

Ile Arg Tyr Phe His Ser Asn Cys Leu His Ala Ala Gly Lys Pro Lys
    370             375             380

Tyr Ser Trp His Ile Phe Gly Glu Ala Ile Arg Leu Ala Gln Val Met
385             390             395             400

Gln Leu His Glu Glu Ala Ala Leu Glu Gly Leu Val Pro Ile Glu Ala
            405             410             415

Glu Phe Arg Arg Arg Cys Phe Trp Ile Leu Tyr Leu Gly Asp Lys Ser
            420             425             430

Ala Ala Ile Leu Asn Asn Arg Pro Ile Thr Ile His Lys Tyr Cys Phe
        435             440             445

Asp Ala Gly Ile Thr Thr Leu Tyr Pro Ser Gly Ile Glu Asp Glu Phe
    450             455             460

Leu Ser Thr Ala Ser Glu Pro Pro Arg Lys Ser Phe Ile Ser Gly Phe
465             470             475             480

Asn Ala Asn Val Arg Leu Trp Gln Ser Ala Ala Asp Leu Leu Leu Glu
            485             490             495
```

```
Ile Arg Val Leu Gln Asp Gln Met Met Gln His Phe Arg Gly Thr Met
            500             505             510

Pro Pro Asn His Val Leu Pro Ser Ala Asp Arg Gln His Leu Asp Ser
            515             520             525

Leu Tyr Val Arg Phe Ile Thr Cys Leu Asp Asp Leu Pro Pro Tyr Leu
            530             535             540

Gln Ser Cys Thr Leu Ala Met Ala Ala Met Ala Glu Gly Asn Gly Ser
545             550             555             560

Ala Glu Ser Lys Gln Tyr Val Ile Gln Cys Ile Asn Leu Gln Val Thr
                565             570             575

Phe His Cys Leu Arg Met Val Ile Thr Gln Lys Phe Glu Asp Leu Ser
            580             585             590

Tyr Phe Ala Pro Gly Val Glu Gln Ala Asp Leu Arg Lys Ser Glu Ile
            595             600             605

Val Arg Asp Met Leu Arg Val Met Asn Glu Ala Pro Phe Trp Gly Leu
            610             615             620

Gln Ala Asn Gly Glu Pro Asn Val Glu Lys Ile Arg Leu Ile Gly Ala
625             630             635             640

Ser Leu Leu Ala Ile Ile His Arg Asn Gln Asp Ser Pro Leu Ala Thr
                645             650             655

Arg Ala Arg Ser Asp Phe Ser Val Leu Leu Asp Ile Leu Thr Arg Leu
                660             665             670

Asp

<210> SEQ ID NO 18
<211> LENGTH: 672
<212> TYPE: PRT
<213> ORGANISM: Hypocrea jecorina

<400> SEQUENCE: 18

Met Gly Ser Ala Ala Pro Ala Gln Gly Ser Val Ala Ala Ala Ala Gly
1               5               10              15

Gly Pro Pro Ala Ala Gly Ala Gly Ala Gly Ala Val His Ala Leu Thr
                20              25              30

Thr Ser Pro Glu Ser Ala Ser Ala Ser Gln Pro Gly Ser Pro Thr Ala
            35              40              45

Ser Thr Thr Pro Pro Gln Asn Ser Leu Val Ser Ala Ala Thr Ser Phe
        50              55              60

His His His Pro Arg Gly Arg Leu Val Ser Arg Ala Cys Asp Arg Cys
65              70              75              80

Arg Arg Arg Lys Ala Lys Cys Glu Tyr Leu Ser Ala Val Asp Ser Cys
                85              90              95

Thr His Cys Arg Asp Ala His Val Gln Cys Thr Phe Asp Leu Pro Leu
            100             105             110

Ala Arg Arg Gly Pro Lys Ala Arg Lys Lys Ser Asp Gln Pro Gly Gln
            115             120             125

Pro Pro Pro Asp Pro Ser Ser Leu Ser Thr Ala Ala Arg Pro Gly Gln
            130             135             140

Met Pro Pro Pro Leu Thr Phe Ser Gly Pro Ala Val Ala Ala Leu Gln
145             150             155             160

Pro Phe Ala Ser Ser Ser Leu Ser Pro Asp Ala Ala Trp Glu Pro Val
                165             170             175

Glu Pro Leu Ser Ile Asp Asn Gly Leu Pro Arg Gln Pro Leu Gly Asp
            180             185             190
```

```
Leu Pro Gly Leu Ser Thr Ile Gln Asn Ile Ser Thr Arg Gln Arg Trp
        195                 200                 205

Ile His Leu Ala Asn Ala Met Thr Leu Arg Asn Thr Thr Leu Glu Arg
        210                 215                 220

Val Ser Lys Arg Cys Ile Asp Leu Phe Phe Asp Tyr Leu Tyr Pro Leu
225                 230                 235                 240

Thr Pro Leu Val Tyr Glu Pro Ala Leu Arg Asp Val Leu Ala Tyr Ile
                245                 250                 255

Phe Ser Gln Pro Leu Pro Gly Val Asn Gln Pro Ser Pro Leu Ser Gln
                260                 265                 270

Leu Thr Pro Asp Pro Thr Thr Gly Thr Thr Pro Leu Asn Ala Ala Glu
                275                 280                 285

Ser Trp Ala Gly Phe Gly Gln Pro Ser Gly Ser Arg Thr Val Gly Ser
        290                 295                 300

Arg Leu Ala Pro Trp Ala Asp Ser Thr Phe Thr Leu Val Thr Ala Val
305                 310                 315                 320

Cys Ala Glu Ala Ala Phe Met Leu Pro Lys Asp Ile Phe Pro Glu Gly
                325                 330                 335

Glu Ser Val Ser Glu Ile Leu Leu Glu Ala Ser Arg Asp Cys Leu His
                340                 345                 350

Gln His Leu Glu Ala Asp Leu Glu Asn Pro Thr Ala Asn Ser Ile Ala
        355                 360                 365

Ile Arg Tyr Phe His Ser Asn Cys Leu His Ala Ala Gly Lys Pro Lys
        370                 375                 380

Tyr Ser Trp His Ile Phe Gly Glu Ala Ile Arg Leu Ala Gln Val Met
385                 390                 395                 400

Gln Leu His Glu Glu Ala Ala Leu Glu Gly Leu Val Pro Ile Glu Ala
                405                 410                 415

Glu Phe Arg Arg Arg Cys Phe Trp Ile Leu Tyr Leu Gly Asp Lys Ser
                420                 425                 430

Ala Ala Ile Leu Asn Asn Arg Pro Ile Thr Ile His Lys Tyr Cys Phe
        435                 440                 445

Asp Ala Gly Ile Thr Thr Leu Tyr Pro Ser Gly Ile Glu Asp Glu Phe
        450                 455                 460

Leu Ser Thr Ala Ser Glu Pro Pro Arg Lys Ser Phe Ile Ser Gly Phe
465                 470                 475                 480

Asn Ala Asn Val Arg Leu Trp Gln Ser Ala Ala Asp Leu Leu Leu Glu
                485                 490                 495

Ile Arg Val Leu Gln Asp Gln Met Met Gln His Phe Arg Gly Thr Met
                500                 505                 510

Pro Pro Asn His Val Leu Pro Ser Ala Asp Arg Gln His Leu Asp Ser
        515                 520                 525

Leu Tyr Val Arg Phe Ile Thr Cys Leu Asp Asp Leu Pro Pro Tyr Leu
        530                 535                 540

Gln Ser Cys Thr Leu Ala Met Ala Ala Met Ala Glu Gly Asn Gly Ser
545                 550                 555                 560

Ala Glu Ser Lys Gln Tyr Val Ile Gln Cys Ile Asn Leu Gln Val Thr
                565                 570                 575

Phe His Cys Leu Arg Met Val Ile Thr Gln Lys Phe Glu Asp Leu Ser
                580                 585                 590

Tyr Phe Ala Pro Gly Val Glu Gln Ala Asp Leu Arg Lys Ser Glu Ile
                595                 600                 605

Val Arg Asp Met Leu Arg Val Met Asn Glu Ala Pro Phe Trp Gly Leu
```

-continued

```
        610             615             620

Gln Ala Asn Gly Glu Pro Asn Val Glu Lys Ile Arg Leu Ile Gly Ala
625             630             635             640

Ser Leu Leu Ala Ile Ile His Arg Asn Gln Asp Ser Pro Leu Ala Thr
            645             650             655

Arg Ala Arg Ser Asp Phe Ser Val Leu Leu Asp Ile Leu Thr Arg Leu
            660             665             670

<210> SEQ ID NO 19
<211> LENGTH: 671
<212> TYPE: PRT
<213> ORGANISM: Hypocrea jecorina

<400> SEQUENCE: 19

Met Gly Ser Ala Ala Pro Ala Gln Gly Ser Val Ala Ala Ala Ala Gly
1               5               10              15

Gly Pro Pro Ala Ala Gly Ala Gly Ala Gly Ala Val His Ala Leu Thr
            20              25              30

Thr Ser Pro Glu Ser Ala Ser Ala Ser Gln Pro Gly Ser Pro Thr Ala
        35              40              45

Ser Thr Thr Pro Pro Gln Asn Ser Leu Val Ser Ala Ala Thr Ser Phe
    50              55              60

His His His Pro Arg Gly Arg Leu Val Ser Arg Ala Cys Asp Arg Cys
65              70              75              80

Arg Arg Arg Lys Ala Lys Cys Glu Tyr Leu Ser Ala Val Asp Ser Cys
            85              90              95

Thr His Cys Arg Asp Ala His Val Gln Cys Thr Phe Asp Leu Pro Leu
        100             105             110

Ala Arg Arg Gly Pro Lys Ala Arg Lys Lys Ser Asp Gln Pro Gly Gln
        115             120             125

Pro Pro Pro Asp Pro Ser Ser Leu Ser Thr Ala Ala Arg Pro Gly Gln
    130             135             140

Met Pro Pro Pro Leu Thr Phe Ser Gly Pro Ala Val Ala Ala Leu Gln
145             150             155             160

Pro Phe Ala Ser Ser Ser Leu Ser Pro Asp Ala Ala Trp Glu Pro Val
            165             170             175

Glu Pro Leu Ser Ile Asp Asn Gly Leu Pro Arg Gln Pro Leu Gly Asp
            180             185             190

Leu Pro Gly Leu Ser Thr Ile Gln Asn Ile Ser Thr Arg Gln Arg Trp
        195             200             205

Ile His Leu Ala Asn Ala Met Thr Leu Arg Asn Thr Thr Leu Glu Arg
    210             215             220

Val Ser Lys Arg Cys Ile Asp Leu Phe Phe Asp Tyr Leu Tyr Pro Leu
225             230             235             240

Thr Pro Leu Val Tyr Glu Pro Ala Leu Arg Asp Val Leu Ala Tyr Ile
            245             250             255

Phe Ser Gln Pro Leu Pro Gly Val Asn Gln Pro Ser Pro Leu Ser Gln
            260             265             270

Leu Thr Pro Asp Pro Thr Thr Gly Thr Thr Pro Leu Asn Ala Ala Glu
        275             280             285

Ser Trp Ala Gly Phe Gly Gln Pro Ser Gly Ser Arg Thr Val Gly Ser
    290             295             300

Arg Leu Ala Pro Trp Ala Asp Ser Thr Phe Thr Leu Val Thr Ala Val
305             310             315             320
```

-continued

```
Cys Ala Glu Ala Ala Phe Met Leu Pro Lys Asp Ile Phe Pro Glu Gly
                325                 330                 335

Glu Ser Val Ser Glu Ile Leu Leu Glu Ala Ser Arg Asp Cys Leu His
            340                 345                 350

Gln His Leu Glu Ala Asp Leu Glu Asn Pro Thr Ala Asn Ser Ile Ala
        355                 360                 365

Ile Arg Tyr Phe His Ser Asn Cys Leu His Ala Ala Gly Lys Pro Lys
    370                 375                 380

Tyr Ser Trp His Ile Phe Gly Glu Ala Ile Arg Leu Ala Gln Val Met
385                 390                 395                 400

Gln Leu His Glu Glu Ala Ala Leu Glu Gly Leu Val Pro Ile Glu Ala
                405                 410                 415

Glu Phe Arg Arg Arg Cys Phe Trp Ile Leu Tyr Leu Gly Asp Lys Ser
            420                 425                 430

Ala Ala Ile Leu Asn Asn Arg Pro Ile Thr Ile His Lys Tyr Cys Phe
            435                 440                 445

Asp Ala Gly Ile Thr Thr Leu Tyr Pro Ser Gly Ile Glu Asp Glu Phe
        450                 455                 460

Leu Ser Thr Ala Ser Glu Pro Pro Arg Lys Ser Phe Ile Ser Gly Phe
465                 470                 475                 480

Asn Ala Asn Val Arg Leu Trp Gln Ser Ala Ala Asp Leu Leu Leu Glu
                485                 490                 495

Ile Arg Val Leu Gln Asp Gln Met Met Gln His Phe Arg Gly Thr Met
            500                 505                 510

Pro Pro Asn His Val Leu Pro Ser Ala Asp Arg Gln His Leu Asp Ser
            515                 520                 525

Leu Tyr Val Arg Phe Ile Thr Cys Leu Asp Asp Leu Pro Pro Tyr Leu
        530                 535                 540

Gln Ser Cys Thr Leu Ala Met Ala Ala Met Ala Glu Gly Asn Gly Ser
545                 550                 555                 560

Ala Glu Ser Lys Gln Tyr Val Ile Gln Cys Ile Asn Leu Gln Val Thr
                565                 570                 575

Phe His Cys Leu Arg Met Val Ile Thr Gln Lys Phe Glu Asp Leu Ser
            580                 585                 590

Tyr Phe Ala Pro Gly Val Glu Gln Ala Asp Leu Arg Lys Ser Glu Ile
        595                 600                 605

Val Arg Asp Met Leu Arg Val Met Asn Glu Ala Pro Phe Trp Gly Leu
    610                 615                 620

Gln Ala Asn Gly Glu Pro Asn Val Glu Lys Ile Arg Leu Ile Gly Ala
625                 630                 635                 640

Ser Leu Leu Ala Ile Ile His Arg Asn Gln Asp Ser Pro Leu Ala Thr
                645                 650                 655

Arg Ala Arg Ser Asp Phe Ser Val Leu Leu Asp Ile Leu Thr Arg
                660                 665                 670
```

```
<210> SEQ ID NO 20
<211> LENGTH: 670
<212> TYPE: PRT
<213> ORGANISM: Hypocrea jecorina

<400> SEQUENCE: 20

Met Gly Ser Ala Ala Pro Ala Gln Gly Ser Val Ala Ala Ala Gly
1               5                   10                  15

Gly Pro Pro Ala Ala Gly Ala Gly Ala Gly Ala Val His Ala Leu Thr
            20                  25                  30
```

-continued

Thr Ser Pro Glu Ser Ala Ser Ala Ser Gln Pro Gly Ser Pro Thr Ala
            35                  40                  45

Ser Thr Thr Pro Pro Gln Asn Ser Leu Val Ser Ala Ala Thr Ser Phe
        50                  55                  60

His His His Pro Arg Gly Arg Leu Val Ser Arg Ala Cys Asp Arg Cys
65                  70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
            100                 105                 110

Ala Arg Arg Gly Pro Lys Ala Arg Lys Lys Ser Asp Gln Pro Gly Gln
            115                 120                 125

Pro Pro Pro Asp Pro Ser Ser Leu Ser Thr Ala Ala Arg Pro Gly Gln
        130                 135                 140

Met Pro Pro Pro Leu Thr Phe Ser Gly Pro Ala Val Ala Ala Leu Gln
145                 150                 155                 160

Pro Phe Ala Ser Ser Ser Leu Ser Pro Asp Ala Ala Trp Glu Pro Val
                165                 170                 175

Glu Pro Leu Ser Ile Asp Asn Gly Leu Pro Arg Gln Pro Leu Gly Asp
            180                 185                 190

Leu Pro Gly Leu Ser Thr Ile Gln Asn Ile Ser Thr Arg Gln Arg Trp
            195                 200                 205

Ile His Leu Ala Asn Ala Met Thr Leu Arg Asn Thr Thr Leu Glu Arg
            210                 215                 220

Val Ser Lys Arg Cys Ile Asp Leu Phe Phe Asp Tyr Leu Tyr Pro Leu
225                 230                 235                 240

Thr Pro Leu Val Tyr Glu Pro Ala Leu Arg Asp Val Leu Ala Tyr Ile
                245                 250                 255

Phe Ser Gln Pro Leu Pro Gly Val Asn Gln Pro Ser Pro Leu Ser Gln
                260                 265                 270

Leu Thr Pro Asp Pro Thr Thr Gly Thr Thr Pro Leu Asn Ala Ala Glu
            275                 280                 285

Ser Trp Ala Gly Phe Gly Gln Pro Ser Gly Ser Arg Thr Val Gly Ser
        290                 295                 300

Arg Leu Ala Pro Trp Ala Asp Ser Thr Phe Thr Leu Val Thr Ala Val
305                 310                 315                 320

Cys Ala Glu Ala Ala Phe Met Leu Pro Lys Asp Ile Phe Pro Glu Gly
                325                 330                 335

Glu Ser Val Ser Glu Ile Leu Leu Glu Ala Ser Arg Asp Cys Leu His
                340                 345                 350

Gln His Leu Glu Ala Asp Leu Glu Asn Pro Thr Ala Asn Ser Ile Ala
            355                 360                 365

Ile Arg Tyr Phe His Ser Asn Cys Leu His Ala Ala Gly Lys Pro Lys
        370                 375                 380

Tyr Ser Trp His Ile Phe Gly Glu Ala Ile Arg Leu Ala Gln Val Met
385                 390                 395                 400

Gln Leu His Glu Glu Ala Ala Leu Glu Gly Leu Val Pro Ile Glu Ala
                405                 410                 415

Glu Phe Arg Arg Arg Cys Phe Trp Ile Leu Tyr Leu Gly Asp Lys Ser
            420                 425                 430

Ala Ala Ile Leu Asn Asn Arg Pro Ile Thr Ile His Lys Tyr Cys Phe
            435                 440                 445

-continued

```
Asp Ala Gly Ile Thr Thr Leu Tyr Pro Ser Gly Ile Glu Asp Glu Phe
    450             455             460

Leu Ser Thr Ala Ser Glu Pro Pro Arg Lys Ser Phe Ile Ser Gly Phe
465             470             475             480

Asn Ala Asn Val Arg Leu Trp Gln Ser Ala Ala Asp Leu Leu Leu Glu
                485             490             495

Ile Arg Val Leu Gln Asp Gln Met Met Gln His Phe Arg Gly Thr Met
            500             505             510

Pro Pro Asn His Val Leu Pro Ser Ala Asp Arg Gln His Leu Asp Ser
            515             520             525

Leu Tyr Val Arg Phe Ile Thr Cys Leu Asp Asp Leu Pro Pro Tyr Leu
    530             535             540

Gln Ser Cys Thr Leu Ala Met Ala Ala Met Ala Glu Gly Asn Gly Ser
545             550             555             560

Ala Glu Ser Lys Gln Tyr Val Ile Gln Cys Ile Asn Leu Gln Val Thr
                565             570             575

Phe His Cys Leu Arg Met Val Ile Thr Gln Lys Phe Glu Asp Leu Ser
            580             585             590

Tyr Phe Ala Pro Gly Val Glu Gln Ala Asp Leu Arg Lys Ser Glu Ile
            595             600             605

Val Arg Asp Met Leu Arg Val Met Asn Glu Ala Pro Phe Trp Gly Leu
    610             615             620

Gln Ala Asn Gly Glu Pro Asn Val Glu Lys Ile Arg Leu Ile Gly Ala
625             630             635             640

Ser Leu Leu Ala Ile Ile His Arg Asn Gln Asp Ser Pro Leu Ala Thr
            645             650             655

Arg Ala Arg Ser Asp Phe Ser Val Leu Leu Asp Ile Leu Thr
            660             665             670

<210> SEQ ID NO 21
<211> LENGTH: 669
<212> TYPE: PRT
<213> ORGANISM: Hypocrea jecorina

<400> SEQUENCE: 21

Met Gly Ser Ala Ala Pro Ala Gln Gly Ser Val Ala Ala Ala Ala Gly
1               5               10              15

Gly Pro Pro Ala Ala Gly Ala Gly Ala Gly Ala Val His Ala Leu Thr
            20              25              30

Thr Ser Pro Glu Ser Ala Ser Ala Ser Gln Pro Gly Ser Pro Thr Ala
            35              40              45

Ser Thr Thr Pro Pro Gln Asn Ser Leu Val Ser Ala Ala Thr Ser Phe
    50              55              60

His His His Pro Arg Gly Arg Leu Val Ser Arg Ala Cys Asp Arg Cys
65              70              75              80

Arg Arg Arg Lys Ala Lys Cys Glu Tyr Leu Ser Ala Val Asp Ser Cys
                85              90              95

Thr His Cys Arg Asp Ala His Val Gln Cys Thr Phe Asp Leu Pro Leu
            100             105             110

Ala Arg Arg Gly Pro Lys Ala Arg Lys Lys Ser Asp Gln Pro Gly Gln
            115             120             125

Pro Pro Pro Asp Pro Ser Ser Leu Ser Thr Ala Ala Arg Pro Gly Gln
    130             135             140

Met Pro Pro Pro Leu Thr Phe Ser Gly Pro Ala Val Ala Ala Leu Gln
145             150             155             160
```

```
Pro Phe Ala Ser Ser Ser Leu Ser Pro Asp Ala Ala Trp Glu Pro Val
            165             170             175

Glu Pro Leu Ser Ile Asp Asn Gly Leu Pro Arg Gln Pro Leu Gly Asp
            180             185             190

Leu Pro Gly Leu Ser Thr Ile Gln Asn Ile Ser Thr Arg Gln Arg Trp
            195             200             205

Ile His Leu Ala Asn Ala Met Thr Leu Arg Asn Thr Thr Leu Glu Arg
            210             215             220

Val Ser Lys Arg Cys Ile Asp Leu Phe Phe Asp Tyr Leu Tyr Pro Leu
225             230             235             240

Thr Pro Leu Val Tyr Glu Pro Ala Leu Arg Asp Val Leu Ala Tyr Ile
            245             250             255

Phe Ser Gln Pro Leu Pro Gly Val Asn Gln Pro Ser Pro Leu Ser Gln
            260             265             270

Leu Thr Pro Asp Pro Thr Thr Gly Thr Thr Pro Leu Asn Ala Ala Glu
            275             280             285

Ser Trp Ala Gly Phe Gly Gln Pro Ser Gly Ser Arg Thr Val Gly Ser
    290             295             300

Arg Leu Ala Pro Trp Ala Asp Ser Thr Phe Thr Leu Val Thr Ala Val
305             310             315             320

Cys Ala Glu Ala Ala Phe Met Leu Pro Lys Asp Ile Phe Pro Glu Gly
            325             330             335

Glu Ser Val Ser Glu Ile Leu Leu Glu Ala Ser Arg Asp Cys Leu His
            340             345             350

Gln His Leu Glu Ala Asp Leu Glu Asn Pro Thr Ala Asn Ser Ile Ala
            355             360             365

Ile Arg Tyr Phe His Ser Asn Cys Leu His Ala Ala Gly Lys Pro Lys
            370             375             380

Tyr Ser Trp His Ile Phe Gly Glu Ala Ile Arg Leu Ala Gln Val Met
385             390             395             400

Gln Leu His Glu Glu Ala Ala Leu Glu Gly Leu Val Pro Ile Glu Ala
            405             410             415

Glu Phe Arg Arg Arg Cys Phe Trp Ile Leu Tyr Leu Gly Asp Lys Ser
            420             425             430

Ala Ala Ile Leu Asn Asn Arg Pro Ile Thr Ile His Lys Tyr Cys Phe
            435             440             445

Asp Ala Gly Ile Thr Thr Leu Tyr Pro Ser Gly Ile Glu Asp Glu Phe
    450             455             460

Leu Ser Thr Ala Ser Glu Pro Pro Arg Lys Ser Phe Ile Ser Gly Phe
465             470             475             480

Asn Ala Asn Val Arg Leu Trp Gln Ser Ala Ala Asp Leu Leu Leu Glu
            485             490             495

Ile Arg Val Leu Gln Asp Gln Met Met Gln His Phe Arg Gly Thr Met
            500             505             510

Pro Pro Asn His Val Leu Pro Ser Ala Asp Arg Gln His Leu Asp Ser
            515             520             525

Leu Tyr Val Arg Phe Ile Thr Cys Leu Asp Asp Leu Pro Pro Tyr Leu
    530             535             540

Gln Ser Cys Thr Leu Ala Met Ala Ala Met Ala Glu Gly Asn Gly Ser
545             550             555             560

Ala Glu Ser Lys Gln Tyr Val Ile Gln Cys Ile Asn Leu Gln Val Thr
            565             570             575
```

-continued

```
Phe His Cys Leu Arg Met Val Ile Thr Gln Lys Phe Glu Asp Leu Ser
            580                 585                 590

Tyr Phe Ala Pro Gly Val Glu Gln Ala Asp Leu Arg Lys Ser Glu Ile
            595                 600                 605

Val Arg Asp Met Leu Arg Val Met Asn Glu Ala Pro Phe Trp Gly Leu
            610                 615                 620

Gln Ala Asn Gly Glu Pro Asn Val Glu Lys Ile Arg Leu Ile Gly Ala
625                 630                 635                 640

Ser Leu Leu Ala Ile Ile His Arg Asn Gln Asp Ser Pro Leu Ala Thr
                645                 650                 655

Arg Ala Arg Ser Asp Phe Ser Val Leu Leu Asp Ile Leu
            660                 665

<210> SEQ ID NO 22
<211> LENGTH: 664
<212> TYPE: PRT
<213> ORGANISM: Hypocrea jecorina

<400> SEQUENCE: 22

Met Gly Ser Ala Ala Pro Ala Gln Gly Ser Val Ala Ala Ala Ala Gly
1               5                   10                  15

Gly Pro Pro Ala Ala Gly Ala Gly Ala Gly Ala Val His Ala Leu Thr
                20                  25                  30

Thr Ser Pro Glu Ser Ala Ser Ala Ser Gln Pro Gly Ser Pro Thr Ala
            35                  40                  45

Ser Thr Thr Pro Pro Gln Asn Ser Leu Val Ser Ala Ala Thr Ser Phe
            50                  55                  60

His His His Pro Arg Gly Arg Leu Val Ser Arg Ala Cys Asp Arg Cys
65                  70                  75                  80

Arg Arg Arg Lys Ala Lys Cys Glu Tyr Leu Ser Ala Val Asp Ser Cys
                85                  90                  95

Thr His Cys Arg Asp Ala His Val Gln Cys Thr Phe Asp Leu Pro Leu
            100                 105                 110

Ala Arg Arg Gly Pro Lys Ala Arg Lys Lys Ser Asp Gln Pro Gly Gln
            115                 120                 125

Pro Pro Pro Asp Pro Ser Ser Leu Ser Thr Ala Ala Arg Pro Gly Gln
            130                 135                 140

Met Pro Pro Pro Leu Thr Phe Ser Gly Pro Ala Val Ala Ala Leu Gln
145                 150                 155                 160

Pro Phe Ala Ser Ser Ser Leu Ser Pro Asp Ala Ala Trp Glu Pro Val
                165                 170                 175

Glu Pro Leu Ser Ile Asp Asn Gly Leu Pro Arg Gln Pro Leu Gly Asp
            180                 185                 190

Leu Pro Gly Leu Ser Thr Ile Gln Asn Ile Ser Thr Arg Gln Arg Trp
            195                 200                 205

Ile His Leu Ala Asn Ala Met Thr Leu Arg Asn Thr Thr Leu Glu Arg
            210                 215                 220

Val Ser Lys Arg Cys Ile Asp Leu Phe Phe Asp Tyr Leu Tyr Pro Leu
225                 230                 235                 240

Thr Pro Leu Val Tyr Glu Pro Ala Leu Arg Asp Val Leu Ala Tyr Ile
                245                 250                 255

Phe Ser Gln Pro Leu Pro Gly Val Asn Gln Pro Ser Pro Leu Ser Gln
            260                 265                 270

Leu Thr Pro Asp Pro Thr Thr Gly Thr Thr Pro Leu Asn Ala Ala Glu
            275                 280                 285
```

-continued

```
Ser Trp Ala Gly Phe Gly Gln Pro Ser Gly Ser Arg Thr Val Gly Ser
    290                 295                 300

Arg Leu Ala Pro Trp Ala Asp Ser Thr Phe Thr Leu Val Thr Ala Val
305                 310                 315                 320

Cys Ala Glu Ala Ala Phe Met Leu Pro Lys Asp Ile Phe Pro Glu Gly
                325                 330                 335

Glu Ser Val Ser Glu Ile Leu Leu Glu Ala Ser Arg Asp Cys Leu His
                340                 345                 350

Gln His Leu Glu Ala Asp Leu Glu Asn Pro Thr Ala Asn Ser Ile Ala
                355                 360                 365

Ile Arg Tyr Phe His Ser Asn Cys Leu His Ala Ala Gly Lys Pro Lys
    370                 375                 380

Tyr Ser Trp His Ile Phe Gly Glu Ala Ile Arg Leu Ala Gln Val Met
385                 390                 395                 400

Gln Leu His Glu Glu Ala Ala Leu Glu Gly Leu Val Pro Ile Glu Ala
                405                 410                 415

Glu Phe Arg Arg Arg Cys Phe Trp Ile Leu Tyr Leu Gly Asp Lys Ser
                420                 425                 430

Ala Ala Ile Leu Asn Asn Arg Pro Ile Thr Ile His Lys Tyr Cys Phe
                435                 440                 445

Asp Ala Gly Ile Thr Thr Leu Tyr Pro Ser Gly Ile Glu Asp Glu Phe
    450                 455                 460

Leu Ser Thr Ala Ser Glu Pro Pro Arg Lys Ser Phe Ile Ser Gly Phe
465                 470                 475                 480

Asn Ala Asn Val Arg Leu Trp Gln Ser Ala Ala Asp Leu Leu Leu Glu
                485                 490                 495

Ile Arg Val Leu Gln Asp Gln Met Met Gln His Phe Arg Gly Thr Met
                500                 505                 510

Pro Pro Asn His Val Leu Pro Ser Ala Asp Arg Gln His Leu Asp Ser
                515                 520                 525

Leu Tyr Val Arg Phe Ile Thr Cys Leu Asp Asp Leu Pro Pro Tyr Leu
    530                 535                 540

Gln Ser Cys Thr Leu Ala Met Ala Ala Met Ala Glu Gly Asn Gly Ser
545                 550                 555                 560

Ala Glu Ser Lys Gln Tyr Val Ile Gln Cys Ile Asn Leu Gln Val Thr
                565                 570                 575

Phe His Cys Leu Arg Met Val Ile Thr Gln Lys Phe Glu Asp Leu Ser
                580                 585                 590

Tyr Phe Ala Pro Gly Val Glu Gln Ala Asp Leu Arg Lys Ser Glu Ile
                595                 600                 605

Val Arg Asp Met Leu Arg Val Met Asn Glu Ala Pro Phe Trp Gly Leu
    610                 615                 620

Gln Ala Asn Gly Glu Pro Asn Val Glu Lys Ile Arg Leu Ile Gly Ala
625                 630                 635                 640

Ser Leu Leu Ala Ile Ile His Arg Asn Gln Asp Ser Pro Leu Ala Thr
                645                 650                 655

Arg Ala Arg Ser Asp Phe Ser Val
                660
```

<210> SEQ ID NO 23
<211> LENGTH: 19
<212> TYPE: DNA
<213> ORGANISM: Artificial Sequence
<220> FEATURE:

-continued

```
<223> OTHER INFORMATION: primer sequence

<400> SEQUENCE: 23
cgcatggtaa ttacgcaga                                              19

<210> SEQ ID NO 24
<211> LENGTH: 20
<212> TYPE: DNA
<213> ORGANISM: Artificial Sequence
<220> FEATURE:
<223> OTHER INFORMATION: primer sequence

<400> SEQUENCE: 24
gtccatgagc ttgaacaggt                                             20

<210> SEQ ID NO 25
<211> LENGTH: 22
<212> TYPE: DNA
<213> ORGANISM: Artificial Sequence
<220> FEATURE:
<223> OTHER INFORMATION: primer sequence

<400> SEQUENCE: 25
agcagatccc gttaccgatt ca                                          22

<210> SEQ ID NO 26
<211> LENGTH: 20
<212> TYPE: DNA
<213> ORGANISM: Artificial Sequence
<220> FEATURE:
<223> OTHER INFORMATION: primer sequence

<400> SEQUENCE: 26
gtcgagtcca cgtcgtctct                                             20

<210> SEQ ID NO 27
<211> LENGTH: 25
<212> TYPE: DNA
<213> ORGANISM: Artificial Sequence
<220> FEATURE:
<223> OTHER INFORMATION: primer sequence

<400> SEQUENCE: 27
tgttatgacg taccagttgg gatga                                       25

<210> SEQ ID NO 28
<211> LENGTH: 20
<212> TYPE: DNA
<213> ORGANISM: Artificial Sequence
<220> FEATURE:
<223> OTHER INFORMATION: primer sequence

<400> SEQUENCE: 28
ccgctcaggc atacgagcga                                             20

<210> SEQ ID NO 29
<211> LENGTH: 37
<212> TYPE: PRT
<213> ORGANISM: Hypocrea jecorina

<400> SEQUENCE: 29

Val Ser Arg Ala Cys Asp Arg Cys Arg Arg Lys Ala Lys Cys Glu
1               5                   10                  15

Tyr Leu Ser Ala Val Asp Ser Cys Thr His Cys Arg Asp Ala His Val
            20                  25                  30
```

```
Gln Cys Thr Phe Asp
        35

<210> SEQ ID NO 30
<211> LENGTH: 49
<212> TYPE: PRT
<213> ORGANISM: Hypocrea jecorina

<400> SEQUENCE: 30

Ser Leu Leu Ala Ile Ile His Arg Asn Gln Asp Ser Pro Leu Ala Thr
1               5                   10                  15

Arg Ala Arg Ser Asp Phe Ser Val Leu Leu Asp Ile Leu Thr Arg Leu
            20                  25                  30

Asp Ser Lys Ala Ser Asp Gln Leu Arg Asn Thr Ser Thr Thr Val Val
        35                  40                  45

Gly

<210> SEQ ID NO 31
<211> LENGTH: 147
<212> TYPE: DNA
<213> ORGANISM: Hypocrea jecorina

<400> SEQUENCE: 31
agtttgctgg ccatcatcca tcgcaaccag gattcaccct tggctacgcg agccaggagc      60
gacttttccg tgcttttgga tattctcacg cggctggact cgaaggcgtc ggaccaactg     120
aggaatacgt ccactaccgt tgttggc                                         147

<210> SEQ ID NO 32
<211> LENGTH: 147
<212> TYPE: DNA
<213> ORGANISM: Hypocrea jecorina
<220> FEATURE:
<221> NAME/KEY: misc_feature
<222> LOCATION: (97)..(99)
<223> OTHER INFORMATION: n = G, C, T or A nuclotide; k = G or T
      nucleotide

<400> SEQUENCE: 32
agtttgctgg ccatcatcca tcgcaaccag gattcaccct tggctacgcg agccaggagc      60
gacttttccg tgcttttgga tattctcacg cggctgnnkt cgaaggcgtc ggaccaactg     120
aggaatacgt ccactaccgt tgttggc                                         147

<210> SEQ ID NO 33
<211> LENGTH: 147
<212> TYPE: DNA
<213> ORGANISM: Hypocrea jecorina
<220> FEATURE:
<221> NAME/KEY: misc_feature
<222> LOCATION: (99)..(101)
<223> OTHER INFORMATION: n = G, C, T or A nuclotide; k = G or T
      nucleotide

<400> SEQUENCE: 33
agtttgctgg ccatcatcca tcgcaaccag gattcaccct tggctacgcg agccaggagc      60
gacttttccg tgcttttgga tattctcacg cggctggacn nkaaggcgtc ggaccaactg     120
aggaatacgt ccactaccgt tgttggc                                         147

<210> SEQ ID NO 34
<211> LENGTH: 147
<212> TYPE: DNA
```

-continued

```
<213> ORGANISM: Hypocrea jecorina
<220> FEATURE:
<221> NAME/KEY: misc_feature
<222> LOCATION: (103)..(105)
<223> OTHER INFORMATION: n = G, C, T or A nuclotide; k = G or T
      nucleotide

<400> SEQUENCE: 34
agtttgctgg ccatcatcca tcgcaaccag gattcaccct tggctacgcg agccaggagc      60
gacttttccg tgcttttgga tattctcacg cggctggact cgnnkgcgtc ggaccaactg     120
aggaatacgt ccactaccgt tgttggc                                        147

<210> SEQ ID NO 35
<211> LENGTH: 147
<212> TYPE: DNA
<213> ORGANISM: Hypocrea jecorina
<220> FEATURE:
<221> NAME/KEY: misc_feature
<222> LOCATION: (106)..(108)
<223> OTHER INFORMATION: n = G, C, T or A nuclotide; k = G or T
      nucleotide

<400> SEQUENCE: 35
agtttgctgg ccatcatcca tcgcaaccag gattcaccct tggctacgcg agccaggagc      60
gacttttccg tgcttttgga tattctcacg cggctggact cgaagnnktc ggaccaactg     120
aggaatacgt ccactaccgt tgttggc                                        147

<210> SEQ ID NO 36
<211> LENGTH: 147
<212> TYPE: DNA
<213> ORGANISM: Hypocrea jecorina
<220> FEATURE:
<221> NAME/KEY: misc_feature
<222> LOCATION: (109)..(111)
<223> OTHER INFORMATION: n = G, C, T or A nuclotide; k = G or T
      nucleotide

<400> SEQUENCE: 36
agtttgctgg ccatcatcca tcgcaaccag gattcaccct tggctacgcg agccaggagc      60
gacttttccg tgcttttgga tattctcacg cggctggact cgaaggcgnn kgaccaactg     120
aggaatacgt ccactaccgt tgttggc                                        147

<210> SEQ ID NO 37
<211> LENGTH: 147
<212> TYPE: DNA
<213> ORGANISM: Hypocrea jecorina
<220> FEATURE:
<221> NAME/KEY: misc_feature
<222> LOCATION: (112)..(114)
<223> OTHER INFORMATION: n = G, C, T or A nuclotide; k = G or T
      nucleotide

<400> SEQUENCE: 37
agtttgctgg ccatcatcca tcgcaaccag gattcaccct tggctacgcg agccaggagc      60
gacttttccg tgcttttgga tattctcacg cggctggact cgaaggcgtc gnnkcaactg     120
aggaatacgt ccactaccgt tgttggc                                        147

<210> SEQ ID NO 38
<211> LENGTH: 147
<212> TYPE: DNA
<213> ORGANISM: Hypocrea jecorina
<220> FEATURE:
<221> NAME/KEY: misc_feature
```

-continued

```
<222> LOCATION: (115)..(117)
<223> OTHER INFORMATION: n = G, C, T or A nuclotide; k = G or T
      nucleotide

<400> SEQUENCE: 38
agtttgctgg ccatcatcca tcgcaaccag gattcaccct tggctacgcg agccaggagc      60 gactttttccg tgcttttgga tattctcacg cggctggact cgaaggcgtc ggacnnkctg     120
aggaatacgt ccactaccgt tgttggc                                          147

<210> SEQ ID NO 39
<211> LENGTH: 147
<212> TYPE: DNA
<213> ORGANISM: Hypocrea jecorina
<220> FEATURE:
<221> NAME/KEY: misc_feature
<222> LOCATION: (118)..(120)
<223> OTHER INFORMATION: n = G, C, T or A nuclotide; k = G or T
      nucleotide

<400> SEQUENCE: 39
agtttgctgg ccatcatcca tcgcaaccag gattcaccct tggctacgcg agccaggagc      60 gactttttccg tgcttttgga tattctcacg cggctggact cgaaggcgtc ggaccaannk     120
aggaatacgt ccactaccgt tgttggc                                          147

<210> SEQ ID NO 40
<211> LENGTH: 147
<212> TYPE: DNA
<213> ORGANISM: Hypocrea jecorina
<220> FEATURE:
<221> NAME/KEY: misc_feature
<222> LOCATION: (121)..(123)
<223> OTHER INFORMATION: n = G, C, T or A nuclotide; k = G or T
      nucleotide

<400> SEQUENCE: 40
agtttgctgg ccatcatcca tcgcaaccag gattcaccct tggctacgcg agccaggagc      60 gactttttccg tgcttttgga tattctcacg cggctggact cgaaggcgtc ggaccaactg     120
nnkaatacgt ccactaccgt tgttggc                                          147

<210> SEQ ID NO 41
<211> LENGTH: 147
<212> TYPE: DNA
<213> ORGANISM: Hypocrea jecorina
<220> FEATURE:
<221> NAME/KEY: misc_feature
<222> LOCATION: (124)..(126)
<223> OTHER INFORMATION: n = G, C, T or A nuclotide; k = G or T
      nucleotide

<400> SEQUENCE: 41
agtttgctgg ccatcatcca tcgcaaccag gattcaccct tggctacgcg agccaggagc      60 gactttttccg tgcttttgga tattctcacg cggctggact cgaaggcgtc ggaccaactg     120
aggnnkacgt ccactaccgt tgttggc                                          147

<210> SEQ ID NO 42
<211> LENGTH: 147
<212> TYPE: DNA
<213> ORGANISM: Hypocrea jecorina
<220> FEATURE:
<221> NAME/KEY: misc_feature
<222> LOCATION: (127)..(129)
<223> OTHER INFORMATION: n = G, C, T or A nuclotide; k = G or T
      nucleotide
```

<400> SEQUENCE: 42
agtttgctgg ccatcatcca tcgcaaccag gattcaccct tggctacgcg agccaggagc     60
gacttttccg tgctttttgga tattctcacg cggctggact cgaaggcgtc ggaccaactg    120
aggaatnnkt ccactaccgt tgttggc                                        147

<210> SEQ ID NO 43
<211> LENGTH: 156
<212> TYPE: DNA
<213> ORGANISM: Hypocrea jecorina
<220> FEATURE:
<221> NAME/KEY: misc_feature
<222> LOCATION: (97)..(105)
<223> OTHER INFORMATION: n = A, C, T or G nucleotide; k = G or T
      nucleotide; d = A, G or T nucleotide

<400> SEQUENCE: 43
agtttgctgg ccatcatcca tcgcaaccag gattcaccct tggctacgcg agccaggagc     60
gacttttccg tgctttttgga tattctcacg cggctgndtn dtnnkgactc gaaggcgtcg    120
gaccaactga ggaatacgtc cactaccgtt gttggc                               156

<210> SEQ ID NO 44
<211> LENGTH: 156
<212> TYPE: DNA
<213> ORGANISM: Hypocrea jecorina
<220> FEATURE:
<221> NAME/KEY: misc_feature
<222> LOCATION: (100)..(108)
<223> OTHER INFORMATION: n = A, C, T or G nucleotide; k = G or T
      nucleotide; d = A, G or T nucleotide

<400> SEQUENCE: 44
agtttgctgg ccatcatcca tcgcaaccag gattcaccct tggctacgcg agccaggagc     60
gacttttccg tgctttttgga tattctcacg cggctggacn dtndtnnktc gaaggcgtcg    120
gaccaactga ggaatacgtc cactaccgtt gttggc                               156

<210> SEQ ID NO 45
<211> LENGTH: 156
<212> TYPE: DNA
<213> ORGANISM: Hypocrea jecorina
<220> FEATURE:
<221> NAME/KEY: misc_feature
<222> LOCATION: (103)..(111)
<223> OTHER INFORMATION: n = A, C, T or G nucleotide; k = G or T
      nucleotide; d = A, G or T nucleotide

<400> SEQUENCE: 45
agtttgctgg ccatcatcca tcgcaaccag gattcaccct tggctacgcg agccaggagc     60
gacttttccg tgctttttgga tattctcacg cggctggact cgndtndtnn kaaggcgtcg    120
gaccaactga ggaatacgtc cactaccgtt gttggc                               156

<210> SEQ ID NO 46
<211> LENGTH: 156
<212> TYPE: DNA
<213> ORGANISM: Hypocrea jecorina
<220> FEATURE:
<221> NAME/KEY: misc_feature
<222> LOCATION: (106)..(114)
<223> OTHER INFORMATION: n = A, C, T or G nucleotide; k = G or T
      nucleotide; d = A, G or T nucleotide

<400> SEQUENCE: 46

-continued

```
agtttgctgg ccatcatcca tcgcaaccag gattcaccct tggctacgcg agccaggagc      60 gactttccg tgcttttgga tattctcacg cggctggact cgaagndtnd tnnkgcgtcg       120
gaccaactga ggaatacgtc cactaccgtt gttggc                                156

<210> SEQ ID NO 47
<211> LENGTH: 156
<212> TYPE: DNA
<213> ORGANISM: Hypocrea jecorina
<220> FEATURE:
<221> NAME/KEY: misc_feature
<222> LOCATION: (109)..(117)
<223> OTHER INFORMATION: n = A, C, T or G nucleotide; k = G or T
      nucleotide; d = A, G or T nucleotide

<400> SEQUENCE: 47
agtttgctgg ccatcatcca tcgcaaccag gattcaccct tggctacgcg agccaggagc      60 gactttccg tgcttttgga tattctcacg cggctggact cgaaggcgnd tndtnnktcg       120
gaccaactga ggaatacgtc cactaccgtt gttggc                                156

<210> SEQ ID NO 48
<211> LENGTH: 156
<212> TYPE: DNA
<213> ORGANISM: Hypocrea jecorina
<220> FEATURE:
<221> NAME/KEY: misc_feature
<222> LOCATION: (112)..(120)
<223> OTHER INFORMATION: n = A, C, T or G nucleotide; k = G or T
      nucleotide; d = A, G or T nucleotide

<400> SEQUENCE: 48
agtttgctgg ccatcatcca tcgcaaccag gattcaccct tggctacgcg agccaggagc      60 gactttccg tgcttttgga tattctcacg cggctggact cgaaggcgtc gndtndtnnk       120
gaccaactga ggaatacgtc cactaccgtt gttggc                                156

<210> SEQ ID NO 49
<211> LENGTH: 156
<212> TYPE: DNA
<213> ORGANISM: Hypocrea jecorina
<220> FEATURE:
<221> NAME/KEY: misc_feature
<222> LOCATION: (115)..(123)
<223> OTHER INFORMATION: n = A, C, T or G nucleotide; k = G or T
      nucleotide; d = A, G or T nucleotide

<400> SEQUENCE: 49
agtttgctgg ccatcatcca tcgcaaccag gattcaccct tggctacgcg agccaggagc      60 gactttccg tgcttttgga tattctcacg cggctggact cgaaggcgtc ggacndtndt       120
nnkcaactga ggaatacgtc cactaccgtt gttggc                                156

<210> SEQ ID NO 50
<211> LENGTH: 156
<212> TYPE: DNA
<213> ORGANISM: Hypocrea jecorina
<220> FEATURE:
<221> NAME/KEY: misc_feature
<222> LOCATION: (118)..(126)
<223> OTHER INFORMATION: n = A, C, T or G nucleotide; k = G or T
      nucleotide; d = A, G or T nucleotide

<400> SEQUENCE: 50
agtttgctgg ccatcatcca tcgcaaccag gattcaccct tggctacgcg agccaggagc      60 gactttccg tgcttttgga tattctcacg cggctggact cgaaggcgtc ggaccaandt       120
```

-continued

```
ndtnnkctga ggaatacgtc cactaccgtt gttggc                            156

<210> SEQ ID NO 51
<211> LENGTH: 156
<212> TYPE: DNA
<213> ORGANISM: Hypocrea jecorina
<220> FEATURE:
<221> NAME/KEY: misc_feature
<222> LOCATION: (121)..(129)
<223> OTHER INFORMATION: n = A, C, T or G nucleotide; k = G or T
      nucleotide; d = A, G or T nucleotide

<400> SEQUENCE: 51
agtttgctgg ccatcatcca tcgcaaccag gattcaccct tggctacgcg agccaggagc     60
gacttttccg tgcttttgga tattctcacg cggctggact cgaaggcgtc ggaccaactg    120
ndtndtnnka ggaatacgtc cactaccgtt gttggc                            156

<210> SEQ ID NO 52
<211> LENGTH: 156
<212> TYPE: DNA
<213> ORGANISM: Hypocrea jecorina
<220> FEATURE:
<221> NAME/KEY: misc_feature
<222> LOCATION: (124)..(132)
<223> OTHER INFORMATION: n = A, C, T or G nucleotide; k = G or T
      nucleotide; d = A, G or T nucleotide

<400> SEQUENCE: 52
agtttgctgg ccatcatcca tcgcaaccag gattcaccct tggctacgcg agccaggagc     60
gacttttccg tgcttttgga tattctcacg cggctggact cgaaggcgtc ggaccaactg    120
aggndtndtn nkaatacgtc cactaccgtt gttggc                            156

<210> SEQ ID NO 53
<211> LENGTH: 156
<212> TYPE: DNA
<213> ORGANISM: Hypocrea jecorina
<220> FEATURE:
<221> NAME/KEY: misc_feature
<222> LOCATION: (127)..(135)
<223> OTHER INFORMATION: n = A, C, T or G nucleotide; k = G or T
      nucleotide; d = A, G or T nucleotide

<400> SEQUENCE: 53
agtttgctgg ccatcatcca tcgcaaccag gattcaccct tggctacgcg agccaggagc     60
gacttttccg tgcttttgga tattctcacg cggctggact cgaaggcgtc ggaccaactg    120
aggaatndtn dtnnkacgtc cactaccgtt gttggc                            156

<210> SEQ ID NO 54
<211> LENGTH: 156
<212> TYPE: DNA
<213> ORGANISM: Hypocrea jecorina
<220> FEATURE:
<221> NAME/KEY: misc_feature
<222> LOCATION: (130)..(138)
<223> OTHER INFORMATION: n = A, C, T or G nucleotide; k = G or T
      nucleotide; d = A, G or T nucleotide

<400> SEQUENCE: 54
agtttgctgg ccatcatcca tcgcaaccag gattcaccct tggctacgcg agccaggagc     60
gacttttccg tgcttttgga tattctcacg cggctggact cgaaggcgtc ggaccaactg    120
aggaatacgn dtndtnnktc cactaccgtt gttggc                            156
```

-continued

```
<210> SEQ ID NO 55
<211> LENGTH: 138
<212> TYPE: DNA
<213> ORGANISM: Hypocrea jecorina

<400> SEQUENCE: 55
agtttgctgg ccatcatcca tcgcaaccag gattcaccct tggctacgcg agccaggagc      60 gactttttccg tgcttttgga tattctcacg cggctggcgt cggaccaact gaggaatacg     120
tccactaccg ttgttggc                                                    138

<210> SEQ ID NO 56
<211> LENGTH: 138
<212> TYPE: DNA
<213> ORGANISM: Hypocrea jecorina

<400> SEQUENCE: 56
agtttgctgg ccatcatcca tcgcaaccag gattcaccct tggctacgcg agccaggagc      60 gactttttccg tgcttttgga tattctcacg cggctggact cggaccaact gaggaatacg     120
tccactaccg ttgttggc                                                    138

<210> SEQ ID NO 57
<211> LENGTH: 138
<212> TYPE: DNA
<213> ORGANISM: Hypocrea jecorina

<400> SEQUENCE: 57
agtttgctgg ccatcatcca tcgcaaccag gattcaccct tggctacgcg agccaggagc      60 gactttttccg tgcttttgga tattctcacg cggctggact cggaccaact gaggaatacg     120
tccactaccg ttgttggc                                                    138

<210> SEQ ID NO 58
<211> LENGTH: 138
<212> TYPE: DNA
<213> ORGANISM: Hypocrea jecorina

<400> SEQUENCE: 58
agtttgctgg ccatcatcca tcgcaaccag gattcaccct tggctacgcg agccaggagc      60 gactttttccg tgcttttgga tattctcacg cggctggact cgaagcaact gaggaatacg     120
tccactaccg ttgttggc                                                    138

<210> SEQ ID NO 59
<211> LENGTH: 138
<212> TYPE: DNA
<213> ORGANISM: Hypocrea jecorina

<400> SEQUENCE: 59
agtttgctgg ccatcatcca tcgcaaccag gattcaccct tggctacgcg agccaggagc      60 gactttttccg tgcttttgga tattctcacg cggctggact cgaaggcgct gaggaatacg     120
tccactaccg ttgttggc                                                    138

<210> SEQ ID NO 60
<211> LENGTH: 138
<212> TYPE: DNA
<213> ORGANISM: Hypocrea jecorina

<400> SEQUENCE: 60
agtttgctgg ccatcatcca tcgcaaccag gattcaccct tggctacgcg agccaggagc      60
```

-continued

```
gactttttccg tgctttttgga tattctcacg cggctggact cgaaggcgtc gaggaatacg      120
tccactaccg ttgttggc                                                     138

<210> SEQ ID NO 61
<211> LENGTH: 138
<212> TYPE: DNA
<213> ORGANISM: Hypocrea jecorina

<400> SEQUENCE: 61
agtttgctgg ccatcatcca tcgcaaccag gattcaccct tggctacgcg agccaggagc       60 gactttttccg tgctttttgga tattctcacg cggctggact cgaaggcgtc ggacaatacg      120
tccactaccg ttgttggc                                                     138

<210> SEQ ID NO 62
<211> LENGTH: 138
<212> TYPE: DNA
<213> ORGANISM: Hypocrea jecorina

<400> SEQUENCE: 62
agtttgctgg ccatcatcca tcgcaaccag gattcaccct tggctacgcg agccaggagc       60 gactttttccg tgctttttgga tattctcacg cggctggact cgaaggcgtc ggaccaaacg      120
tccactaccg ttgttggc                                                     138

<210> SEQ ID NO 63
<211> LENGTH: 138
<212> TYPE: DNA
<213> ORGANISM: Hypocrea jecorina

<400> SEQUENCE: 63
agtttgctgg ccatcatcca tcgcaaccag gattcaccct tggctacgcg agccaggagc       60 gactttttccg tgctttttgga tattctcacg cggctggact cgaaggcgtc ggaccaactg      120
tccactaccg ttgttggc                                                     138

<210> SEQ ID NO 64
<211> LENGTH: 138
<212> TYPE: DNA
<213> ORGANISM: Hypocrea jecorina

<400> SEQUENCE: 64
agtttgctgg ccatcatcca tcgcaaccag gattcaccct tggctacgcg agccaggagc       60 gactttttccg tgctttttgga tattctcacg cggctggact cgaaggcgtc ggaccaactg      120
aggactaccg ttgttggc                                                     138

<210> SEQ ID NO 65
<211> LENGTH: 138
<212> TYPE: DNA
<213> ORGANISM: Hypocrea jecorina

<400> SEQUENCE: 65
agtttgctgg ccatcatcca tcgcaaccag gattcaccct tggctacgcg agccaggagc       60 gactttttccg tgctttttgga tattctcacg cggctggact cgaaggcgtc ggaccaactg      120
aggaataccg ttgttggc                                                     138

<210> SEQ ID NO 66
<211> LENGTH: 159
<212> TYPE: DNA
```

-continued

<213> ORGANISM: Hypocrea jecorina

<400> SEQUENCE: 66

```
agtttgctgg ccatcatcca tcgcaaccag gattcaccct tggctacgcg agccaggagc       60
gacttttccg tgctttttgga tattctcacg cggctggact cgaaggcgtc ggacggcaag      120
cccatcccca accccctcct cggcctcgac agcacctaa                              159
```

<210> SEQ ID NO 67
<211> LENGTH: 52
<212> TYPE: PRT
<213> ORGANISM: Hypocrea jecorina

<400> SEQUENCE: 67

```
Ser Leu Leu Ala Ile Ile His Arg Asn Gln Asp Ser Pro Leu Ala Thr
1               5                   10                  15

Arg Ala Arg Ser Asp Phe Ser Val Leu Leu Asp Ile Leu Thr Arg Leu
            20                  25                  30

Asp Ser Lys Ala Ser Asp Gly Lys Pro Ile Pro Asn Pro Leu Leu Gly
        35                  40                  45

Leu Asp Ser Thr
    50
```

<210> SEQ ID NO 68
<211> LENGTH: 186
<212> TYPE: DNA
<213> ORGANISM: Hypocrea jecorina

<400> SEQUENCE: 68

```
agtttgctgg ccatcatcca tcgcaaccag gattcaccct tggctacgcg agccaggagc       60
gacttttccg tgctttttgga tattctcacg cggctggact cgaaggcgtc ggacggcaag      120
cccatcccca accccctcct cggcctcgac agcacccgca ccggccacca ccaccaccac      180
cactaa                                                                  186
```

<210> SEQ ID NO 69
<211> LENGTH: 61
<212> TYPE: PRT
<213> ORGANISM: Hypocrea jecorina

<400> SEQUENCE: 69

```
Ser Leu Leu Ala Ile Ile His Arg Asn Gln Asp Ser Pro Leu Ala Thr
1               5                   10                  15

Arg Ala Arg Ser Asp Phe Ser Val Leu Leu Asp Ile Leu Thr Arg Leu
            20                  25                  30

Asp Ser Lys Ala Ser Asp Gly Lys Pro Ile Pro Asn Pro Leu Leu Gly
        35                  40                  45

Leu Asp Ser Thr Arg Thr Gly His His His His His His
    50                  55                  60
```

<210> SEQ ID NO 70
<211> LENGTH: 23
<212> TYPE: RNA
<213> ORGANISM: Hypocrea jecorina

<400> SEQUENCE: 70

```
cgagcagcac cgcagucgac agg                                                23
```

COMPOSITIONS AND METHODS FOR ENHANCED PROTEIN PRODUCTION IN FILAMENTOUS FUNGAL CELLS

CROSS REFERENCE TO RELATED APPLICATIONS

The present application is a U.S. National Stage Application under 35 U.S.C. § 371 of International Application No. PCT/US2021/026551, filed Apr. 9, 2021, which claims priority to U.S. Provisional Patent Application No. 63/013,741, filed Apr. 22, 2020, all of which are incorporated herein by reference in their entirety.

FIELD

The present disclosure is generally related to the fields of molecular biology, biochemistry, industrial fermentation, protein production, filamentous fungi and the like. Certain embodiments of the disclosure are therefore related to mutant and/or genetically modified filamentous fungal cells and methods thereof for use in the production of proteins of interest.

SEQUENCE LISTING

The sequence listing text file submitted herewith contains the file "NB41754WOPCT_SequenceListing.txt" created on Mar. 22, 2021, which is 136 kilobytes in size. This sequence listing complies with 37 C.F.R. § 1.52(e) and is incorporated herein by reference in its entirety.

BACKGROUND

Cellulose, a component of lignocellulosic plant material, is the most abundant polysaccharide found in nature. Likewise, filamentous fungi are known in the art to be efficient degraders of plant biomass, and are in fact a major source of industrially relevant lignocellulosic degrading enzymes (referred to hereinafter collectively as "cellulase" enzymes). For example, filamentous fungi are known to produce extracellular cellulase enzymes (e.g., cellobiohydrolases, endoglucanases, β-glucosidases) that hydrolyze the β-(1,4)-linked glycosidic bonds of cellulose to produce glucose (i.e., thereby conferring the ability of these filamentous fungi to utilize cellulose for growth). In particular, the filamentous fungus *Trichoderma reesei* (*T. reesei*; an anamorph of the fungus *Hypocrea jecorina*) is known to be an efficient producer of cellulase enzymes (e.g., see PCT International Application No: WO1998/15619, WO2005/028636, WO2006/074005, WO1992/06221, WO1992/06209, WO1992/06183, WO2002/12465 and the like), and as such, filamentous fungi have been utilized for their ability to produce enzymes which are valuable in the production of such commodities as cellulosic derived ethanol, textiles and clothing, detergents, fibers, food and feed additives and other industrial uses.

The expression/production of these industrially relevant enzymes in *Trichoderma* sp. fungal cells are known to be dependent on the carbon source available for growth. The expression/production of cellulase enzymes by filamentous fungi is an energy consuming process and as such, both inducing and repressing mechanisms have evolved to ensure the efficient production of these enzymes. For example, the various genes encoding enzymes needed for the degradation of plant cell wall material (i.e., lignocellulosic degrading enzymes; e.g., cellulases/hemicellulases) are "activated" in the presence of an "inducing" substrate and "repressed" in the presence of easily metabolized carbon sources (e.g., D-glucose) that are preferred over plant biomass via a mechanism known as "carbon catabolite repression" ("CCR"). Thus, the cellulase genes are tightly repressed by glucose and are induced several thousand folds by cellulose and certain disaccharides (e.g., sophorose, lactose, gentibiose). For example, the expression level of the major cellobiohydrolase 1 (cbh1) is "up-regulated" several thousand fold on media containing inducing carbon sources such as cellulose or sophorose, compared with glucose containing media (Ilmen et al., 1997).

In general, the commercial scale production of enzymes/polypeptides by filamentous fungi such as *Trichoderma* is typically by either solid or submerged culture, including batch, fed batch, and continuous flow processes. For example, one of the most problematic and expensive aspects of industrial cellulase production in *Trichoderma* is providing the appropriate inducer (i.e., inducing substrate) to the *Trichoderma* sp. host cells. For example, as is the case for laboratory scale experiments, cellulase (enzyme) production on a commercial scale is "induced" by growing the fungal cells on solid cellulose (i.e., an inducing substrate) or by culturing the cells in the presence of a disaccharide inducer such as "lactose" (i.e., an inducing substrate).

Unfortunately, on an industrial scale, both methods of "induction" have drawbacks which result in high costs being associated with cellulase production, and as such, there remain ongoing and unmet needs in the art for cost effective commercial scale production of enzymes/polypeptides by filamentous fungi, without the need or requirement of providing costly inducing substrates (e.g., sophorose, lactose and the like) for such production. As described and exemplified herein, the mutant and/or modified fungal cells (strains) of the disclosure are well-suited for use in industrial scale fermentation processes for the enhanced expression/production of proteins of interest in the presence or in the absence of an inducing substrate.

SUMMARY

Certain embodiments of the disclosure are related to mutant and genetically modified *Trichoderma* sp. fungal cells for use in the commercial scale production of polypeptides. More particularly, certain embodiments of the disclosure are related to novel variant Ace3 transcription factor (TF) proteins capable of upregulating the expression of one or more genes encoding one or more lignocellulosic degrading enzymes. Certain other embodiments are therefore directed to polynucleotides (nucleic acid sequences) encoding such novel (i.e., variant) Ace3 transcription factor (TF) proteins disclosed herein. Certain other embodiments are related to compositions and methods for constructing, modifying testing, screening, isolating and the like *Trichoderma* sp. cells (strains) comprising and expressing a variant Ace3 transcription factor (TF) proteins disclosed herein.

Thus, certain embodiments of the disclosure are directed to an isolated polynucleotide encoding a variant Ace3 TF protein, wherein the variant Ace3 TF comprises at least 90% sequence identity to amino acid positions 1-672 of SEQ ID NO: 2 and comprises a genetic modification of one or more C-terminal amino acid residues selected from positions 673-689 of SEQ ID NO: 2. In related embodiments, the polynucleotide encodes a variant Ace3 TF comprising a functional N-terminal binuclear zinc cluster ($Zn_2Cys_6$) DNA binding domain comprising at least 90% sequence identity to SEQ ID NO: 29. In other embodiments, the genetic modification of one or more C-terminal amino acid residues selected from positions 673-689 of SEQ ID NO: 2 comprises an amino acid deletion, an amino acid insertion, an amino acid substitution, or a combination thereof.

In certain other embodiments of the polynucleotide, the genetic modification of one or more C-terminal amino acid residues comprises a deletion of at least the last seven (7) C-terminal amino acid positions 683-689 of SEQ ID NO: 2, a deletion of at least the last eight (8) C-terminal amino acid positions 682-689 of SEQ ID NO: 2, a deletion of at least the last nine (9) C-terminal amino acid positions 681-689 of SEQ ID NO: 2, a deletion of at least the last ten (10) C-terminal amino acid positions 680-689 of SEQ ID NO: 2, a deletion of at least the last eleven (11) C-terminal amino acid positions 679-689 of SEQ ID NO: 2, a deletion of at least the last twelve (12) C-terminal amino acid positions 678-689 of SEQ ID NO: 2, a deletion of at least the last thirteen (13) C-terminal amino acid positions 677-689 of SEQ ID NO: 2, a deletion of at least the last fourteen (14) C-terminal amino acid positions 676-689 of SEQ ID NO: 2, a deletion of at least the last fifteen (15) C-terminal amino acid positions 675-689 of SEQ ID NO: 2, a deletion of at least the last sixteen (16) C-terminal amino acid positions 674-689 of SEQ ID NO: 2 or a deletion of at least the last seventeen (17) C-terminal amino acid positions 673-689 of SEQ ID NO: 2.

In certain embodiments, an isolated polynucleotide of the disclosure encodes a variant Ace3 TF comprising at least 90% sequence identity to an amino acid sequence selected from any one of SEQ ID NO: 9 through SEQ ID NO: 18.

Certain other embodiments of the disclosure are related to an isolated *Trichoderma* sp. mutant cell comprising a mutated ace3 gene encoding a variant Ace3 transcription factor (TF) protein, wherein the variant Ace3 TF protein comprises at least 90% sequence identity to amino acid positions 1-672 of SEQ ID NO: 2 and comprises one or more mutated C-terminal amino acid residues selected from positions 673-689 of SEQ ID NO:2. In certain embodiments, the variant Ace3 TF protein of the mutant cell upregulates the expression of a gene encoding a lignocellulosic degrading enzyme in the absence of an inducing substrate, when the mutant cell is fermented under suitable conditions for the production of a lignocellulosic degrading enzyme.

Certain other embodiments of the disclosure are related to a genetically modified *Trichoderma* sp. fungal cell derived from a parental *Trichoderma* sp. cell comprising an ace3 gene encoding an Ace3 transcription factor (TF) protein comprising at least 90% sequence identity to SEQ ID NO: 2, wherein the genetically modified cell comprises a modified ace3 gene encoding a variant Ace3 TF protein comprising at least 90% sequence identity to amino acid positions 1-672 of SEQ ID NO: 2 and comprising a genetic modification of one or more C-terminal amino acid residues selected from positions 673-689 of SEQ ID NO: 2.

Certain other embodiments of the disclosure are related to a genetically modified *Trichoderma* sp. fungal cell derived from a parental *Trichoderma* sp. cell comprising a mutated ace3 gene encoding a variant Ace3 transcription factor (TF) protein comprising at least 90% sequence identity to SEQ ID NO: 4, wherein the N-terminus of SEQ ID NO: 4 does not comprise an intact binuclear zinc (Zn$_2$Cys$_6$) DNA binding set forth in SEQ ID NO: 29, wherein the genetically modified cell comprises a modified ace3 gene encoding a variant Ace3 TF protein comprising at least 90% sequence identity to positions 1-672 of SEQ ID NO: 2, wherein the N-terminus of SEQ ID NO: 2 comprises an intact binuclear zinc (Zn$_2$Cys$_6$) DNA binding set forth in SEQ ID NO: 29 and comprises a genetic modification of one or more C-terminal amino acid residues selected from positions 673-689 of SEQ ID NO: 2.

In certain other embodiments, the disclosure is related to methods of screening for variant Ace3 TF proteins which induce the expression of a gene encoding a lignocellulosic degrading enzyme in the absence of an inducing substrate. In other embodiments, the disclosure provides methods of screening for variant Ace3 TF proteins which induce the expression of a gene encoding a reporter protein in the absence of an inducing substrate. In other embodiments, the disclosure is directed to methods for producing a lignocellulosic degrading enzyme in a *Trichoderma* sp. fungal cell in the absence of an inducing substrate. In certain other embodiments, the disclosure is related to methods for producing a protein of interest (POI) in a *Trichoderma* sp. cell in the absence of an inducing substrate.

BRIEF DESCRIPTION OF THE DRAWINGS

FIG. 1 presents an amino acid sequence alignment of the Ace3-S protein (SEQ ID NO: 4), the Ace3-L protein (SEQ ID NO: 6) and the Ace3-LC protein (SEQ ID NO: 2). As shown in FIG. 1A, the six (6) N-terminal cysteine amino acids of the binuclear zinc cluster (Zn$_2$Cys$_6$) DNA binding domain are indicated with grey shadowed cysteines (C). As presented in FIG. 1A, the Ace3-S protein (SEQ ID NO: 4) comprises a truncated N-terminus, wherein two (2) of the six (6) cysteine residues of the zinc (Zn$_2$Cys$_6$) DNA binding domain are missing (deleted) relative to the N-terminus of the Ace3-L and Ace3-LC proteins. Likewise, as shown in FIG. 1B, the C-terminus of the Ace3-L protein is truncated relative to the Ace3-S and Ace3-LC proteins, which comprise a wild-type C-terminus ending in glycine (G), relative to the truncated C-terminus of the Ace3-L protein ending in aspartic acid (D).

FIG. 2 shows the amino acid sequence of the Ace3-LC protein (FIG. 2A; SEQ ID NO: 2) comprising six-hundred eighty-nine (689) amino acid residues and a wild-type C-terminus ending in a glycine (G) at position 689. In addition, FIG. 2 shows the amino acid sequences of sixteen (16) different Ace3 proteins comprising incremental C-terminal truncations (i.e., relative to the wild-type Ace3-LC protein's C-terminus; SEQ ID NO: 2). As presented in FIG. 2, the Ace3 C-term-5 protein (FIG. 2A; SEQ ID NO: 7) comprises six-hundred eighty-four (684) amino acid residues and a five (5) amino acid truncation at the C-terminus ending in serine (S) at position 684 (relative to WT Ace3 C-terminus; SEQ ID NO: 2), the Ace3 C-term-6 protein (FIG. 2A; SEQ ID NO: 8) comprises six-hundred eighty-three (683) amino acid residues and a six (6) amino acid truncation at the C-terminus ending in threonine (T) at position 683 (relative to WT Ace3 C-terminus; SEQ ID NO: 2), the Ace3 C-term-7 protein (FIG. 2B; SEQ ID NO: 9) comprises six-hundred eighty-two (682) amino acid residues with a seven (7) amino acid truncation at the C-terminus ending in asparagine (N) at position 682 (relative to WT Ace3 C-terminus; SEQ ID NO: 2), the Ace3 C-term-8 protein (FIG. 2B; SEQ ID NO: 10) comprises six-hundred eighty-one (681) amino acid residues with an eight (8) amino acid truncation at the C-terminus ending in arginine (R) at position 681 (relative to WT Ace3 C-terminus; SEQ ID NO: 2), the Ace3 C-term-9 protein (FIG. 2B; SEQ ID NO: 11) comprises six-hundred eighty (680) amino acid residues with a nine (9) amino acid truncation at the C-terminus ending in leucine (L) at position 680 (relative to WT Ace3 C-terminus; SEQ ID NO: 2), the Ace3 C-term-10

5

Figure 6:
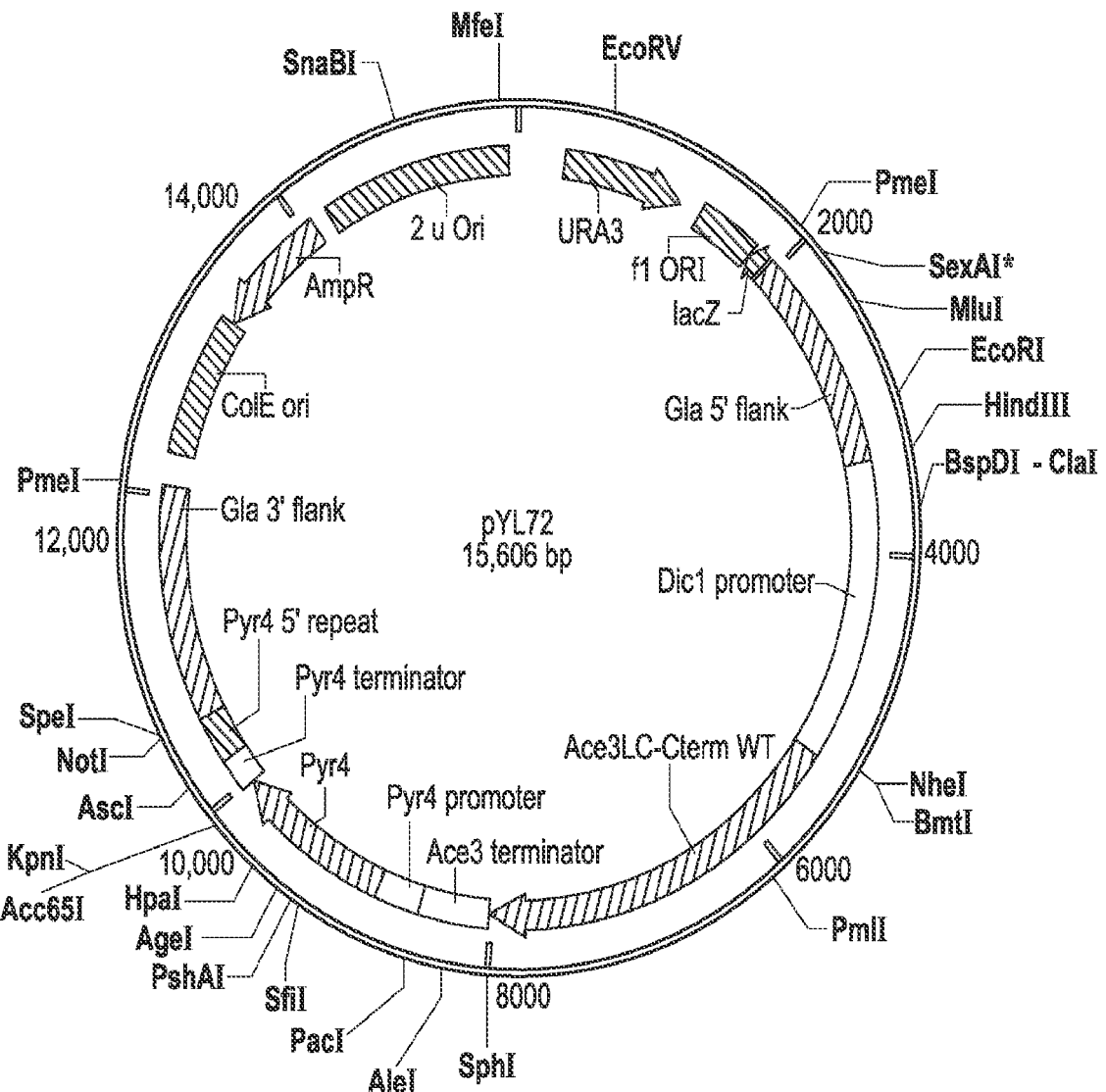

6 protein (FIG. 2C; SEQ ID NO: 12) comprises six-hundred seventy-nine (679) amino acid residues with a ten (10) amino acid truncation at the C-terminus ending in glutamine (Q) at position 679 (relative to WT Ace3 C-terminus; SEQ ID NO: 2), the Ace3 C-term-12 protein (FIG. 2C; SEQ ID NO: 13) comprises six-hundred seventy-seven (677) amino acid residues with atwelve (12) amino acid truncation at the C-terminus ending in serine (S) at position 677 (relative to WT Ace3 C-terminus; SEQ ID NO: 2), the Ace3 C-term-13 protein (FIG. 2C; SEQ ID NO: 14) comprises six-hundred seventy-six (676) amino acid residues with a thirteen (13) amino acid truncation at the C-terminus ending in alanine (A) at position 676 (relative to WT Ace3 C-terminus; SEQ ID NO: 2), the Ace3 C-term-14 protein (FIG. 2D; SEQ ID NO: 15) comprises six-hundred seventy-five (675) amino acid residues with a fourteen (14) amino acid truncation at the C-terminus ending in lysine (K) at position 675 (relative to WT Ace3 C-terminus; SEQ ID NO: 2), the Ace3 C-term-15 protein (FIG. 2D; SEQ ID NO: 16) comprises six-hundred seventy-four (674) amino acid residues with a fifteen (15) amino acid truncation at the C-terminus ending in serine (S) at position 674 (relative to WT Ace3 C-terminus; SEQ ID NO: 2), the Ace3 C-term-16 protein (FIG. 2D; SEQ ID NO: 17) comprises six-hundred seventy-three (673) amino acid residues with a sixteen (16) amino acid truncation at the C-terminus ending in aspartic acid (D) at position 673 (relative to WT Ace3 C-terminus; SEQ ID NO: 2), the Ace3 C-term-17 protein (FIG. 2E; SEQ ID NO: 18) comprises six-hundred seventy-two (672) amino acid residues with a seventeen (17) amino acid truncation at the C-terminus ending in leucine (L) at position 672 (relative to WT Ace3 C-terminus; SEQ ID NO: 2), the Ace3 C-term-18 protein (FIG. 2E; SEQ ID NO: 19) comprises six-hundred seventy-one (671) amino acid residues with an eighteen (18) amino acid truncation at the C-terminus ending in arginine (R) at position 671 (relative to WT Ace3 C-terminus; SEQ ID NO: 2), the Ace3 C-term-19 protein (FIG. 2E; SEQ ID NO: 20) comprises six-hundred seventy (670) amino acid residues with a nineteen (19) amino acid truncation at the C-terminus ending in threonine (T) at position 670 (relative to WT Ace3 C-terminus; SEQ ID NO: 2), the Ace3 C-term-20 protein (FIG. 2F; SEQ ID NO: 21) comprises six-hundred sixty-nine (669) amino acid residues with a twenty (20) amino acid truncation at the C-terminus ending in leucine (L) at position 669 (relative to WT Ace3 C-terminus; SEQ ID NO: 2) and the Ace3 C-term-25 protein (FIG. 2F; SEQ ID NO: 22) comprises six-hundred sixty-four (664) amino acid residues with a twenty-five (25) amino acid truncation at the C-terminus ending in valine (V) at position 664 (relative to WT Ace3 C-terminus; SEQ ID NO: 2).

FIG. 3 shows the amino acid sequence of the Ace3 binuclear zinc cluster ($Zn_2Cys_6$) DNA binding domain (SEQ ID NO: 29), which comprises six (6) cysteine (C) residues (shown with bold and underlined C residues), wherein the DNA binding domain is located within amino acid positions 73-109 of the Ace3-LC protein (SEQ ID NO: 2) and Ace3-L (SEQ ID NO: 6) protein.

FIG. 4 shows the wild-type C-terminus of the Ace3-LC protein (e.g., SEQ ID NO: 2) ending in glycine (G) at amino acid position six-hundred eight-nine (689). As presented in FIG. 4, the C-terminal amino acids shown in bold text have been assigned negative numbers, wherein the most C-terminal amino acid position (i.e., glycine (G); position 689) is assigned a negative one (−1), the threonine (T) at position 685 is assigned a negative five (−5), the leucine (L) at position 680 is assigned a negative ten (−10), etc. As generally described in the Examples and Detailed Description herewith, the C-terminal amino acid region of the Ace3 protein presented in FIG. 4 with bold C-terminal amino acids and grey shading (i.e., −7 (T) threonine to −17 (D) aspartic acid) are particularly suitable regions for genetic modification (e.g., truncations, internal deletions, insertions, substitutions and combinations thereof).

FIG. 5 presents an alignment of the Ace3-LC with wild-type C-terminus (i.e., amino acid positions 641-689; SEQ ID NO: 2), with the C-termini of the Ace3-LC C-term-7 protein (amino acid positions 641-682; SEQ ID NO: 9) and Ace3-LC C-term-17 protein (amino acid positions 641-672; SEQ ID NO:18). As presented in FIG. 5, the bold underlined C-terminal amino acid residues of the Ace3 protein (DSK-ASDQLRN) are particularly suitable regions for genetic modification (e.g., truncations, internal deletions, insertions, substitutions and combinations thereof).

FIG. 6 is a schematic map of plasmid pYL72 comprising a polynucleotide sequence encoding an Ace3 protein comprising a wild-type (i.e., full-length) C-terminus ending in Glycine (e.g., Ace3-LC protein; SEQ ID NO: 2).

Figure 7:
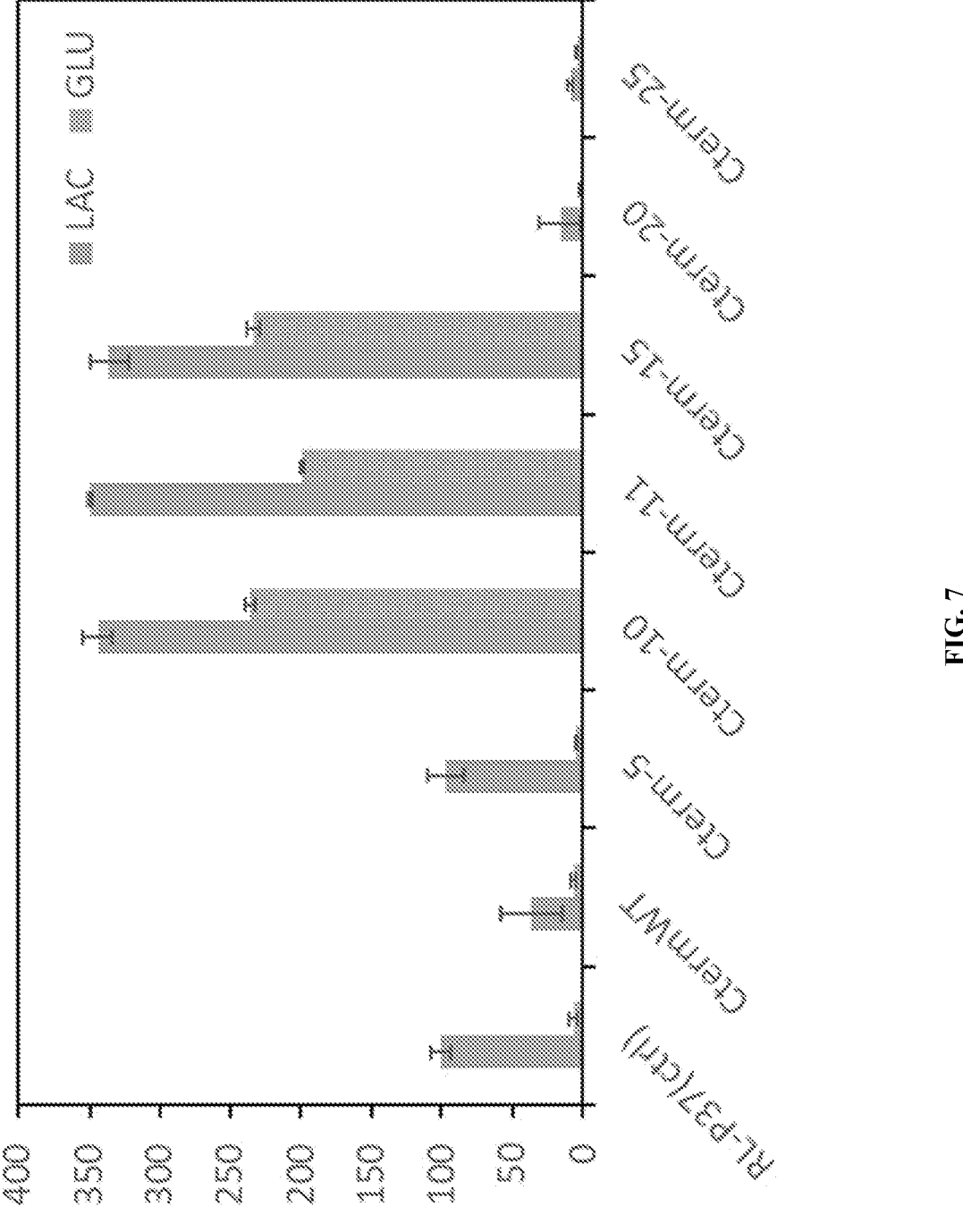

FIG. 7 shows the average total secreted protein titers of *T. reesei* strains fermented under inducing (lactose; Lac) and non-inducing (glucose; Glu) conditions. As presented in FIG. 7, the *T. reesei* strains screened included a control strain (RL-P37), a "C-term-WT" strain expressing an Ace3-LC protein comprising a wild-type C-terminus (SEQ ID NO: 2), a "C-term-5" strain expressing a variant Ace3-LC protein comprising a five (5) amino acid C-terminal truncation (SEQ ID NO: 7), a "C-term-10" strain expressing a variant Ace3-LC protein comprising a ten (10) amino acid C-terminal truncation (SEQ ID NO: 12), a "C-term-11" strain expressing a variant Ace3-LC protein comprising an eleven (11) amino acid C-terminal truncation (SEQ ID NO: 6), a "C-term-15" strain expressing a variant Ace3-LC protein comprising a fifteen (15) amino acid C-terminal truncation (SEQ ID NO: 16), a "C-term-20" strain expressing a variant Ace3-LC protein comprising a twenty (20) amino acid C-terminal truncation (SEQ ID NO: 21) and a "C-term-25" strain expressing a variant Ace3-LC protein comprising a twenty-five (25) amino acid C-terminal truncation (SEQ ID NO: 22). As indicated in FIG. 7, the parental control strain RL-P37 can only produce high amount of protein on lactose (i.e., under inducing conditions) and produced a minimal basal level of protein on glucose (i.e., under non-inducing condition). In contrast, daughter strains (cells) expressing Ace3-LC variants comprising a ten (10), eleven (11) or fifteen (15) amino acid truncation at the C-terminus (i.e., SEQ ID NO: 12, SEQ ID NO: 6 and SEQ ID NO: 16, respectively), demonstrated an increase in protein production under both lactose (inducing) and glucose (non-inducing) conditions.

Figure 8:
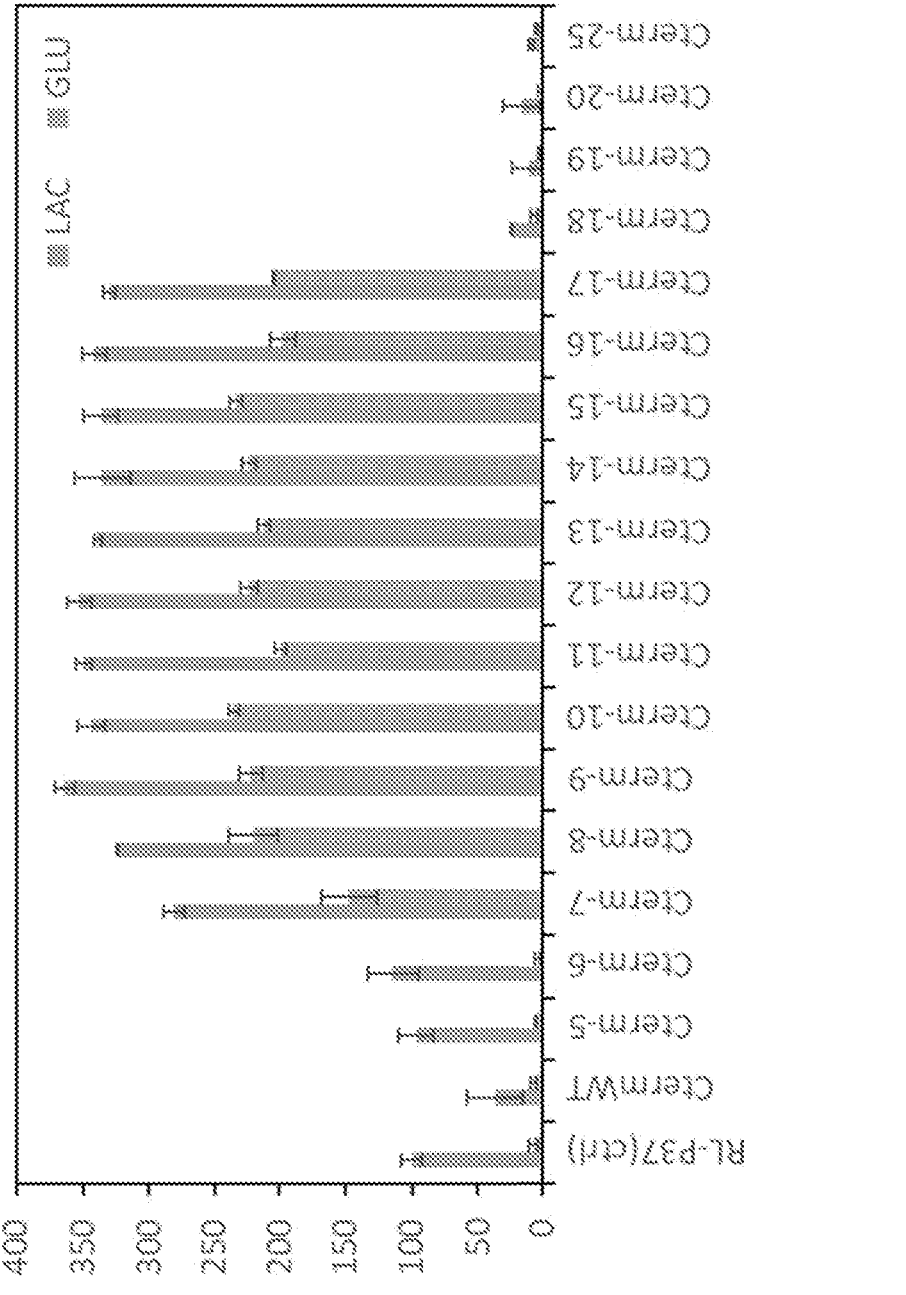

FIG. 8 shows the average total secreted protein titers and standard deviation from two (2) to four (4) biological replicates fermented under inducing (lactose; Lac) and non-inducing (glucose; Glu) conditions. As presented in FIG. 8, the *T. reesei* strains screened included a control strain (RL-P37), a "C-term-WT" strain expressing an Ace3-LC protein comprising a wild-type C-terminus (SEQ ID NO: 2), a "C-term-5" strain expressing a variant Ace3-LC protein comprising a five (5) amino acid C-terminal truncation (SEQ ID NO: 7), a "C-term-6" strain expressing a variant Ace3-LC protein comprising a six (6) amino acid C-terminal truncation (SEQ ID NO: 8), a "C-term-7" strain expressing a variant Ace3-LC protein comprising a seven (7) amino acid C-terminal truncation (SEQ ID NO: 9), a "C-term-8" strain expressing a variant Ace3-LC protein comprising an eight (8) amino acid C-terminal truncation (SEQ ID NO:

10), a "C-term-9" strain expressing a variant Ace3-LC protein comprising a nine (9) amino acid C-terminal truncation (SEQ ID NO: 11), a "C-term-10" strain expressing a variant Ace3-LC protein comprising a ten (10) amino acid C-terminal truncation (SEQ ID NO: 12), a "C-term-11" strain expressing a variant Ace3-LC protein comprising an eleven (11) amino acid C-terminal truncation (SEQ ID NO: 6), a "C-term-12" strain expressing a variant Ace3-LC protein comprising a twelve (12) amino acid C-terminal truncation (SEQ ID NO: 13), a "C-term-13" strain expressing a variant Ace3-LC protein comprising a thirteen (13) amino acid C-terminal truncation (SEQ ID NO: 14), a "C-term-14" strain expressing a variant Ace3-LC protein comprising a fourteen (14) amino acid C-terminal truncation (SEQ ID NO: 15), a "C-term-15" strain expressing a variant Ace3-LC protein comprising a fifteen (15) amino acid C-terminal truncation (SEQ ID NO: 16), a "C-term-16" strain expressing a variant Ace3-LC protein comprising a sixteen (16) amino acid C-terminal truncation (SEQ ID NO: 17), a "C-term-17" strain expressing a variant Ace3-LC protein comprising a seventeen (17) amino acid C-terminal truncation (SEQ ID NO: 18), a "C-term-18" strain expressing a variant Ace3-LC protein comprising an eighteen (18) amino acid C-terminal truncation (SEQ ID NO: 19), a "C-term-19" strain expressing a variant Ace3-LC protein comprising a nineteen (19) amino acid C-terminal truncation (SEQ ID NO: 20), a "C-term-20" strain expressing a variant Ace3-LC protein comprising a twenty (20) amino acid C-terminal truncation (SEQ ID NO: 21) and a "C-term-25" strain expressing a variant Ace3-LC protein comprising a twenty-five (25) amino acid C-terminal truncation (SEQ ID NO: 22).

Figure 9:
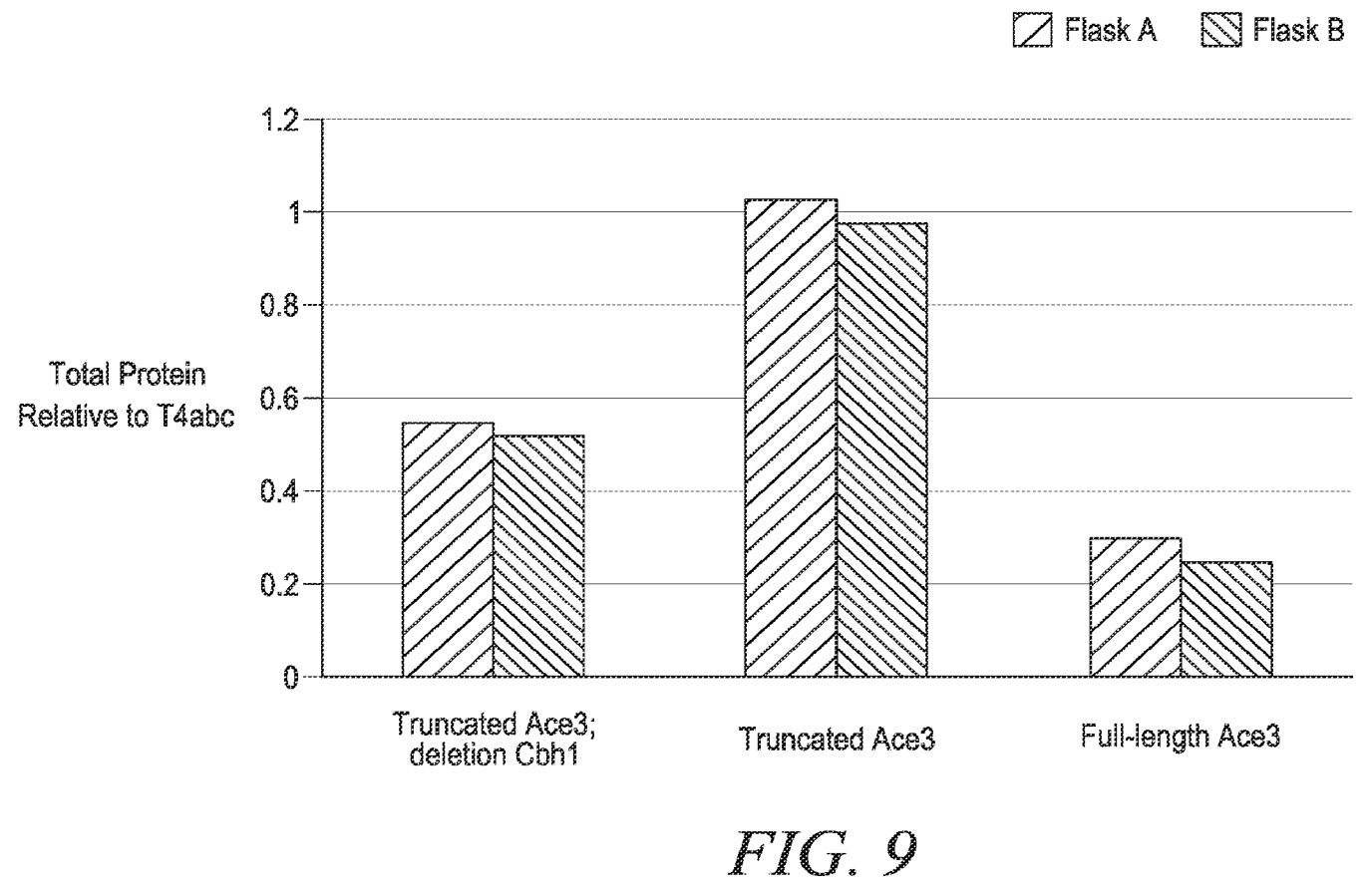

FIG. 9 shows total secreted protein titers from strains T4abc (comprising the ace3 truncation allele encoding an Ace3 protein of SEQ ID NO: 6), T4abc ace3_rev (comprising the reverted ace3 allele encoding an Ace3 protein having a wild-type (full-length C-terminus; SEQ ID NO: 2), and T4abc del-cbh1 (comprising a deletion of the cbh1 (cellobiohydrolase) gene), wherein each strain was evaluated in two (2) independent shake flasks (e.g., Flask A and Flask B). As shown in FIG. 9, the total secreted protein titer decreased 73% when the ace3 mutation was reverted in the T4abc background, such that it encoded the full-length Ace3, relative to the T4abc parental strain which encoded the truncated version of Ace3.

Figure 10:
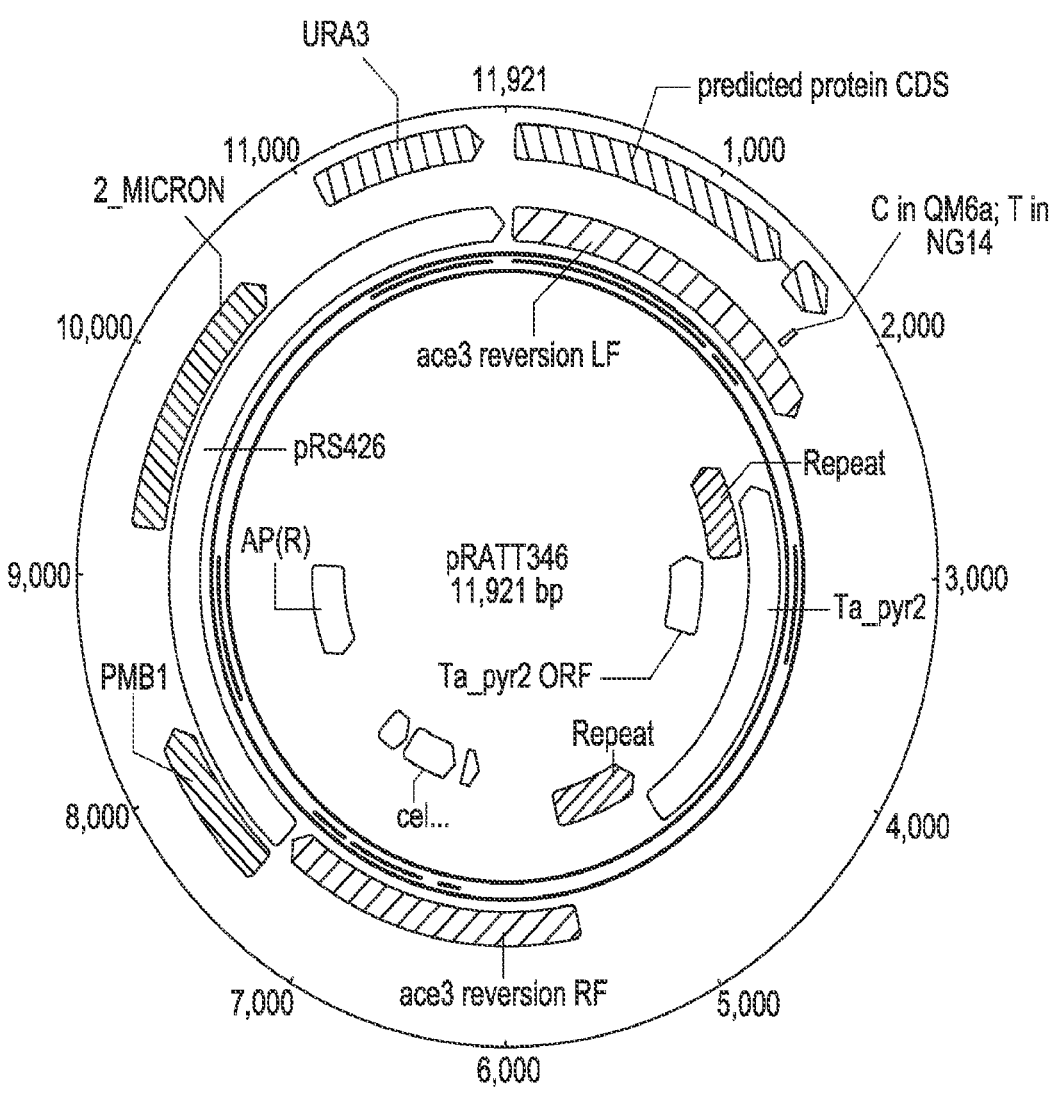

FIG. 10 is a schematic map of the ace3 reversion cassette plasmid named pRATT346.

Figure 11:
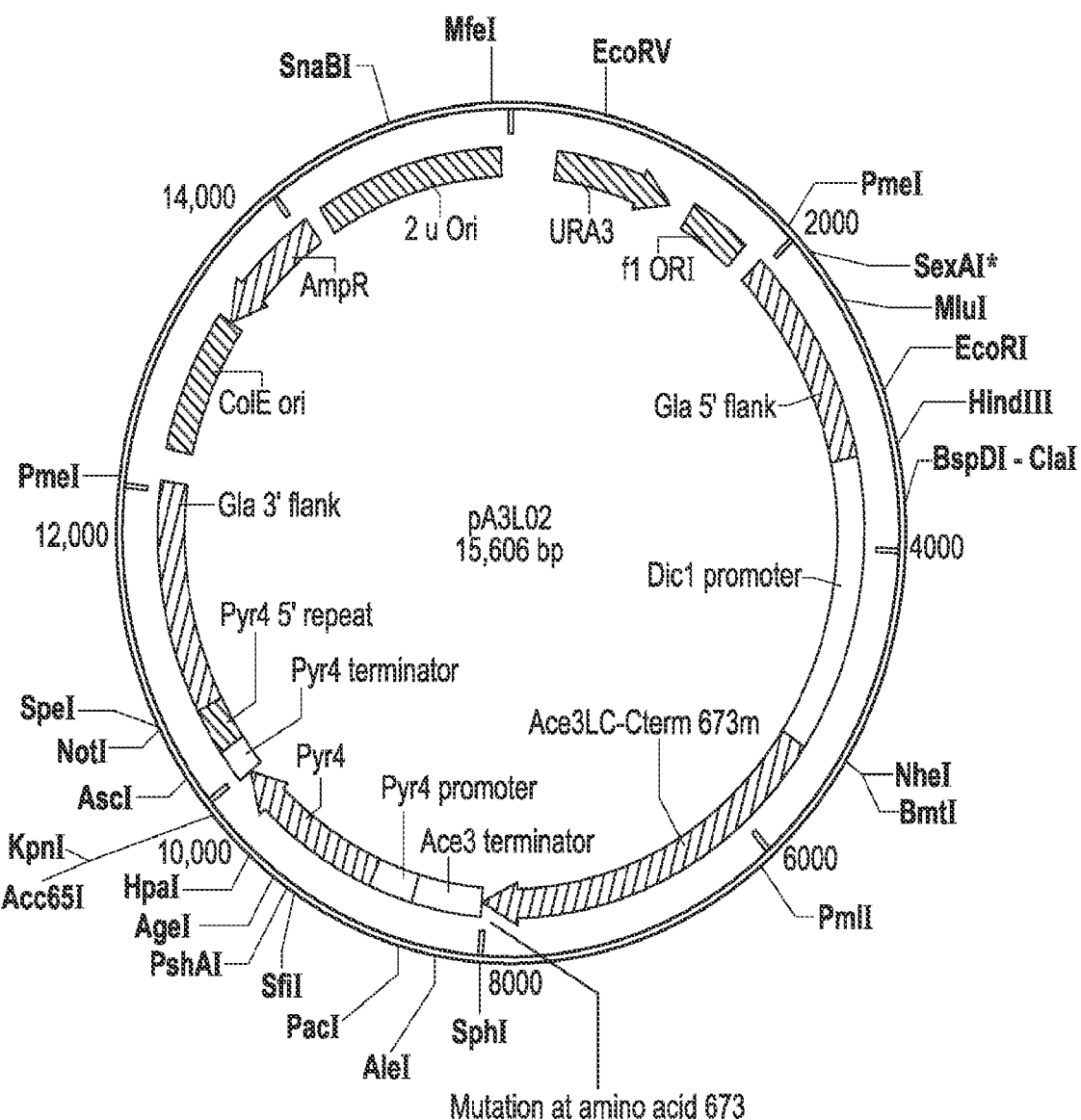

FIG. 11 is a schematic map of plasmid pA3L02 comprising a polynucleotide sequence encoding a variant Ace3-LC protein harboring a mutation at amino acid position 673 (SEQ ID NO: 32).

FIG. 12 presents an amino acid sequence alignment of the native Ace3-LC C-terminus (FIG. 12; Ace3-LC amino acid residue positions 641 through 689; SEQ ID NO: 2) aligned with the C-terminus of Ace3-L (FIG. 12; Ace3-L positions 641 through 678; SEQ ID NO: 6), Ace3-LC-V5 (FIG. 12; Ace3-LC-V5 positions 641 through 692; SEQ ID NO: 67) and Ace3-LC-V5 (6×His) (FIG. 12; Ace3-LC-V5(6×His) positions 642-701; SEQ ID NO: 69). As shown in FIG. 12, the V5 tag is indicated with bold amino acids residues and the six (6) histidine (His) tag is indicated with underlined H amino acids residues, which are separated by a three (3) amino acid "RTG" linker sequence.

Figure 13:
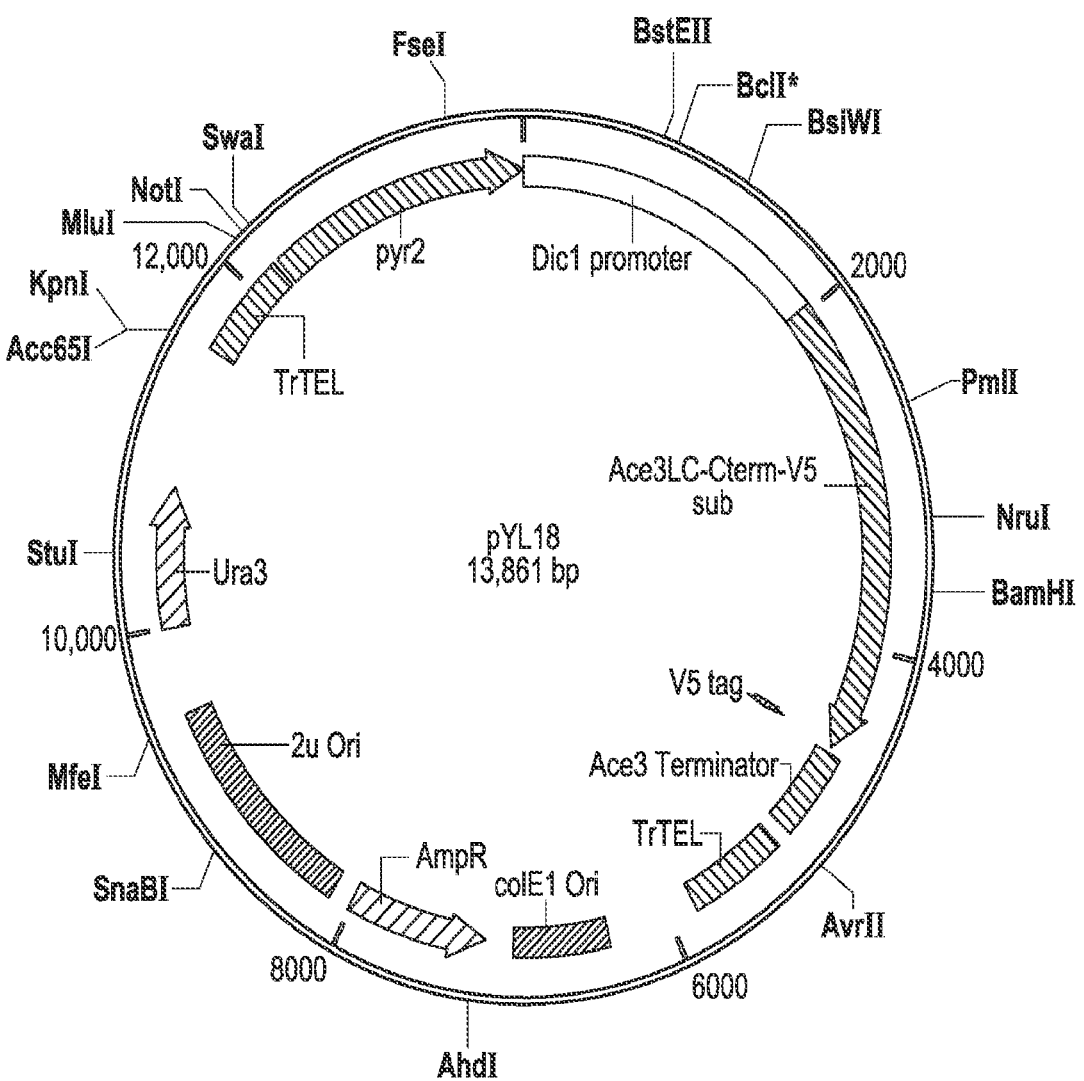

FIG. 13 is a schematic map of plasmid pYL18 comprising a polynucleotide sequence encoding a variant Ace3-LC protein harboring C-terminal amino acid substitution with an V5 epitope tag (SEQ ID NO: 67).

Figure 14:
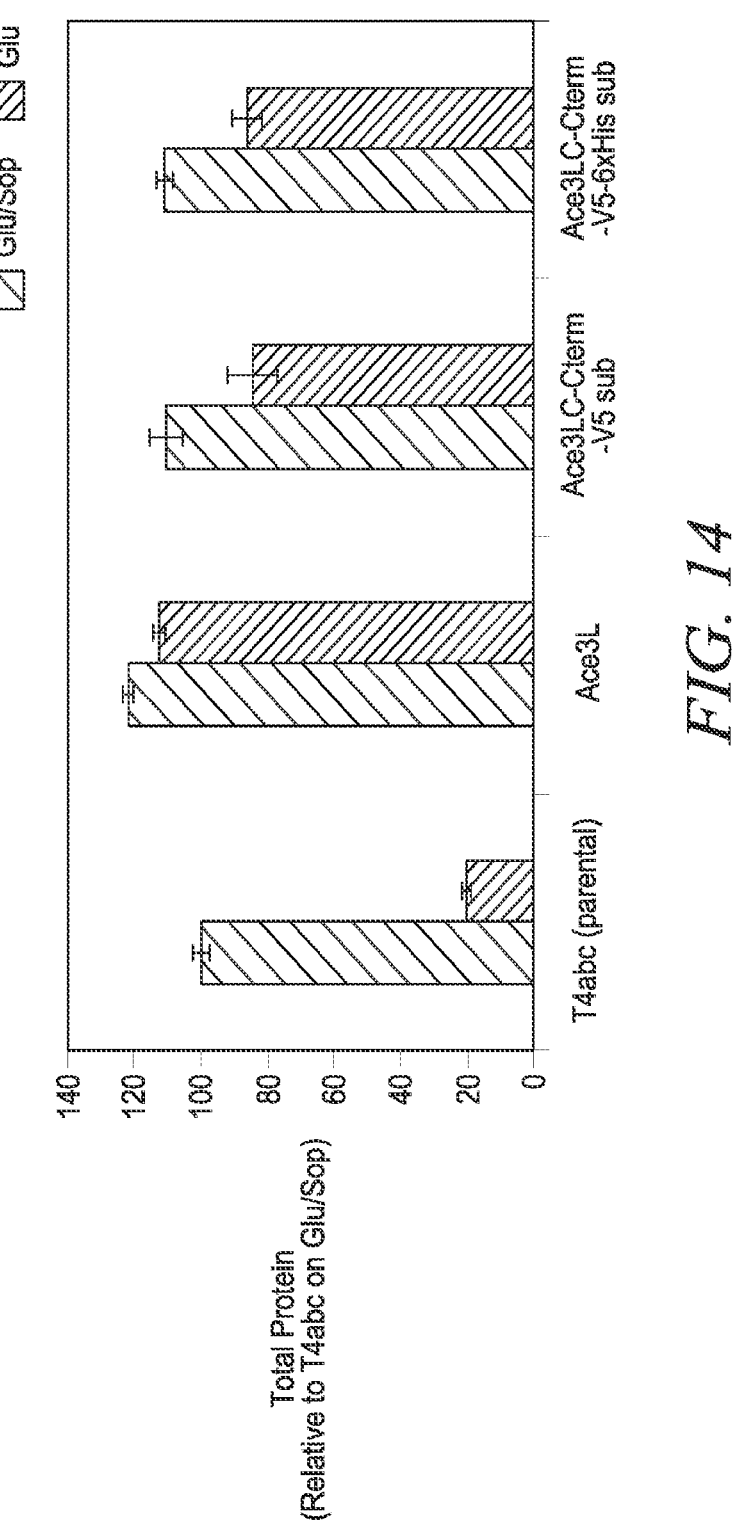

FIG. 14 shows the total secreted protein titers of *T. reesei* strains fermented under inducing (Glu/Sop) conditions and non-inducing (Glu) conditions.

Figure 15:
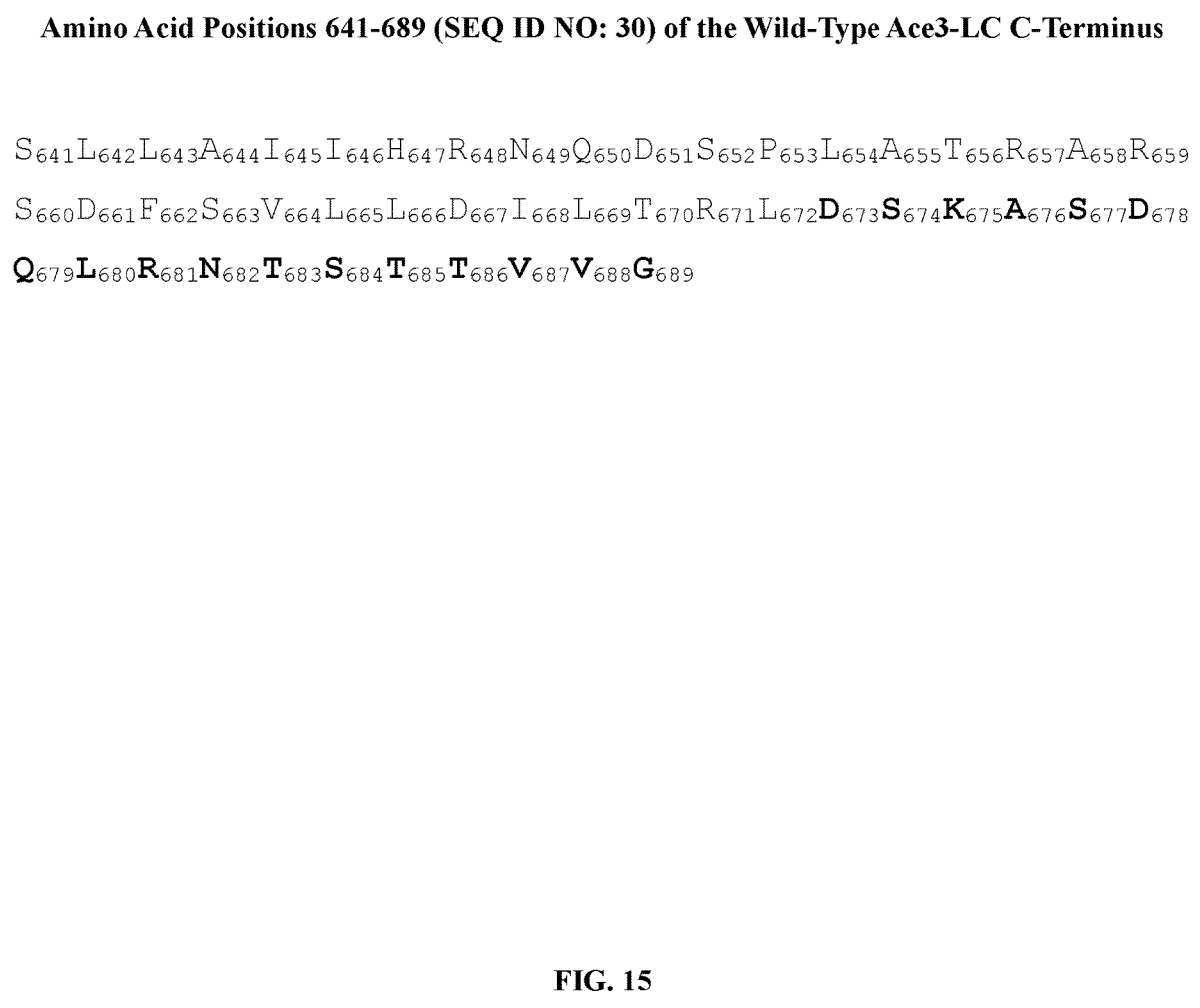

FIG. 15 presents a subsequence of the wild-type Ace3-LC protein (SEQ ID NO: 2) comprising the full-length (wild-type) Ace3-LC C-terminal amino acid positions 641-689 of SEQ ID NO: 30. As shown in FIG. 15 (SEQ ID NO: 30), the amino acid positions are presented as $S_{641}$ through $G_{689}$, wherein the uppercase letter designates the amino acid residue and the subscripted number that follows designates its position.

DESCRIPTION OF THE BIOLOGICAL SEQUENCES

SEQ ID NO: 1 is a wild-type *Trichoderma reesei* polynucleotide sequence comprising a gene encoding an Ace3 protein (SEQ ID NO: 2) named "Ace3-LC".

SEQ ID NO: 2 is the amino acid sequence of the Ace3-LC protein encoded by SEQ ID NO: 1.

SEQ ID NO: 3 is a *T. reesei* polynucleotide sequence comprising a gene encoding an Ace3 protein (SEQ ID NO: 4) named "Ace3-S".

SEQ ID NO: 4 is the amino acid sequence of the Ace3-S protein encoded by SEQ ID NO: 3.

SEQ ID NO: 5 is a *T. reesei* polynucleotide sequence comprising a gene encoding an Ace3 protein (SEQ ID NO: 6) named "Ace3-L".

SEQ ID NO: 6 is the amino acid sequence of the Ace3-L protein encoded by SEQ ID NO: 5.

SEQ ID NO: 7 is the amino acid sequence of a variant Ace3 protein named "C-term-5".

SEQ ID NO: 8 is the amino acid sequence of a variant Ace3 protein named "C-term-6".

SEQ ID NO: 9 is the amino acid sequence of a variant Ace3 protein named "C-term-7".

SEQ ID NO: 10 is the amino acid sequence of a variant Ace3 protein named "C-term-8".

SEQ ID NO: 11 is the amino acid sequence of a variant Ace3 protein named "C-term-9".

SEQ ID NO: 12 is the amino acid sequence of a variant Ace3 protein named "C-term-10".

SEQ ID NO: 13 is the amino acid sequence of a variant Ace3 protein named "C-term-12".

SEQ ID NO: 14 is the amino acid sequence of a variant Ace3 protein named "C-term-13".

SEQ ID NO: 15 is the amino acid sequence of a variant Ace3 protein named "C-term-14".

SEQ ID NO: 16 is the amino acid sequence of a variant Ace3 protein named "C-term-15".

SEQ ID NO: 17 is the amino acid sequence of a variant Ace3 protein named "C-term-16".

SEQ ID NO: 18 is the amino acid sequence of a variant Ace3 protein named "C-term-17".

SEQ ID NO: 19 is the amino acid sequence of a variant Ace3 protein named "C-term-18".

SEQ ID NO: 20 is the amino acid sequence of a variant Ace3 protein named "C-term-19".

SEQ ID NO: 21 is the amino acid sequence of a variant Ace3 protein named "C-term-20".

SEQ ID NO: 22 is the amino acid sequence of a variant Ace3 protein named "C-term-25".

SEQ ID NO: 23 is a nucleic acid primer sequence (TP218).

SEQ ID NO: 24 is a nucleic acid primer sequence (TP220).

SEQ ID NO: 25 is a nucleic acid primer sequence (TP125).

SEQ ID NO: 26 is a nucleic acid primer sequence (TP123).

SEQ ID NO: 27 is a nucleic acid primer sequence (TP221).

SEQ ID NO: 28 is a nucleic acid primer sequence (TP222).

SEQ ID NO: 29 is an amino acid sequence of the Ace3 binuclear (Zn$_2$Cys$_6$) zinc DNA binding domain.

SEQ ID NO: 30 comprises amino acid residue positions 641 to 689 defining the "Ace3-LC C-terminus".

SEQ ID NO: 31 is a polynucleotide sequence encoding the Ace3-LC C-terminus of SEQ ID NO: 30.

SEQ ID NO: 32 is a polynucleotide sequence encoding an Ace3-LC C-terminus variant named "Ace3-LC C-terminus mut_673".

SEQ ID NO: 33 is a polynucleotide sequence encoding an Ace3-LC C-terminus variant named "Ace3-LC C-terminus mut_674".

SEQ ID NO: 34 is a polynucleotide sequence encoding an Ace3-LC C-terminus variant named "Ace3-LC C-terminus mut_675".

SEQ ID NO: 35 is a polynucleotide sequence encoding an Ace3-LC C-terminus variant named "Ace3-LC C-terminus mut_676".

SEQ ID NO: 36 is a polynucleotide sequence encoding an Ace3-LC C-terminus variant named "Ace3-LC C-terminus mut_677".

SEQ ID NO: 37 is a polynucleotide sequence encoding an Ace3-LC C-terminus variant named "Ace3-LC C-terminus mut_678".

SEQ ID NO: 38 is a polynucleotide sequence encoding an Ace3-LC C-terminus variant named "Ace3-LC C-terminus mut_679".

SEQ ID NO: 39 is a polynucleotide sequence encoding an Ace3-LC C-terminus variant named "Ace3-LC C-terminus mut_680".

SEQ ID NO: 40 is a polynucleotide sequence encoding an Ace3-LC C-terminus variant named "Ace3-LC C-terminus mut_681".

SEQ ID NO: 41 is a polynucleotide sequence encoding an Ace3-LC C-terminus variant named "Ace3-LC C-terminus mut_682".

SEQ ID NO: 42 is a polynucleotide sequence encoding an Ace3-LC C-terminus variant named "Ace3-LC C-terminus mut_683".

SEQ ID NO: 43 is a polynucleotide sequence encoding an Ace3-LC C-terminus variant named "Ace3-LC C-terminus ins_672".

SEQ ID NO: 44 is a polynucleotide sequence encoding an Ace3-LC C-terminus variant named "Ace3-LC C-terminus ins_673".

SEQ ID NO: 45 is a polynucleotide sequence encoding an Ace3-LC C-terminus variant named "Ace3-LC C-terminus ins_674".

SEQ ID NO: 46 is a polynucleotide sequence encoding an Ace3-LC C-terminus variant named "Ace3-LC C-terminus ins_675".

SEQ ID NO: 47 is a polynucleotide sequence encoding an Ace3-LC C-terminus variant named "Ace3-LC C-terminus ins_676".

SEQ ID NO: 48 is a polynucleotide sequence encoding an Ace3-LC C-terminus variant named "Ace3-LC C-terminus ins_677".

SEQ ID NO: 49 is a polynucleotide sequence encoding an Ace3-LC C-terminus variant named "Ace3-LC C-terminus ins_678".

SEQ ID NO: 50 is a polynucleotide sequence encoding an Ace3-LC C-terminus variant named "Ace3-LC C-terminus ins_679".

SEQ ID NO: 51 is a polynucleotide sequence encoding an Ace3-LC C-terminus variant named "Ace3-LC C-terminus ins_680".

SEQ ID NO: 52 is a polynucleotide sequence encoding an Ace3-LC C-terminus variant named "Ace3-LC C-terminus ins_681".

SEQ ID NO: 53 is a polynucleotide sequence encoding an Ace3-LC C-terminus variant named "Ace3-LC C-terminus ins_682".

SEQ ID NO: 54 is a polynucleotide sequence encoding an Ace3-LC C-terminus variant named "Ace3-LC C-terminus ins_683".

SEQ ID NO: 55 is a polynucleotide sequence encoding an Ace3-LC C-terminus variant named "Ace3-LC C-terminus del_673-675".

SEQ ID NO: 56 is a polynucleotide sequence encoding an Ace3-LC C-terminus variant named "Ace3-LC C-terminus del_674-676".

SEQ ID NO: 57 is a polynucleotide sequence encoding an Ace3-LC C-terminus variant named "Ace3-LC C-terminus del_675-677".

SEQ ID NO: 58 is a polynucleotide sequence encoding an Ace3-LC C-terminus variant named "Ace3-LC C-terminus del_676-678".

SEQ ID NO: 59 is a polynucleotide sequence encoding an Ace3-LC C-terminus variant named "Ace3-LC C-terminus del_677-679".

SEQ ID NO: 60 is a polynucleotide sequence encoding an Ace3-LC C-terminus variant named "Ace3-LC C-terminus del_678-680".

SEQ ID NO: 61 is a polynucleotide sequence encoding an Ace3-LC C-terminus variant named "Ace3-LC C-terminus del_679-681".

SEQ ID NO: 62 is a polynucleotide sequence encoding an Ace3-LC C-terminus variant named "Ace3-LC C-terminus del_680-682".

SEQ ID NO: 63 is a polynucleotide sequence encoding an Ace3-LC C-terminus variant named "Ace3-LC C-terminus del_681-683".

SEQ ID NO: 64 is a polynucleotide sequence encoding an Ace3-LC C-terminus variant named "Ace3-LC C-terminus del_682-684".

SEQ ID NO: 65 is a polynucleotide sequence encoding an Ace3-LC C-terminus variant named "Ace3-LC C-terminus del_683-685".

SEQ ID NO: 66 is a polynucleotide sequence encoding an Ace3-LC C-terminus V5 substitution comprising the amino acid sequence of SEQ ID NO: 67.

SEQ ID NO: 67 is the amino acid sequence of the "Ace3-LC C-terminus V5 substitution" variant.

SEQ ID NO: 68 is a polynucleotide sequence encoding an Ace3-LC C-terminus V5-(6×His) substitution comprising the amino acid sequence of SEQ ID NO: 69.

SEQ ID NO: 69 is the amino acid sequence of the "Ace3-LC C-terminus V5-(6×His) substitution" variant.

SEQ ID NO: 70 is a sgRNA targeting the gla1 gene locus.

DETAILED DESCRIPTION

I. Overview

As described herein, certain embodiments of the disclosure are related to mutant and/or genetically modified

*Trichoderma* sp. fungal cells for use in the commercial scale production of proteins of interest. More particularly, certain embodiments of the disclosure are related to novel Ace3 (variant) transcription factor (TF) proteins capable of upregulating the expression of one or more genes encoding a lignocellulosic degrading enzyme. Thus, certain embodiments are directed to polynucleotides (nucleic acid sequences) encoding a novel (variant) Ace3 TF protein disclosed herein. For example, certain embodiments of the disclosure are directed to an isolated polynucleotide encoding a variant Ace3 TF protein, wherein the variant Ace3 TF comprises at least 90% sequence identity to amino acid positions 1-672 of SEQ ID NO: 2 and comprises a genetic modification of one or more C-terminal amino acid residues selected from positions 673-689 of SEQ ID NO: 2.

Certain embodiments are therefore related to genetically modified *Trichoderma* sp. cells comprising an ace3 gene encoding a variant Ace3 TF protein of the disclosure, wherein the modified cells are capable of producing a protein of interest in the absence of inducing substrates. Certain other embodiments are related to genetically modified *Trichoderma* sp. cells comprising an ace3 gene encoding a variant Ace3 TF protein of the disclosure, wherein the modified cells are capable of producing increased amounts of a protein of interest produced in the presence of an inducing substrate (i.e., relative to the amount of the same protein of interest produced by a control *Trichoderma* sp. cell comprising a wild-type ace3 gene encoding a wild-type Ace3 protein (e.g., SEQ ID NO: 2), when the modified and control *Trichoderma* sp. cells are cultivated/fermented in the presence of an inducing substrate under same conditions for the production of the POI. Thus, certain other embodiments of the disclosure are related to compositions and methods for constructing, genetically modifying, testing, screening, isolating and the like, modified *Trichoderma* sp. cells (strains) comprising and expressing a variant Ace3 transcription factor (TF) protein of the disclosure.

II. Definitions

Prior to describing the present compositions and methods in further detail, the following terms and phrases are defined. Terms not defined should be accorded their ordinary meaning as used and known to one skilled in the art.

All publications and patents cited in this specification are herein incorporated by reference.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of $^{-}10\%$ to $^{+}10\%$ of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

In accordance with this Detailed Description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely", "only", "excluding", "not including" and the like in connection with the recitation of claim elements, or use of a "negative" limitation or "proviso".

It is further noted that the term "comprising", as used herein, means "including, but not limited to", the component(s) after the term "comprising". The component(s) after the term "comprising" are required or mandatory, but the composition comprising the component(s) may further include other non-mandatory or optional component(s).

It is also noted that the term "consisting of," as used herein, means "including and limited to", the component(s) after the term "consisting of". The component(s) after the term "consisting of" are therefore required or mandatory, and no other component(s) are present in the composition.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, the term "Ascomycete fungal cell" refers to any organism in the Division Ascomycota in the Kingdom Fungi. Examples of Ascomycetes fungal cells include, but are not limited to, filamentous fungi in the subphylum Pezizomycotina, such as *Trichoderma* sp., *Aspergillus* sp., *Myceliophthora* sp., *Penicillium* sp., and the like.

As used herein, the term "filamentous fungus" refers to all filamentous forms of the subdivision Eumycota and Oomycota. For example, filamentous fungi include, without limitation, *Acremonium, Aspergillus, Emericella, Fusarium, Humicola, Mucor, Myceliophthora, Neurospora, Penicillium, Scytalidium, Thielavia, Tolypocladium,* and *Trichoderma* species.

In some embodiments, a filamentous fungus is a *Trichoderma* sp. cell (strain) including, but not limited to, *Trichoderma harzianum, Trichoderma koningii, Trichoderma longibrachiatum, Trichoderma reesei* or *Trichoderma viride.*

In some embodiments, a filamentous fungus may be an *Aspergillus* sp. cell (strain) such as *Aspergillus aculeatus, Aspergillus awamori, Aspergillus foetidus, Aspergillus japonicus, Aspergillus nidulans, Aspergillus niger*, or *Aspergillus oryzae*.

In some embodiments, the filamentous fungus is a *T. reesei* cell derived from *T. reesei* strain "Rut-C30", which is available from the American Type Culture Collection as *Trichoderma reesei* ATCC Deposit No. 56765. In other embodiments, the filamentous fungus is a *T. reesei* cell derived from *T. reesei* strain "RL-P37", which is available from the culture collection of the Northern Regional Research Laboratory, US Department of Agriculture as NRRL No. 15709.

As used herein, a "mutant cell" when used in phrases such as a "mutant *Trichoderma* sp. cell", the term "mutant cell" particularly refers to any naturally occurring *Trichoderma* sp. (mutant) cell comprising a mutated ace3 gene encoding a mutated Ace3 TF of the disclosure. For example, a population of *Trichoderma* sp. cells may be screened according to methods described herein to identify a naturally occurring mutant *Trichoderma* sp. cell capable of producing a protein of interest in the absence of an inducing substrate. For example, in certain embodiments, a mutant *Trichoderma* sp. cell identified as above is isolated from the population of *Trichoderma* sp. cells and cultivated/fermented under suitable conditions for the production of a protein of interest in the absence of an inducing substrate.

As used herein, the phrases "variant filamentous fungal cell(s)", "modified filamentous fungal cell(s)", "variant fungal cell(s)", "modified fungal cell(s)", "variant fungal strain(s)"," and the like refer to filamentous fungal cells that are derived (i.e., obtained) from a parental filamentous fungal cell belonging to the Pezizomycotina subphylum. Thus, a "modified" or "variant" filamentous fungal cell as used herein is derived from a "parental" filamentous fungal cell, wherein the "modified" cell comprises at least one genetic modification which is not found in the "parental" cell. For example, when comparing a "modified cell" vis-à-vis a "parental cell" of the instant disclosure, the "parental" cell serves as the unmodified "control" cell relative to "modified" cell which comprises the at least one genetic modification.

As used herein, the terms "modification" and "genetic modification" are used interchangeably and include: (a) the introduction, substitution, or removal of one or more nucleotides in a gene (or an ORF thereof), or the introduction, substitution, or removal of one or more nucleotides in a regulatory element required for the transcription or translation of the gene or ORF thereof, (b) a gene disruption, (c) a gene conversion, (d) a gene deletion, (e) the down-regulation of a gene, (f) specific mutagenesis and/or (g) random mutagenesis of any one or more the genes disclosed herein.

As used herein, "disruption of a gene", "gene disruption", "inactivation of a gene" and "gene inactivation" are used interchangeably and refer broadly to any genetic modification that substantially prevents a host cell from producing a functional gene product (e.g., a protein). Exemplary methods of gene disruptions include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and any combinations and variations thereof which disrupt/inactivate the target gene(s) and substantially reduce or prevent the production of the functional gene product (i.e., a protein).

As used herein, the terms "down-regulation" of gene expression and "up-regulation" of gene expression include any method that results in lower (down-regulated) or higher (up-regulated) expression of a gene. For example, the down-regulation of a gene can be achieved by RNA-induced gene silencing, genetic modifications of control elements such as the promoter, ribosomal binding site (RBS)/Shine-Dalgarno sequences, untranslated regions (UTRs), codon changes, and the like.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing mutations into the chromosome of a host cell through homologous recombination. In some embodiments, the targeting vector comprises other non-homologous sequences, e.g., added to the ends (i.e., stuffer sequences or flanking sequences). The ends can be closed such that the targeting vector forms a closed circle, such as, for example, insertion into a vector. For example, in certain embodiments, a parental *Trichoderma* sp. cell comprises an ace3 gene encoding a variant Ace3 protein (e.g., Ace3-S; SEQ ID NO: 4) comprising a truncated (non-functional) N-terminal binuclear zinc cluster DNA binding domain.

Thus, as described and contemplated herein, in certain embodiments an ace3 gene encoding a variant Ace3 protein (e.g., Ace3-S; SEQ ID NO: 4) is genetically modified (e.g., transformed) by introducing into the parental cell one or more "targeting vectors" which are designed to restore the native DNA binding domain of the Ace3 protein. For example, the native Ace3 DNA binding domain comprises the amino acid sequence set forth in SEQ ID NO: 29. Selection and/or construction of appropriate vectors (e.g., for the restoration of the native Ace3 DNA binding in the ace3 gene) is well within the knowledge of those having skill in the art. Likewise, in other embodiments, one or more targeting vectors are designed/constructed to delete, introduce (insert) and/or substitute one or more nucleotides into the ace3 gene, such that the encoded Ace3 protein comprises a modified C-terminus, as described herein.

As used herein, a "flanking sequence" refers to any sequence that is either upstream or downstream of the sequence being discussed (e.g., for genes A-B-C, gene B is flanked by the A and C gene sequences). In certain embodiments, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. The sequence of each homology box is homologous to a sequence in the *Trichoderma* sp. chromosome. These sequences direct where in the *Trichoderma* sp. chromosome the new construct gets integrated and what part of the *Trichoderma* sp. chromosome will be replaced by the incoming sequence. In other embodiments, the 5' and 3' ends of a selective marker are flanked by a polynucleotide sequence comprising a section of the inactivating chromosomal segment.

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "wild-type" and "native" are used interchangeably and refer to genes, proteins, fungal cells or strains as found in nature.

As used herein, a *Trichoderma reesei* "QM6a strain" comprises an ace3 gene encoding an Ace3 protein named "Ace3-S" (SEQ ID NO: 4).

As used herein, a *Trichoderma reesei* "RL-P37 strain" comprises an ace3 gene encoding an Ace3 protein herein named "Ace3-L" (SEQ ID NO: 6).

As used herein, an "Ace3-LC" protein comprises an amino acid sequence of SEQ ID NO: 2. As shown in FIG. 1, the Ace3-LC protein comprises six-hundred eighty-nine (689) amino acid residues with an N-terminal amino acid sequence comprising an intact binuclear zinc cluster ($Zn_2Cys_6$) DNA binding domain (FIG. 1A; indicated by the six (6) bold and grey cysteine (C) resides) and a full-length (wild-type; non-truncated) C-terminus ending in a glycine (G) residue at position 689 (FIG. 1B). As used herein, the last forty-nine (49) amino acid residue positions of the native Ace3-LC protein (SEQ ID NO: 2; i.e., residue positions 641 to 689) are set forth as SEQ ID NO: 30 (e.g., see, FIG. 15). Thus, in certain embodiments, a variant Ace3 protein comprises a modified C-terminus, wherein the modified C-terminus is relative to the native Ace3-LC C-terminus amino acid positions 641 to 689 of SEQ ID NO: 30.

As used herein, an "Ace3-L" protein comprises an amino acid sequence of SEQ ID NO: 6. As shown in FIG. 1, the Ace3-L protein comprises an N-terminal amino acid sequence comprising an intact binuclear zinc cluster ($Zn_2Cys_6$) DNA binding domain (indicated by the six (6) bold and grey cysteine (C) resides; FIG. 1A) and comprises a truncated C-terminus ending in an aspartic acid (D) residue (FIG. 1B, e.g., relative to the Ace3-LC protein C-terminus; SEQ ID NO: 2).

As used herein, an "Ace3-S" protein comprises an amino acid sequence of SEQ ID NO: 4. As shown in FIG. 1A, the Ace3-S protein comprises a shorter (truncated) N-terminal amino acid sequence relative to Ace3-LC (FIG. 1A; SEQ ID NO: 2) and/or Ace3-L (FIG. 1A; SEQ ID NO: 6). Thus, as shown in FIG. 1A, the Ace3-S protein does not comprise an intact binuclear zinc cluster ($Zn_2Cys_6$) DNA binding domain (i.e., relative to the N-terminal sequence of Ace3-LC and Ace3-L).

As used herein, the phrases "Ace3 DNA binding domain" and "Ace3 binuclear zinc cluster ($Zn_2Cys_6$) DNA domain" may be used interchangeably and refer to an amino acid sequence comprising homology to the Ace3 DNA binding domain of SEQ ID NO: 29. For example, the Ace3 DNA binding domain of SEQ ID NO: 29 (FIG. 3) is located within amino acid positions 73-109 of the Ace3-LC (SEQ ID NO: 2) and Ace3-L (SEQ ID NO: 6) proteins.

As used herein, the term "upregulate(s)" when recited in phrases such as an "Ace3 TF protein 'upregulates' the expression of a gene encoding a lignocellulosic degrading enzyme", the term specifically refers to an Ace3 TF protein capable of upregulating the expression of a gene encoding a lignocellulosic degrading enzyme in the absence of an inducing substrate. For example, a modified filamentous fungal cell of the disclosure comprising an Ace3 TF protein that upregulates the expression of a gene encoding a lignocellulosic degrading enzyme can produce the lignocellulosic degrading enzyme in the absence of an inducing substrate. In contrast, a filamentous fungal (control) cell comprising a wild-type ace3 gene encoding a wild-type Ace3 TF protein does not upregulate the expression of a gene encoding a lignocellulosic degrading enzyme in the absence of an inducing substrate.

As used herein, the term "lignocellulosic degrading enzyme" includes, but is not limited to, a cellobiohydrolase, an endoglucanase and a β-glucosidase. As used herein, the term "increased amount" when used in phrases such as a "modified cell produces an 'increased amount' of a lignocellulosic degrading enzyme in the presence of an inducing substrate", the "increased amount" of a lignocellulosic degrading enzyme produced is relative to the amount of the same lignocellulosic degrading enzyme produced by a parental cell, when the modified and parental cells are cultivate/fermented under the same conditions for the production of a POI in the presence of the same inducing substrate.

As set forth below in the Examples section and described hereinafter, certain embodiments of the disclosure are directed to genetically modified *Trichoderma* sp. fungal cells (strains) derived from a parental *Trichoderma* sp. cells (strains) comprising an ace3 gene encoding an Ace3 transcription factor (TF) protein comprising at least 90% sequence identity to SEQ ID NO: 2, wherein the genetically modified cell comprises a modified ace3 gene encoding a variant Ace3 TF protein comprising at least 90% sequence identity to amino acid positions 1-672 of SEQ ID NO: 2 and comprising a genetic modification of one or more C-terminal amino acid residues selected from positions 673-689 of SEQ ID NO: 2. For example, in certain embodiments, a modified *Trichoderma* sp. fungal cell of the disclosure comprises a variant Ace3 TF protein capable of upregulating the expression of an open reading frame (ORF) encoding a protein of interest (POI) when the ORF is operably linked to an upstream (5') promoter sequence derived from a gene encoding lignocellulosic degrading enzyme.

Thus, as used herein, the term "upregulate(s)" when recited in phrases such as a "variant Ace3 TF protein capable of upregulating the expression of an ORF encoding a protein of interest (POI), wherein the ORF is operably linked to an upstream (5') promoter sequence derived from a gene encoding lignocellulosic degrading enzyme", the term specifically refers to an Ace3 TF protein capable of upregulating the expression of an ORF encoding a POI in the absence of an inducing substrate.

As used herein, "an upstream (5') promoter sequence derived from a gene encoding lignocellulosic degrading enzyme" includes, but is not limited to, a cellobiohydrolase promoter sequence, an endoglucanase promoter sequence, a β-glucosidase promoter sequence, and a xylanase promoter sequence.

As used herein, the term "increased amount" when used in phrases such as a "modified cell produces an 'increased amount' of a protein of interest (POI) in the presence of an inducing substrate", the "increased amount" of the POI produced is relative to the amount of the same POI produced by a parental cell or a control cell. For example, a modified filamentous fungal cell of the disclosure comprising an Ace3 TF protein that can upregulate the expression of an ORF encoding a POI (i.e., when the ORF is operably linked to a 5' promoter sequence derived from a gene encoding lignocellulosic degrading enzyme) produces an increased amount of the POI when cultivated/fermented in the presence of an inducing substrate, relative to the amount of the same POI produced by a control cell comprising a wild-type ace3 gene encoding a wild-type Ace3 TF protein (e.g., SEQ ID NO:2) when cultivated/fermented in the presence of the same inducing substrate.

As used herein, certain amino acid deletions (truncations) of the wild-type Ace3 C-terminus are abbreviated "C-term", followed by a numerical designation (e.g., "C-term-5"

through "C-term-20", and "C-term-25"), wherein the numerical designation represents the number of amino acid residues deleted from the Ace3 C-terminus (i.e., relative to the wild-type Ace3 C-terminus ending in a glycine (G) at position 689; SEQ ID NO: 2). For example, by reference to the wild-type Ace3 C-terminus shown in FIG. 4 (i.e., which ends with a glycine (G) at position 689), a "C-term-7" protein comprises a seven (7) amino acid deletion (truncation) of the last seven C-terminal amino acids (i.e., "TSTTVVG") and a "C-term-17" protein comprises a seventeen (17) amino acid deletion (truncation) of the last seventeen C-terminal amino acids (i.e., "DSKASDQLRN-TSTTVVG").

In certain embodiments, the wild-type (Ace3) C-terminal amino acid residues are referenced and assigned negative numbers for visual clarity. For example, as presented in FIG. 4, the most C-terminal amino acid position of the Ace3-LC protein (i.e., glycine (G) at position 689) is assigned a negative one (−1), the threonine (T) at position 685 assigned a negative five (−5), the leucine (L) at position 680 assigned a negative ten (−10), the lysine (K) at position 675 assigned a negative fifteen (−15), etc.

As used herein, an Ace3 "C-term-5" protein (FIG. 2A; SEQ ID NO: 7) comprises six-hundred eighty-four (684) amino acid residues with a five (5) amino acid truncation at the C-terminus ending in serine (S) at position 684 (relative to WT Ace3 C-terminus; SEQ ID NO: 2).

As used herein, an Ace3 "C-term-6" protein (FIG. 2A; SEQ ID NO: 8) comprises six-hundred eighty-three (683) amino acid residues and a six (6) amino acid truncation at the C-terminus ending in threonine (T) at position 683 (relative to WT Ace3 C-terminus; SEQ ID NO: 2).

As used herein, an Ace3 "C-term-7" protein (FIG. 2B; SEQ ID NO: 9) comprises six-hundred eighty-two (682) amino acid residues with a seven (7) amino acid truncation at the C-terminus ending in asparagine (N) at position 682 (relative to WT Ace3 C-terminus; SEQ ID NO: 2).

As used herein, an Ace3 "C-term-8" protein (FIG. 2B; SEQ ID NO: 10) comprises six-hundred eighty-one (681) amino acid residues with an eight (8) amino acid truncation at the C-terminus ending in arginine (R) at position 681 (relative to WT Ace3 C-terminus; SEQ ID NO: 2).

As used herein, an Ace3 "C-term-9" protein (FIG. 2B; SEQ ID NO: 11) comprises six-hundred eighty (680) amino acid residues with a nine (9) amino acid truncation at the C-terminus ending in leucine (L) at position 680 (relative to WT Ace3 C-terminus; SEQ ID NO: 2).

As used herein, an Ace3 "C-term-10" protein (FIG. 2C; SEQ ID NO: 12) comprises six-hundred seventy-nine (679) amino acid residues with a ten (10) amino acid truncation at the C-terminus ending in glutamine (Q) at position 679 (relative to WT Ace3 C-terminus; SEQ ID NO: 2).

As used herein, an Ace3 "C-term-12" protein (FIG. 2C; SEQ ID NO: 13) comprises six-hundred seventy-seven (677) amino acid residues with a twelve (12) amino acid truncation at the C-terminus ending in serine (S) at position 677 (relative to WT Ace3 C-terminus; SEQ ID NO: 2).

As used herein, an Ace3 "C-term-13" protein (FIG. 2C; SEQ ID NO: 14) comprises six-hundred seventy-six (676) amino acid residues with a thirteen (13) amino acid truncation at the C-terminus ending in alanine (A) at position 676 (relative to WT Ace3 C-terminus; SEQ ID NO: 2).

As used herein, an Ace3 "C-term-14" protein (FIG. 2D; SEQ ID NO: 15) comprises six-hundred seventy-five (675) amino acid residues with a fourteen (14) amino acid truncation at the C-terminus ending in lysine (K) at position 675 (relative to WT Ace3 C-terminus; SEQ ID NO: 2).

As used herein, an Ace3 "C-term-15" protein (FIG. 2D; SEQ ID NO: 16) comprises six-hundred seventy-four (674) amino acid residues with a fifteen (15) amino acid truncation at the C-terminus ending in serine (S) at position 674 (relative to WT Ace3 C-terminus; SEQ ID NO: 2).

As used herein, an Ace3 "C-term-16" protein (FIG. 2D; SEQ ID NO: 17) comprises six-hundred seventy-three (673) amino acid residues with a sixteen (16) amino acid truncation at the C-terminus ending in aspartic acid (D) at position 673 (relative to WT Ace3 C-terminus; SEQ ID NO: 2).

As used herein, an Ace3 "C-term-17" protein (FIG. 2E; SEQ ID NO: 18) comprises six-hundred seventy-two (672) amino acid residues with a seventeen (17) amino acid truncation at the C-terminus ending in leucine (L) at position 672 (relative to WT Ace3 C-terminus; SEQ ID NO: 2).

As used herein, an Ace3 "C-term-18" protein (FIG. 2E; SEQ ID NO: 19) comprises six-hundred seventy-one (671) amino acid residues with an eighteen (18) amino acid truncation at the C-terminus ending in arginine (R) at position 671 (relative to WT Ace3 C-terminus; SEQ ID NO: 2).

As used herein, an Ace3 "C-term-19" protein (FIG. 2E; SEQ ID NO: 20) comprises six-hundred seventy (670) amino acid residues with a nineteen (19) amino acid truncation at the C-terminus ending in threonine (T) at position 670 (relative to WT Ace3 C-terminus; SEQ ID NO: 2).

As used herein, an Ace3 "C-term-20" protein (FIG. 2F; SEQ ID NO: 21) comprises six-hundred sixty-nine (669) amino acid residues with a twenty (20) amino acid truncation at the C-terminus ending in leucine (L) at position 669 (relative to WT Ace3 C-terminus; SEQ ID NO: 2).

As used herein, an Ace3 "C-term-25" protein (FIG. 2F; SEQ ID NO: 22) comprises six-hundred sixty-four (664) amino acid residues with a twenty-five (25) amino acid truncation at the C-terminus ending in valine (V) at position 664 (relative to WT Ace3 C-terminus; SEQ ID NO: 2).

As used herein, the phrase modified or variant cell "comprising a genetic modification which expresses a gene encoding an Ace3 'C-term' protein" includes, but is not limited to, the introduction of at least one copy of a gene (or ORF) encoding an Ace3 'C-term' protein of the disclosure (e.g., C-term-7; SEQ ID NO: 9 through C-term-17; SEQ ID NO: 18). In certain embodiments, the gene (or ORF) encoding an Ace3 C-term protein is operably linked to an upstream (5') heterologous promoter sequence (i.e., ace3 gene is not linked to its native ace3 promoter sequence), and/or the gene (or ORF) encoding an Ace3 C-term protein is operably linked to a downstream (3') heterologous terminator sequence.

In certain embodiments, a modified cell comprising a genetic modification which expresses a gene encoding an Ace3 'C-term' protein of the disclosure (e.g., C-term-7; SEQ ID NO: 9 through C-term-17; SEQ ID NO: 18) includes the modification of an endogenous ace3 gene via CRISPR/Cas9 editing, wherein the CRISPR/Cas9 modified ace3 gene encodes an Ace3 'C-term' protein of the disclosure.

In certain embodiments, fungal cells of the disclosure may be screened for the presence of an endogenous ace3 gene encoding a truncated N-terminal binuclear zinc cluster DNA binding domain. For example, FIG. 3 (SEQ ID NO: 29) presents the intact DNA binding domain as found in the Ace3-L (SEQ ID NO: 6) and Ace3-LC (SEQ ID NO: 2) proteins. Thus, in certain embodiments, a parental fungal cell screened and identified as comprising (an endogenous) truncated N-terminus is genetically modified herein to restore the full length (wild-type) N-terminus (SEQ ID NO: 29).

Likewise, fungal cells of the disclosure may be screened for the presence of an endogenous ace3 gene encoding a full-length (wild-type) Ace3 C-terminus (e.g., Ace3-LC; SEQ ID NO: 2). For example, FIG. 4 presents the full-length (wild-type) C-terminus of the Ace3-LC protein (SEQ ID NO: 2). Thus, in certain embodiments, a parental fungal cell screened and identified as comprising an endogenous ace3 gene encoding a full-length (wild-type) C-terminus is genetically modified herein to delete (truncate) at least seven (7) amino acids and not more than seventeen (17) amino acids of the full-length (wild-type) C-terminus. Thus, as presented in FIG. 4, the Ace3 C-terminal amino acid residue positions shown with grey shading (i.e., positions –7 (T) through –17 (D)) indicate the minimum (at least 7) and maximum (no more than 17) number of permissible amino acid deletions (truncations) at the Ace3 C-terminus as further described hereinafter.

In other embodiments, modified filamentous fungal cells of the disclosure will comprise further genetic modifications. For example, in certain embodiments, such variant filamentous fungal cells may further comprise a genetic modification which reduces the expression and/or activity of a gene encoding the carbon catabolite repressor protein "Cre1" or the "Ace1" repressor protein. In other embodiments, such modified filamentous fungal cells further comprise a genetic modification which introduces at least one copy of a xylanase regulator 1 (Xyr1).

As used herein, the term "host cell" refers to a filamentous fungal cell that has the capacity to act as a host and expression vehicle for an incoming sequence (i.e., a polynucleotide sequence introduced into the cell), as described herein.

A "heterologous" nucleic acid construct or sequence has a portion of the sequence which is not native or existing in a native form to the cell in which it is expressed. Heterologous, with respect to a control sequence refers to a control sequence (e.g., promoters, enhancers) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell. Similarly, a heterologous protein will often refer to two or more subsequences that are not found in the same relationship to each other in nature (e.g., a fusion protein).

As used herein, the term "promoter" refers to a nucleic acid sequence that functions to direct transcription of a downstream gene or an open reading frame (ORF) thereof. The promoter will generally be appropriate to the host cell in which the target gene is being expressed. The promoter together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. In certain embodiments, the promoter is an inducible promoter. In other embodiments, the promoter is a constitutive promoter.

As used herein, a "promotor sequence" is a DNA sequence which is recognized by the particular filamentous fungus for expression purposes. A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A "constitutive" promoter is a promoter that is active under most environmental and developmental conditions. An "inducible" promoter is a promoter that is active under specific environmental or developmental regulation.

As used herein, the term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence. Thus, a nucleic acid is "operably linked" when it is placed into a functional relationship with another nucleic acid sequence. For example, DNA encoding a secretory leader (i.e., a signal peptide) is operably linked to DNA encoding a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. In other embodiments, linking is accomplished by seamless cloning methods where DNA were joined in a sequence-independent and scar-less manner. The seamless cloning is typically performed with, but not limited to, commercially available systems, such as Gibson Assembly (NEB), NEBuilder HiFi DNA Assembly (NEB), Golden Gate Assembly (NEB), and GeneArt Seamless cloning and Assembly system (ThermoFisher Scientific).

As used herein, a "heterologous "promoter" or "heterologous promoter sequence", as used in phrases such as an "ace3 gene (or ORF thereof) operably linked to an upstream (5') heterologous promoter sequence", the phrase "heterologous promoter" is meant to distinguish over the native ace3 promoter sequence, wherein a heterologous promoter sequence operably linked to an ace3 gene can be any promoter sequence functional in a filamentous fungal cell of the disclosure (i.e., excluding the native ace3 gene promoter).

Likewise, a "heterologous promoter sequence", as used in phrases such as an "a gene of interest (GOI) encoding a protein of interest (POI) is operably linked to an upstream (5') heterologous promoter sequence", the phrase "heterologous promoter" is meant to distinguish over the gene of interest's native promoter sequence, wherein a heterologous promoter sequence operably linked to a GOI encoding a POI can be any promoter sequence functional in a filamentous fungal cell of the disclosure (i.e., excluding the GOI's native promoter).

As used herein, the term "DNA construct" or "expression construct" refers to a nucleic acid sequence, which comprises at least two DNA polynucleotide fragments. A DNA or expression construct can be used to introduce nucleic acid sequences into a fungal host cell. The DNA may be generated in vitro (e.g., by PCR) or any other suitable techniques. In some preferred embodiments, the DNA construct comprises a sequence of interest (e.g., encoding a Ace3-L protein). In certain embodiments, a polynucleotide sequence of interest is operably linked to a promoter. In some embodiments, the DNA construct further comprises at least one selectable marker. In further embodiments, the DNA construct comprises sequences homologous to the host cell chromosome. In other embodiments, the DNA construct comprises non-homologous sequences to the host cell chromosome.

As used herein, the phrase "lignocellulosic degrading" enzyme includes cellobiohydrolases, endoglucanases and β-glucosidases.

As used herein, the terms "cellulase", "cellulolytic enzymes" or "cellulase enzymes" means bacterial or fungal enzymes such as exoglucanases, exocellobiohydrolases, endoglucanases and/or D-glucosidases. These different types of cellulase enzymes act synergistically to convert cellulose and its derivatives to glucose. For example, many microbes make enzymes that hydrolyze cellulose, including the wood rotting fungus *Trichoderma*, the compost bacteria *Thermomonospora* (now *Thermobifida*), *Bacillus*, and *Cellulomonas*; *Streptomyces*; and the fungi *Humicola, Aspergillus* and *Fusarium*. The enzymes made by these microbes are mixtures of proteins with three types of actions useful in the conversion of cellulose to glucose:endoglucanases (EG), cellobiohydrolases (CBH), and β-glucosidase (BG). As defined herein, the terms "endoglucanases" (EG), "cellobiohydrolases" (CBH) and "β-glucosidase" (BG) are used interchangeably with their abbreviations "EG", "CBH" and "BG", respectively.

As used herein, the term "coding sequence" refers to a nucleotide sequence, which directly specifies the amino acid sequence of its (encoded) protein product. The boundaries of the coding sequence are generally determined by an open reading frame, which usually begins with an ATG start codon. The coding sequence typically includes DNA, cDNA, and recombinant nucleotide sequences.

As defined herein, an "open reading frame" (hereinafter, an "ORF") means a nucleic acid or nucleic acid sequence (whether naturally occurring, non-naturally occurring, or synthetic) comprising an uninterrupted reading frame consisting of (i) an initiation codon, (ii) a series of codons representing amino acids, and (iii) a termination codon, the ORF being read (or translated) in the 5' to 3' direction.

As used herein, the term "gene" means the segment of DNA involved in producing a polypeptide chain, that may or may not include regions preceding and following the coding region (e.g., 5' untranslated (5' UTR) or "leader" sequences and 3' UTR or "trailer" sequences, as well as intervening sequences (introns) between individual coding segments (exons). The gene may encode commercially important industrial proteins or peptides, such as enzymes (e.g., proteases, mannanases, xylanases, amylases, glucoamylases, cellulases, oxidases, lipases and the like). The gene of interest may be a naturally occurring gene, a mutated gene or a synthetic gene.

As used herein, the term "recombinant" when used with reference to a cell, a nucleic acid, a protein, or a vector, indicates that the cell, nucleic acid, protein or vector, has been modified by the introduction of a heterologous nucleic acid or protein, or the alteration of a native nucleic acid or protein, or that the cell is derived from a cell so modified. Thus, for example, recombinant cells express genes that are not found within the native (non-recombinant) form of the cell, or express native genes that are otherwise abnormally expressed, under expressed or not expressed at all.

The term "vector" is defined herein as a polynucleotide designed to carry nucleic acid sequences to be introduced into one or more cell types. Vectors include cloning vectors, expression vectors, shuttle vectors, plasmids, phage or virus particles, DNA constructs, cassettes and the like. Expression vectors may include regulatory sequences such as promoters, signal sequences, a coding sequences and transcription terminators.

An "expression vector" as used herein means a DNA construct comprising a coding sequence that is operably linked to suitable control sequences capable of effecting expression of a protein in a suitable host. Such control sequences may include a promoter to effect transcription, an optional operator sequence to control transcription, a sequence encoding suitable ribosome binding sites on the mRNA, enhancers and sequences which control termination of transcription and translation.

As used herein, the term "secretory signal sequence" denotes a DNA sequence that encodes a polypeptide (i.e., a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

As used herein, the term "induction" refers to the increased transcription of a gene resulting in the synthesis of a protein of interest (POI) in a filamentous fungal cell at a markedly increased rate in response to the presence of an "inducer" (i.e., inducing substrate). To measure the "induction" of a "gene of interest" (GOI) or an "ORF of interest" encoding a POI, variant filamentous fungal (host) cells are treated with a candidate inducing substrate (inducer) and are compared vis-à-vis to parental filamentous fungal (control, unmodified) cells which are not treated with the inducing substrate (inducer). Thus, the (untreated) parental (control) cells are assigned a relative protein activity value of 100%, wherein induction of the GOI encoding the POI in the variant (modified) host cells is achieved when the activity value (i.e., relative to the control cells) is greater than 100%, greater than 105%, greater than 110%, greater than 150%, greater than 200-500% (i.e., relative to the control), or higher.

As used herein, the terms "inducer", "inducers", "inducing substrate" or "inducing substrates" are used interchangeably and refer to any compounds that cause filamentous fungal cells to produce "increased amounts" of polypeptides (e.g., enzymes, receptors, antibodies and the like) or other compounds/substances than they would produce if the inducing substrate was absent. Examples of inducing substrates include, but are not limited to, sophorose, lactose, gentibiose and cellulose.

As used herein, the term "inducing feed" refers to a composition comprising at least an "inducing substrate" (sophorose, lactose, gentibiose, cellulose) which is fed to filamentous fungal cells.

As used herein, the term "isolated" or "purified" refers to a filamentous fungal cell, a nucleic acid or a polypeptide that is removed from at least one component with which it is naturally associated.

As defined herein, the terms "protein of interest" or "POI" refer to a polypeptide that is desired to be expressed in a filamentous fungal cell. Such a protein can be an enzyme, a substrate-binding protein, a surface-active protein, a structural protein, and the like, and can be expressed at high levels, and can be for the purpose of commercialization. The protein of interest can be encoded by an endogenous gene or a heterologous gene. The protein of interest can be expressed intracellularly or as a secreted (extracellular) protein.

In certain embodiments, a gene (or ORF) encoding a POI for expression/production in a filamentous fungal cell of the disclosure comprises an upstream (5') cellulase gene promoter (e.g., cbh1) operably linked to the gene or ORF encoding the POI. Thus, the expression of a gene or ORF encoding a POI under the control a cellulase promoter (e.g., cbh1) is up-regulated in the presence of one or more of the modified Ace3 TF proteins described herein.

As used herein, the terms "polypeptide" and "protein" (and/or their respective plural forms) are used interchangeably to refer to polymers of any length comprising amino acid residues linked by peptide bonds. The conventional one-letter or three-letter codes for amino acid residues are used herein. The polymer can be linear or branched, it can comprise modified amino acids, and it can be interrupted by non-amino acids. The terms also encompass an amino acid polymer that has been modified naturally or by intervention (e.g., disulfide bond formation, glycosylation, lipidation, acetylation, phosphorylation, or any other manipulation or modification, such as conjugation with a labeling component). Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins." Such proteins can be derived from organisms of different genera and/or species, or even different classes of organisms (e.g., bacteria and fungi). Related proteins also encompass homologs determined by primary sequence analysis, determined by secondary or tertiary structure analysis, or determined by immunological cross-reactivity.

As used herein, the phrase "substantially free of an activity," or similar phrases, means that a specified activity is either undetectable in an admixture or present in an amount that would not interfere with the intended purpose of the admixture.

As used herein, the term "derivative polypeptide" refers to a protein which is derived or derivable from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative can be achieved by modifying a DNA sequence which encodes for the native protein, transformation of that DNA sequence into a suitable host, and expression of the modified DNA sequence to form the derivative protein.

Related (and derivative) proteins include "variant proteins." Variant proteins differ from a reference/parental protein (e.g., a wild-type protein) by substitutions, deletions, and/or insertions at a small number of amino acid residues. The number of differing amino acid residues between the variant and parental protein can be one or more, for example, 1, 2, 3, 4, 5, 6, 7, 8, 9, 10, 15, 20, 30, 40, 50, or more amino acid residues. Variant proteins can share at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein can also differ from a reference protein in selected motifs, domains, epitopes, conserved regions, and the like.

As used herein, the term "homologous protein" refers to a protein that has similar activity and/or structure to a reference protein. It is not intended that homologs necessarily be evolutionarily related. Thus, it is intended that the term encompass the same, similar, or corresponding protein (s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, WI); and Devereux et al., 1984).

As used herein, the phrases "substantially similar" and "substantially identical", in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Sequence identity can be determined using known programs such as BLAST, ALIGN, and CLUSTAL using standard parameters.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences.

As used herein, "disruption of a gene" refers broadly to any genetic or chemical manipulation, i.e., mutation, that substantially prevents a cell from producing a functional gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a functional gene product. A gene expression can also be disrupted using RNAi, CRISPR/Cas9 or any other method that abolishes, reduces or mitigates gene expression.

As used herein, "aerobic fermentation" refers to growth in the presence of oxygen.

As used herein, the term "cell broth" refers collectively to medium and cells in a liquid/submerged culture.

As used herein, the term "cell mass" refers to the cell component (including intact and lysed cells) present in a liquid/submerged culture. Cell mass can be expressed in dry or wet weight.

As used herein, a "functional protein" is a protein that possesses an activity, such as an enzymatic activity, a binding activity, a surface-active property, and the like, and which has not been mutagenized, truncated, or otherwise modified to abolish or reduce that activity.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, a "protein of interest" is a protein that is desired to be produced in a submerged culture of filamentous fungus cells. Generally, proteins of interest are commercially important for industrial, pharmaceutical, animal health, and food and beverage use, making them desirable to produce in large quantities. Proteins of interest are to be distinguished from the myriad other proteins expressed by the filamentous fungus cells, which are generally not of interest as products and are mainly considered background protein contaminants.

III. Activator of Cellulase Expression 3 (Ace3)

As generally described in Hakkinen et al. (2014), a *T. reesei* gene named "Activator of Cellulase Expression 3" (ace3) encodes a transcription factor (TF) protein named "Ace3", which Ace3 TF regulates cellulase and hemicellulase gene expression. In addition, Applicant's PCT Publication No. WO2018/067599 identified certain variant forms of the Ace3 TF protein that can upregulate cellulase/hemicellulase expression/production in *T. reesei* strains in the absence of inducing substrates (e.g., lactose, sophorose). For example, PCT Publication No. WO2018/067599 describes surprising and unexpected results when evaluating the cloned ace3 ORF described in Hakkinen et al. (2014) (i.e., based on the *T. reesei* "QM6a strain" annotation of ace3) relative to an ace3 ORF based on the *T. reesei* "RUT-C30 strain" annotation.

More particularly, the WO2018/067599 publication identified a mutated ace3 gene encoding a variant Ace3 TF capable of upregulating cellulase/hemicellulase gene expression in *T. reesei* strains in the absence of inducing substrates. As described in the WO2018/067599 publication, the mutated ace3 gene in *T. reesei* strains such as RL-P37 and RUT-C30 comprised a premature stop codon resulting in an eleven (11) amino acid truncation at the C-terminus of the variant Ace3 TF (i.e., relative to the C-terminus of the wild-type encoded Ace3 TF protein). For example, as shown in FIG. 1A of the instant disclosure, a variant Ace3 protein named "Ace3-S" (SEQ ID NO: 4) has a shorter (truncated) N-terminal sequence which is missing two (2) of the six (6) cysteine residues of the binuclear zinc cluster ($Zn_2Cys_6$) DNA binding domain (i.e., as found in the wild-type Ace3 TF binuclear zinc cluster ($Zn_2Cys_6$) DNA binding domain; SEQ ID NO: 29), and as shown in FIG. 1B, the variant Ace3-S TF protein (SEQ ID NO: 4) comprises a full-length (wild-type) C-terminus ending in glycine (G). In addition, as set forth in the WO2018/067599 publication and shown in FIG. 1A of the instant disclosure, the wild-type Ace3 protein named "Ace3-LC" (SEQ ID NO: 2) comprises a full-length N-terminus, which includes an intact binuclear zinc cluster ($Zn_2Cys_6$) DNA binding domain (SEQ ID NO: 29), and as shown in FIG. 1B, the wild-type Ace3-LC protein (SEQ ID NO: 2) comprises a full-length (wild-type) C-terminus ending in glycine (G). In contrast, as shown in FIG. 1A of the instant disclosure, a variant Ace3 protein named "Ace3-L" (SEQ ID NO: 6) comprises a full length (wild-type) N-terminus, which includes an intact binuclear zinc cluster ($Zn_2Cys_6$) DNA binding domain (SEQ ID NO: 29), and as shown in FIG. 1B, the Ace3-L protein (SEQ ID NO: 6) comprises an eleven (11) amino acid truncated C-terminus ending in aspartic acid (D). A recent publication by Zhang et al. (2019) further validated Applicant's experimental observations that an Ace3 variant with a full-length zinc cluster ($Zn_2Cys_6$) DNA binding domain was able to bind to DNA.

Thus, as generally set forth in PCT Publication No. WO2018/067599, *Trichoderma* sp. cells comprising an ace3 gene (or open reading frame thereof) encoding the variant Ace3-L protein (i.e., comprising the 11 amino acid truncation at the C-terminus; SEQ ID NO: 6) were capable of producing lignocellulosic degrading enzymes in the absence of inducing substrates relative to *Trichoderma* sp. cells comprising an ace3 gene (or open reading frame thereof) encoding the variant Ace3-S protein (SEQ ID NO: 4) or the wild-type Ace3-LC protein (SEQ ID NO: 2) (i.e., when fermented/cultivated under identical conditions). More recently, a publication by Chen et al. (2020) further validated Applicant's experimental observations that *Trichoderma* sp. cells comprising a mutated ace3 gene encoding a variant Ace3 TF protein having a truncation (deletion) of the last eleven (11) C-terminal amino acid residues (i.e., relative to the full-length (wild-type) Ace3 C-terminus) at the native ace3 locus enable such *Trichoderma* sp. cells to produced increased amounts of lignocellulosic degrading enzymes (e.g., cellulases/hemicellulases) relative to *Trichoderma* sp. cells comprising the wild-type ace3 gene encoding the wild-type Ace3 protein under inducing conditions.

Thus, when comparing the results of the present disclosure to the results/observations from publications of other authors (e.g., Zhang et al. 2019; Chen et al. 2020), Applicant emphasizes and notes the following differences between such observations. For example, as generally described herein and presented below in the Examples section, Applicant uses strains harboring an ace3 gene encoding a truncated Ace3 TF protein at the native locus as the (unmodified) parental strain, and over-express a variant ace3 gene encoding a variant Ace3 TF protein at an ectopic locus in the (modified) daughter strains. Therefore, the (modified) daughter cells of the instant disclosure produce a mix of the overexpressed variant Ace3 TF protein in addition to native Ace3 TF protein with a truncated C-terminus. In contrast, the Chen et al. (2020) publication only introduced a truncation of ace3 at its native locus. Likewise, the Zhang et al. (2019) publication describes a promoter swap strategy at the ace3 locus in *T. reesei* strain QM6a to over-express two (2) variant Ace3 TF proteins in the absence of its native Ace3 TF, wherein the first variant Ace3 TF comprised an incomplete zinc cluster ($Zn_2Cys_6$) DNA binding domain at the N-terminus and a wild-type C-terminus, and the second variant Ace3 TF was similar to, but not identical, to the wild-type Ace3 TF comprising a complete/intact zinc cluster ($Zn_2Cys_6$) DNA at the N-terminus and a comprising wild-type C-terminus. Thus, the two studies by Zang et al. (2019) and Chen et al. (2020) described above, generally demonstrate certain improvements in protein production under inducing conditions (i.e., when cultivated/fermented in the presence of an inducing substrate), whereas neither publication demonstrates or describes an improvement in protein production under non-inducing conditions (i.e., when cultivated/fermented in the absence of an inducing substrate).

In the instant disclosure, Applicant has further evaluated and dissected the wild-type C-terminus of the Ace3-LC TF protein (SEQ ID NO: 2; which wild-type Ace3-LC protein requires an inducing substrate to express/produce lignocellulosic degrading enzymes) relative to the truncated C-terminus of the Ace3-L TF protein (SEQ ID NO: 6; which Ace3-L protein does not require an inducing substrate to express/produce lignocellulosic degrading enzymes). More particularly, as set forth below in the Example 1, Applicant constructed multiple ace3 expression vectors encoding variant Ace3 proteins comprising serial amino acid deletions (truncations) at the C-terminus.

For example, a first set of six (6) vectors were constructed comprising C-terminal deletions ranging from zero (0) amino acid deletions to twenty-five (25) amino acid deletions, using a five (5) amino acid deletion increment (e.g., see TABLE 1; set 1). Likewise, a second set of twelve (12) vectors were constructed comprising C-terminal deletions ranging from six (6) amino acid deletions to nineteen (19) amino acid deletions, using a one (1) amino acid deletion increment (TABLE 1; set 2). Thus, the eighteen (18) Ace3 C-terminal variant proteins constructed in Example 1 (listed in TABLE 3) are based on the Ace3-LC protein sequence (SEQ ID NO: 2), which comprises the full-length (wild-type) Ace3 C-terminus ending in glycine (G) at position 689.

Applicant subsequently tested/screened the *T. reesei* strains constructed (TABLE 3) for protein production under "non-inducing" conditions (glucose) and "inducing" conditions (glucose/sophorose, or lactose). For example, as shown in FIG. 7, Applicant evaluated total protein production with the first set of six (6) strains expressing (Ace3-LC) C-terminal variants, wherein the parental control strain (RL-P37) can only produce a high amount of protein on lactose (i.e., under "inducing" conditions) and produced a minimal basal level of protein on glucose (i.e., under "non-inducing" conditions). Likewise, as presented in FIG. 7, daughter cells expressing (Ace3-LC) C-terminal variants with a ten (10) amino acid deletion (Cterm-10), an eleven (11) amino acid deletion (Cterm-11), or a fifteen (15) amino acid deletion (Cterm-15), demonstrated an increase in protein production under both lactose ("inducing" conditions) and glucose ("non-inducing" conditions). For example, as shown in FIG. 7, the fold change increase is approximately 1.8× on glucose, relative to the protein level produced by the parental strain (RL-P37) on lactose, and 3× on lactose relative to the protein level produced by the parental strain (RL-P37) on lactose.

In contrast, as indicated in FIG. 7, the wild-type (Ace3-LC) C-terminus (i.e., comprising zero (0) amino acids deleted; SEQ ID NO: 2) and the (Ace3-LC) C-terminal variants comprising twenty (20) amino acids deleted (SEQ ID NO: 21), or twenty-five (25) amino acids deleted (SEQ ID NO: 22) demonstrated a significantly reduced total protein production both on lactose and glucose. These results demonstrate that truncation of the wild-type (Ace3-LC) C-terminus is essential for its function in up-regulating protein production, and that there is an upper and lower limit to the number of amino acid truncations permitted at the Ace3 C-terminus.

To further explore the upper and lower limits of permissible amino acid deletions in wild-type (Ace3-LC) C-terminus, Applicant screened the *T. reesei* strains comprising C-terminal deletions ranging from six (6) amino acid deletions to nineteen (19) amino acid deletions, using a one (1) amino acid deletion increment (e.g., see TABLE 1, set 2; and TABLE 3). For example, as presented in FIG. 8, truncation of five (5) or six (6) C-terminal amino acids showed similar results as the parental strain (i.e., basal protein production on glucose, and higher production on lactose). In contrast, deletion (truncation) of at least the last seven (7) amino acids of the C-terminus (FIG. 5), and deletions (truncations) up to, and including seventeen (17) amino acids (FIG. 5), showed improved production under both glucose (non-inducing) conditions and lactose (inducing) conditions, as shown in FIG. 8.

For example, *T. reesei* strains expressing (Ace3-LC) C-terminal variants C-term-7 (SEQ ID NO: 9), C-term-8 (SEQ ID NO: 10), C-term-9 (SEQ ID NO: 11), C-term-10 (SEQ ID NO: 12), C-term-12 (SEQ ID NO:13), C-term-13 (SEQ ID NO:14), C-term-14 (SEQ ID NO:15), C-term-15 (SEQ ID NO:16), C-term-16 (SEQ ID NO:17) and C-term-17 (SEQ ID NO:18), demonstrated an approximately 2-fold increase in total protein production under glucose (non-inducing) conditions compared to the parental strain RL-P37 on lactose, and an approximately 3-fold increase in total protein production under lactose (inducing) conditions compared to the parental strain RL-P37 on lactose. In contrast, *T. reesei* strains expressing the wild-type Ace3-LC protein (i.e. comprising a wild-type Ace3 C-terminus; SEQ ID NO: 2) produced a reduced amount of protein on lactose than the parental strain RL-P37 on lactose, and a minimal amount on glucose (FIG. 8). *T. reesei* strains expressing (Ace3-LC) C-terminal variants having less than a seven (7) amino acid deletion at the C-terminus produced comparable amount of protein on glucose and on lactose as the parental strain RL-P37 under the same conditions. *T. reesei* strains expressing (Ace3-LC) C-terminal variants comprising more than a seventeen (17) amino acid deletion at the C-terminus, produced a minimal amount of protein under either glucose or lactose conditions (FIG. 8).

As set forth below in Example 2, Applicant has molecularly reverted the C-terminal truncation point mutation at the ace3 locus (i.e., encoding Ace3-L; SEQ ID NO: 6) back to the wild type (Ace3) C-terminal sequence of QM6a (i.e., encoding Ace3-LC) ending in (G) glycine (FIG. 1B; SEQ ID NO: 2). More particularly, as described in Example 2 and presented in FIG. 9, Applicant evaluated three (3) strains in shake flask fermentations for their protein production, which included strains "T4abc" (comprising the ace3 truncation allele encoding Ace3-L; SEQ ID NO: 6), "T4abc ace3 rev" (comprising the ace3 full-length allele encoding Ace3-LC; SEQ ID NO: 2), and "T4abc del-cbh1" (comprising a deletion of its endogenous cellobiohydrolase (cbh1) gene). As shown in FIG. 9, the total secreted protein titer decreased approximately 73% when the ace3 mutation (Ace3-L; SEQ ID NO: 6) was reverted in the T4abc background such that it encoded the wild-type (full-length) Ace3 C-terminus (Ace3-LC ending in glycine (G); SEQ ID NO: 2). For comparison, deletion of the gene (cbh1) encoding the most prominent secreted protein (Cbh1) reduced the total secreted protein titer by only 47%.

In addition to the native Ace3 C-terminal truncations (deletions) described above, Applicant has contemplated, constructed, tested and verified certain other Ace3 C-terminal modifications described herein. More particularly, without wishing to be bound by any particular thereof, mechanism, or mode of operation, Applicant contemplates that other genetic modifications of the Ace3 C-terminus (e.g., substitutions, insertions, internal (C-terminal) deletions, and combinations thereof) are equally suitable genetic modifications for improving protein productivity as described herein. For example, as set forth below in Example 3, Applicant describes compositions and methods for constructing Ace3 TF C-terminal variant libraries and screening such libraries for improved protein productivity in *Tricho-derma* sp. cells. The C-terminal variant libraries for Ace3 are generated by modification of the coding sequence of the full-length (wild-type) Ace3-LC C-terminus coding for amino acids positions 641 through 689 of SEQ ID NO: 2. For example, FIG. 15 (SEQ ID NO: 30) presents the full-length (wild-type) Ace3-LC C-terminus coding for amino acids positions S641 through G689. More specifi-cally, Applicant describes three (3) different Ace3 C-termi-nal libraries including, a site substitution library (Library 1), a scanning insertion library (Library 2) and a scanning deletion library (Library 3).

Example 4 of the disclosure describes the molecular substitution of the last eleven (11) amino acid residues of the Ace3-LC protein's C-terminus, with either a V5 epitope tag, or a V5-(6×His) tandem tag, wherein *Trichoderma* sp. strains expressing the Ace3-LC protein with the C-terminal V5 tag substitutions (i.e., Ace3-LC-V5) or expressing the Ace3-LC protein with the C-terminal V5-(6×His) tandem tag substitutions (i.e., Ace3 LC-V5-(6×His)) were tested (fermented) under both "non-inducing" (Glu) and "induc-ing" (Glu/Sop) conditions.

For example, modified (daughter) *T. reesei* cells compris-ing and expressing the variant Ace3-L TF protein (SEQ ID NO: 6) comprising the eleven (11) amino acid truncation produced high amounts of secreted protein, under both inducing (Glu/Sop) and non-inducing (Glu) conditions. In addition, the modified (daughter) *T. reesei* cells comprising and expressing Ace3-LC-V5 (i.e., comprising a fourteen (14) amino acid substitution of the last eleven (11) amino acids) and the variant (daughter) *T. reesei* cells comprising and expressing Ace3-LC-V5-(6×His) (i.e., comprising a twenty-three (23) amino acid substitution of the last eleven (11) amino acids) also demonstrated high protein produc-tivities (see, FIG. 14) under both inducing (Glu/Sop) and non-inducing (Glu) conditions, albeit of approximately 10% lower than the Ace3-L variant. Thus, these results demon-strate that genetic modifications of the Ace3 C-terminus including, but not limited to, substitutions, insertions, inter-nal (C-terminal) deletions, and combinations thereof are equally suitable genetic modifications for improving protein productivity as described herein.

IV. Recombinant Nucleic Acids and Molecular Biology

In certain embodiments, the disclosure is directed to isolated polynucleotides (nucleic acid sequences) encoding variant Ace3 TF proteins. In certain embodiments, a variant Ace3 TF comprises at least 90% sequence identity to amino acid positions 1-672 of SEQ ID NO: 2 and comprises a genetic modification of one or more C-terminal amino acid residues selected from positions 673-689 of SEQ ID NO: 2. Certain other embodiments are therefore related to geneti-cally modified *Trichoderma* sp. cells comprising an ace3 gene encoding a variant Ace3 TF protein of the disclosure, wherein the modified cells are capable of producing a protein of interest (POI) in the absence of inducing sub-strates and/or wherein the modified cells are capable of producing an increased amount of a POI in the presence of inducing substrates. In certain embodiments, a "modifica-tion" or "genetic modification" include: (a) the introduction, substitution, or removal of one or more nucleotides in a gene (or an ORF thereof), or the introduction, substitution, or removal of one or more nucleotides in a regulatory element required for the transcription or translation of the gene or ORF thereof, (b) a gene disruption, (c) a gene conversion, (d) a gene deletion, (e) the down-regulation of a gene, (f) specific mutagenesis and/or (g) random mutagenesis of any one or more of the genes disclosed herein.

Thus, in certain embodiments, the disclosure is directed to recombinant nucleic acids comprising a gene or ORF encod-ing an Ace3 protein of the disclosure. In certain embodi-ments, a recombinant nucleic acid comprises a polynucle-otide expression cassette for production of an Ace3 variant protein in a filamentous fungal host cell. In other embodi-ments, the polynucleotide expression cassette is comprised within an expression vector. In certain embodiments, the expression vector is a plasmid.

In certain other embodiments, the recombinant nucleic acid (or polynucleotide expression cassette thereof or expression vector thereof) further comprises one or more selectable markers. Selectable markers for use in filamen-tous fungi include, but are not limited to, alsl, amdS, hygR, pyr2, pyr4, pyrG, sucA, a bleomycin resistance marker, a blasticidin resistance marker, a pyrithiamine resistance marker, a chlorimuron ethyl resistance marker, a neomycin resistance marker, an adenine pathway gene, a tryptophan pathway gene, a thymidine kinase marker and the like. In a particular embodiment, the selectable marker is pyr2, which compositions and methods of use are generally set forth in PCT Publication No. WO2011/153449. Thus, in certain embodiments, a polynucleotide construct encoding an Ace3 variant protein of the disclosure comprises a nucleic acid sequence encoding a selectable marker operably linked thereto.

In another embodiment, the recombinant nucleic acid, polynucleotide construct, polynucleotide expression cassette or expression vector thereof comprises a heterologous pro-moter driving the expression of the gene (or ORF) encoding the variant Ace3 protein. More particularly, in certain embodiments, the heterologous promoter is a constitutive or an inducible promoter. In particular embodiments, a heter-ologous promoter is selected from the group consisting of a rev3 promoter, a bxl promoter, a tkl1 promoter, a PID104295 promoter, a dld1 promoter, a xyn4 promoter, a PID72526 promoter, an axe1 promoter, a hxk1 promoter, a dic1 pro-moter, an opt promoter, a gut1 promoter and a pki1 pro-moter. Thus, in certain embodiments, a recombinant nucleic acid (or polynucleotide construct, polynucleotide expression cassette or expression vector thereof) comprises a promoter sequence which is 5' and operably linked to the nucleic acid sequence encoding the variant Ace3 protein.

In another embodiment, a recombinant nucleic acid (or polynucleotide construct, polynucleotide expression cassette or expression vector thereof) further comprises a nucleic acid sequence encoding a native ace3 terminator sequence. Thus, in certain embodiments, a recombinant nucleic acid (or polynucleotide construct, polynucleotide expression cas-sette, or expression vector thereof) comprises a heterologous promoter which is 5' and operably linked to a nucleic acid sequence encoding the variant Ace3 protein and comprises a native ace3 terminator sequence which is 3' and operably linked to a nucleic acid sequence encoding the variant Ace3 protein (e.g., 5'-Pro-ORF-Term-3', where "Pro" is a consti-tutive promoter, "ORF" encodes Ace3 and "Term" is a native ace3 terminator sequence).

An example of regulatory or control sequences may be a promoter sequence or a functional part thereof, (i.e., a part which is sufficient for affecting expression of the nucleic acid sequence). Other control sequences for modification include, but are not limited to, a leader sequence, a pro-peptide sequence, a signal sequence, a transcription termi-nator, a transcriptional activator and the like.

In certain other embodiments, a gene (or ORF) of interest encoding a protein of interest is placed under the control of a promoter sequence derived from a gene encoding lignocellulosic degrading enzyme. For example, in certain embodiments a gene (or ORF) of interest encoding a protein of interest is placed under the control of a cbh1 promoter, such that the expression of the GOI is upregulated in the presence of a variant Ace3 TF protein of the disclosure. Thus, in certain embodiments, a promoter sequence derived from a gene encoding lignocellulosic degrading enzyme is, a cellobiohydrolase promoter sequence, an endoglucanase promoter sequence, a β-glucosidase promoter sequence, or a xylanase promoter sequence.

In certain embodiments, a modified *Trichoderma* sp. cell of the disclosure is constructed by reducing or eliminating the expression of a gene of interest (GOI), using methods well known in the art, for example, insertions, disruptions, replacements, or deletions. The portion of the gene to be modified or inactivated may be, for example, the coding region or a regulatory element required for expression of the coding region.

In certain other embodiments, a modified *Trichoderma* sp. cell is constructed by gene deletion to eliminate or reduce the expression of at least one of GOI. Gene deletion techniques enable the partial or complete removal of the gene(s), thereby eliminating their expression, or expressing a non-functional (or reduced activity) protein product. In such methods, the deletion of the gene(s) may be accomplished by homologous recombination using a plasmid that has been constructed to contiguously contain the 5' and 3' regions flanking the gene.

In other embodiments, a modified *Trichoderma* sp. cell of the disclosure is constructed by introducing, substituting, or removing one or more nucleotides in the gene or a regulatory element required for the transcription or translation thereof. For example, nucleotides may be inserted or removed so as to result in the introduction of a stop codon, the removal of the start codon, or a frame-shift of the open reading frame. Such a modification may be accomplished by site-directed mutagenesis or PCR generated mutagenesis in accordance with methods known in the art.

In another embodiment, a modified *Trichoderma* sp. cell is constructed by the process of gene conversion. For example, in the gene conversion method, a nucleic acid sequence corresponding to the gene(s) is mutagenized in vitro to produce a defective nucleic acid sequence, which is then transformed into the parental *Trichoderma* sp. cell to produce a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (Perego, 1993). Alternatively, the defective nucleic acid sequence may contain an insertion, substitution, or deletion of one or more nucleotides of the gene, as described below.

In other embodiments, a modified *Trichoderma* sp. cell is constructed by established anti-sense techniques using a nucleotide sequence complementary to the nucleic acid sequence of the gene (Parish and Stoker, 1997). More specifically, expression of the gene by a *Trichoderma* sp. cell may be reduced (down-regulated) or eliminated by introducing a nucleotide sequence complementary to the nucleic acid sequence of the gene, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. Such anti-sense methods include, but are not limited to RNA interference (RNAi), small interfering RNA (siRNA), microRNA (miRNA), antisense oligonucleotides, and the like, all of which are well known to the skilled artisan.

In other embodiments, a modified *Trichoderma* sp. cell is produced/constructed via CRISPR-Cas9 editing. For example, a gene of interest can be disrupted (or deleted or down-regulated) by means of nucleic acid guided endonucleases, that find their target DNA by binding either a guide RNA (e.g., Cas9) and Cpf1 or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to disrupt or delete the gene. For example, the gene encoding the nucleic acid guided endonuclease (for this purpose Cas9 from *S. pyogenes*) or a codon optimized gene encoding the Cas9 nuclease is operably linked to a promoter active in the *Trichoderma* sp. cell and a terminator active in a *Trichoderma* sp. cell, thereby creating a *Trichoderma* Cas9 expression cassette. Likewise, one or more target sites unique to the gene of interest are readily identified by a person skilled in the art. For example, to build a DNA construct encoding a gRNA-directed to a target site within the gene of interest, the variable targeting domain (VT) will comprise nucleotides of the target site which are 5' of the (PAM) protospacer adjacent motif (TGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a *Trichoderma* sp. expression cassette for the gRNA is created by operably linking the DNA encoding the gRNA to a promoter active in *Trichoderma* cells and a terminator active in *Trichoderma* cells.

In certain embodiments, the DNA break induced by the endonuclease is repaired/replaced with an incoming sequence. For example, to precisely repair the DNA break generated by the Cas9 expression cassette and the gRNA expression cassette described above, a nucleotide editing template is provided, such that the DNA repair machinery of the cell can utilize the editing template. For example, about 500 bp 5' of targeted gene can be fused to about 500 bp 3' of the targeted gene to generate an editing template, which template is used by the *Trichoderma* host's machinery to repair the DNA break generated by the RNA-guided endonuclease (RGEN).

The Cas9 expression cassette, the gRNA expression cassette and the editing template can be co-delivered to filamentous fungal cells using many different methods (e.g., protoplast fusion, electroporation, natural competence, or induced competence). The transformed cells are screened by PCR amplifying the target gene locus, by amplifying the locus with a forward and reverse primer. These primers can amplify the wild-type locus or the modified locus that has been edited by the RGEN.

In yet other embodiments, a modified *Trichoderma* sp. cell is constructed by random or specific mutagenesis using methods well known in the art, including, but not limited to, chemical mutagenesis and transposition. Modification of the gene may be performed by subjecting the parental cell to mutagenesis and screening for mutant cells in which expression of the gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods. Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the gene.

Thus, in certain embodiments, standard techniques for transformation of filamentous fungi and culturing the fungi (which are well known to one skilled in the art) are used to transform a fungal host cell of the disclosure. Thus, the introduction of a DNA construct or vector into a fungal host cell includes techniques such as transformation, electroporation, nuclear microinjection, transduction, transfection (e.g., lipofection mediated and DEAE-Dextrin mediated transfection), incubation with calcium phosphate DNA precipitate, high velocity bombardment with DNA-coated microprojectiles, gene gun or biolistic transformation, protoplast fusion and the like. General transformation techniques are known in the art (see, e.g., Ausubel et al., 1987, Sambrook et al., 2001 and 2012, and Campbell et al., 1989). The expression of heterologous proteins in *Trichoderma* is described, for example, in U.S. Pat. Nos. 6,022,725; 6,268, 328; Harkki et al., 1991 and Harkki et al., 1989. Reference is also made to Cao et al. (2000), for transformation of *Aspergillus* strains.

Generally, transformation of *Trichoderma* sp. uses protoplasts or cells that have been subjected to a permeability treatment, typically at a density of $10^5$ to $10^7$/mL, particularly $2\times10^6$/mL. A volume of 100 µL of these protoplasts or cells in an appropriate solution (e.g., 1.2 M sorbitol and 50 mM $CaCl_2$) is mixed with the desired DNA. Generally, a high concentration of polyethylene glycol (PEG) is added to the uptake solution. Additives, such as dimethyl sulfoxide, heparin, spermidine, potassium chloride and the like, may also be added to the uptake solution to facilitate transformation. Similar procedures are available for other fungal host cells. See, e.g., U.S. Pat. Nos. 6,022,725 and 6,268,328, both of which are incorporated by reference.

In certain embodiments, the instant disclosure is directed to the expression and production of one or more proteins of interest which are endogenous to the filamentous fungal host cell (i.e., the endogenous proteins are produced by a variant fungal host cell of the disclosure comprising a genetic modification which expresses a variant Ace3 protein). In other embodiments, the disclosure is directed to expressing and producing one or more proteins of interest which are heterologous to the to the filamentous fungal host cell. Therefore, the instant disclosure generally relies on routine techniques in the field of recombinant genetics. Basic texts disclosing the general methods of use in present disclosure include Sambrook et al., (2nd Edition, 1989); Kriegler (1990) and Ausubel et al., (1994).

Thus, in certain embodiments, a heterologous gene or ORF encoding a protein of interest is introduced into a filamentous fungal (host) cell. In certain embodiments, the heterologous gene or ORF is typically cloned into an intermediate vector, before being transformed into a filamentous fungal (host) cells for replication and/or expression. These intermediate vectors can be prokaryotic vectors, such as, e.g., plasmids, or shuttle vectors. In certain embodiments, the expression of the heterologous gene or ORF is under the control of its native promoter. In other embodiments, the expression of the heterologous gene or ORF is placed under the control of a heterologous promoter, which can be a heterologous constitutive promoter or a heterologous inducible promoter.

Those skilled in the art are aware that a natural (native) promoter can be modified by replacement, substitution, addition or elimination of one or more nucleotides, without changing its function. The practice of the invention encompasses but is not constrained by such alterations to the promoter.

The expression vector/construct typically contains a transcription unit or expression cassette that contains all the additional elements required for the expression of the heterologous sequence. For example, a typical expression cassette contains a 5' promoter operably linked to the heterologous nucleic acid sequence encoding a protein of interest and may further comprise sequence signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette may also contain a transcription termination region downstream of the structural gene to provide for efficient termination. The termination region may be obtained from the same gene as the promoter sequence or may be obtained from different genes. Although any fungal terminator is likely to be functional in the present invention, preferred terminators include: the terminator from *Trichoderma* cbh1 gene, the terminator from *Aspergillus nidulans* trpC gene (Yelton et al., 1984; Mullaney et al., 1985), the *Aspergillus awamori* or *Aspergillus niger* glucoamylase genes (Nunberg et al., 1984; Boel et al., 1984) and/or the *Mucor miehei* carboxyl protease gene (EPO Publication No. 0215594).

The particular expression vector used to transport the genetic information into the cell is not particularly critical. Any of the conventional vectors used for expression in eukaryotic or prokaryotic cells may be used. Standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

The elements that can be included in expression vectors may also be a replicon, a gene encoding antibiotic resistance to permit selection of bacteria that harbor recombinant plasmids, or unique restriction sites in nonessential regions of the plasmid to allow insertion of heterologous sequences. The particular antibiotic resistance gene chosen is not dispositive either, as any of the many resistance genes known in the art may be suitable. The prokaryotic sequences are preferably chosen such that they do not interfere with the replication or integration of the DNA in *Trichoderma reesei*.

The methods of transformation of the present invention may result in the stable integration of all or part of the transformation vector into the genome of the filamentous fungus. However, transformation resulting in the maintenance of a self-replicating extra-chromosomal transformation vector is also contemplated.

Any of the known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other known methods for introducing cloned genomic DNA, cDNA, synthetic DNA or other foreign genetic material into a host cell (see, e.g., Sambrook et al., supra). Also of use is the *Agrobacterium*-mediated transfection method such as the one described in U.S. Pat. No. 6,255,115. It is only necessary that the particular genetic engineering procedure used be capable of successfully introducing at least one gene into the host cell capable of expressing the heterologous gene.

After the expression vector is introduced into the cells, the transfected cells are cultured under conditions favoring expression of genes under control of cellulase gene promoter sequences. Large batches of transformed cells can be cultured as described herein. Finally, product is recovered from the culture using standard techniques.

Thus, the disclosure herein provides for the expression and enhanced secretion of desired polypeptides whose expression is under control of cellulase gene promoter sequences including naturally occurring cellulase genes, fusion DNA sequences, and various heterologous constructs. The invention also provides processes for expressing and secreting high levels of such desired.

V. Proteins of Interest

As stated above, certain embodiments of the disclosure are related to genetically modified filamentous fungal cells comprising genetic modifications which expresses a gene or ORF encoding a variant Ace3 protein described herein. More particularly, certain embodiments are related to compositions and methods for the expression/production of proteins of interest (POI) in such modified fungal cells encoding a variant Ace3 protein in the absence of an inducing substrate. Certain other embodiments are related to compositions and methods for the increasing the production of a POI in such modified fungal cells in the presence of an inducing substrate.

As described herein, a protein of interest (POI) includes, but is not limited to, a hemicellulase, a peroxidase, a protease, a cellulase, a xylanase, a lipase, a phospholipase, an esterase, a cutinase, a pectinase, a keratinase, a reductase, an oxidase, a phenol oxidase, a lipoxygenase, a ligninase, a pullulanase, a tannase, a pentosanase, a mannanase, a β-glucanase, a hyaluronidase, a chondroitinase, a laccase, a amylase, a glucoamylase, an acetyl esterase, an aminopeptidase, amylases, an arabinases, an arabinosidase, an arabinofuranosidase, a carboxypeptidase, a catalase, a deoxyribonuclease, an epimerase, an α-galactosidase, a β-galactosidase, an α-glucanases, a glucan lyase, an endo-β-glucanase, a glucose oxidase, a glucuronidase, an invertase, an isomerase, and the like.

Thus, in certain embodiments, a POI is selected from an Enzyme Commission (EC) Number selected from the group consisting of EC 1, EC 2, EC 3, EC 4, EC 5 or EC 6.

For example, in certain embodiments a POI is an oxidoreductase enzyme, including, but not limited to, an EC1 (oxidoreductase) enzyme selected from EC 1.10.3.2 (e.g., a laccase), EC 1.10.3.3 (e.g., L-ascorbate oxidase), EC 1.1.1.1 (e.g., alcohol dehydrogenase), EC 1.11.1.10 (e.g., chloride peroxidase), EC 1.11.1.17 (e.g., peroxidase), EC 1.1.1.27 (e.g., L-lactate dehydrogenase), EC 1.1.1.47 (e.g., glucose 1-dehydrogenase), EC 1.1.3.X (e.g., glucose oxidase), EC 1.1.3.10 (e.g., pyranose oxidase), EC 1.13.11.X (e.g., dioxygenase), EC 1.13.11.12 (e.g., lineolate 13S-lipoxygenase), EC 1.1.3.13 (e.g., alcohol oxidase), EC 1.14.14.1 (e.g., monooxygenase), EC 1.14.18.1 (e.g., monophenol monooxigenase), EC 1.15.1.1 (e.g., superoxide dismutase), EC 1.1.5.9 (formerly EC 1.1.99.10, e.g., glucose dehydrogenase), EC 1.1.99.18 (e.g., cellobiose dehydrogenase), EC 1.1.99.29 (e.g., pyranose dehydrogenase), EC 1.2. 1.X (e.g., fatty acid reductase), EC 1.2.1.10 (e.g., acetaldehyde dehydrogenase), EC 1.5.3.X (e.g., fructosyl amine reductase), EC 1.8. 1.X (e.g., disulfide reductase) and EC 1.8.3.2 (e.g., thiol oxidase).

In certain embodiments a POI is a transferase enzyme, including, but not limited to, an EC 2 (transferase) enzyme selected from EC 2.3.2.13 (e.g., transglutaminase), EC 2.4. 1.X (e.g., hexosyltransferase), EC 2.4.1.40 (e.g., altemasucrase), EC 2.4.1.18 (e.g., 1,4 alpha-glucan branching enzyme), EC 2.4.1.19 (e.g., cyclomaltodextrin glucanotransferase), EC 2.4.1.2 (e.g., dextrin dextranase), EC 2.4.1.20 (e.g., cellobiose phosphorylase), EC 2.4.1.25 (e.g., 4-alpha-glucanotransferase), EC 2.4.1.333 (e.g., 1,2-beta-oligoglucan phosphor transferase), EC 2.4.1.4 (e.g., amylosucrase), EC 2.4.1.5 (e.g., dextransucrase), EC 2.4.1.69 (e.g., galactoside 2-alpha-L-fucosyl transferase), EC 2.4.1.9 (e.g., inulosucrase), EC 2.7.1.17 (e.g., xylulokinase), EC 2.7.7.89 (formerly EC 3.1.4.15, e.g., [glutamine synthetase]-adenylyl-L-tyrosine phosphorylase), EC 2.7.9.4 (e.g., alpha glucan kinase) and EC 2.7.9.5 (e.g., phosphoglucan kinase).

In other embodiments a POI is a hydrolase enzyme, including, but not limited to, an EC 3 (hydrolase) enzyme selected from EC 3.1.X.X (e.g., an esterase), EC 3.1.1.1 (e.g., pectinase), EC 3.1.1.14 (e.g., chlorophyllase), EC 3.1.1.20 (e.g., tannase), EC 3.1.1.23 (e.g., glycerol-ester acylhydrolase), EC 3.1.1.26 (e.g., galactolipase), EC 3.1.1.32 (e.g., phospholipase A1), EC 3.1.1.4 (e.g., phospholipase A2), EC 3.1.1.6 (e.g., acetylesterase), EC 3.1.1.72 (e.g., acetylxylan esterase), EC 3.1.1.73 (e.g., feruloyl esterase), EC 3.1.1.74 (e.g., cutinase), EC 3.1.1.86 (e.g., rhamnogalacturonan acetylesterase), EC 3.1.1.87 (e.g., fumosin B1 esterase), EC 3.1.26.5 (e.g., ribonuclease P), EC 3.1.3.X (e.g., phosphoric monoester hydrolase), EC 3.1.30.1 (e.g., *Aspergillus* nuclease S1), EC 3.1.30.2 (e.g., *Serratia marcescens* nuclease), EC 3.1.3.1 (e.g., alkaline phosphatase), EC 3.1.3.2 (e.g., acid phosphatase), EC 3.1.3.8 (e.g., 3-phytase), EC 3.1.4.1 (e.g., phosphodiesterase I), EC 3.1.4.11 (e.g., phosphoinositide phospholipase C), EC 3.1.4.3 (e.g., phospholipase C), EC 3.1.4.4 (e.g., phospholipase D), EC 3.1.6.1 (e.g., arylsufatase), EC 3.1.8.2 (e.g., diisopropyl-fluorophosphatase), EC 3.2.1.10 (e.g., oligo-1, 6-glucosidase), EC 3.2.1.101 (e.g., mannanendo-1,6-alpha-mannosidase), EC 3.2.1.11 (e.g., alpha-1,6-glucan-6-glucanohydrolase), EC 3.2.1.131 (e.g., xylan alpha-1,2-glucuronosidase), EC 3.2.1.132 (e.g., chitosan N-acetylglucosaminohydrolase), EC 3.2.1.139 (e.g., alpha-glucuronidase), EC 3.2.1.14 (e.g., chitinase), EC 3.2.1.151 (e.g., xyloglucan-specific endo-beta-1,4-glucanase), EC 3.2.1.155 (e.g., xyloglucan-specific exo-beta-1,4-glucanase), EC 3.2.1.164 (e.g., galactan endo-1,6-beta-galactosidase), EC 3.2.1.17 (e.g., lysozyme), EC 3.2.1.171 (e.g., rhamnogalacturonan hydrolase), EC 3.2.1.174 (e.g., rhamnogalacturonan rhamnohydrolase), EC 3.2.1.2 (e.g., beta-amylase), EC 3.2.1.20 (e.g., alpha-glucosidase), EC 3.2.1.22 (e.g., alpha-galactosidase), EC 3.2.1.25 (e.g., beta-mannosidase), EC 3.2.1.26 (e.g., beta-fructofuranosidase), EC 3.2.1.37 (e.g., xylan 1,4-beta-xylosidase), EC 3.2.1.39 (e.g., glucan endo-1,3-beta-D-glucosidase), EC 3.2.1.40 (e.g., alpha-L-rhamnosidase), EC 3.2.1.51 (e.g., alpha-L-fucosidase), EC 3.2.1.52 (e.g., beta-N-Acetylhexosaminidase), EC 3.2.1.55 (e.g., alpha-N-arabinofuranosidase), EC 3.2.1.58 (e.g., glucan 1,3-beta-glucosidase), EC 3.2.1.59 (e.g., glucan endo-1,3-alpha-glucosidase), EC 3.2.1.67 (e.g., galacturan 1,4-alpha-galacturonidase), EC 3.2.1.68 (e.g., isoamylase), EC 3.2.1.7 (e.g., 1-beta-D-fructan fructanohydrolase), EC 3.2.1.74 (e.g., glucan 1,4-glucosidase), EC 3.2.1.75 (e.g., glucan endo-1,6-beta-glucosidase), EC 3.2.1.77 (e.g., mannan 1,2-(1,3)-alpha-mannosidase), EC 3.2.1.80 (e.g., fructan beta-fructosidase), EC 3.2.1.82 (e.g., exo-poly-alpha-galacturonosidase), EC 3.2.1.83 (e.g., kappa-carrageenase), EC 3.2.1.89 (e.g., arabinogalactan endo-1,4-beta-galactosidase), EC 3.2.1.91 (e.g., cellulose 1,4-beta-cellobiosidase), EC 3.2.1.96 (e.g., mannosyl-glycoprotein endo-beta-N-acetyl-glucosaminidase), EC 3.2.1.99 (e.g., arabinan endo-1,5-alpha-L-arabinanase), EC 3.4.X.X (e.g., peptidase), EC 3.4.11.X (e.g., aminopeptidase), EC 3.4.11.1 (e.g., leucyl aminopeptidase), EC 3.4.11.18 (e.g., methionyl aminopeptidase), EC 3.4.13.9 (e.g., Xaa-Pro dipeptidase), EC 3.4.14.5 (e.g., dipeptidyl-peptidase IV), EC 3.4.16. X (e.g., serine-type carboxypeptidase), EC 3.4.16.5 (e.g., carboxypeptidase C), EC 3.4.19.3 (e.g., pyroglutamyl-peptidase I), EC 3.4.21. X (e.g., serine endopeptidase), EC 3.4.21.1 (e.g., chymotrypsin), EC 3.4.21.19 (e.g., glutamyl endopeptidase), EC 3.4.21.26 (e.g., prolyl obgopeptidase), EC 3.4.21.4 (e.g., trypsin), EC 3.4.21.5 (e.g., thrombin), EC 3.4.21.63 (e.g., oryzin), EC 3.4.21.65 (e.g., thermomycolin), EC 3.4.21.80 (e.g., streptogrisin A), EC 3.4.22. X (e.g., cysteine endopeptidase), EC 3.4.22.14 (e.g., actinidain), EC 3.4.22.2 (e.g., papain), EC 3.4.22.3 (e.g., ficain), EC 3.4.22.32 (e.g., stem bromelain), EC 3.4.22.33 (e.g., fruit bromelain), EC 3.4.22.6 (e.g., chymopapain), EC 3.4.23.1 (e.g., pepsin A), EC 3.4.23.2 (e.g., pepsin B), EC 3.4.23.22 (e.g., endothiapepsin), EC 3.4.23.23 (e.g., mucorpepsin), EC 3.4.23.3 (e.g., gastricsin), EC 3.4.24.X (e.g., metalloendopeptidase), EC 3.4.24.39 (e.g., deuterolysin), EC 3.4.24.40 (e.g., serralysin), EC 3.5.1.1 (e.g., asparaginase), EC 3.5.1.11 (e.g., penicillin amidase), EC 3.5.1.14 (e.g., N-acyl-aliphatic-L-amino acid amidohydrolase), EC 3.5.1.2 (e.g., L-glutamine amidohydrolase), EC 3.5.1.28 (e.g., N-acetylmuramoyl-L-alanine amidase), EC 3.5.1.4 (e.g., amidase), EC 3.5.1.44 (e.g., protein-L-glutamine amidohydrolase), EC 3.5.1.5 (e.g., urease), EC 3.5.1.52 (e.g., peptide-N(4)-(N-acetyl-beta-glucosaminyl)asparagine amidase), EC 3.5.1.81 (e.g., N-Acyl-D-amino-acid deacylase), EC 3.5.4.6 (e.g., AMP deaminase) and EC 3.5.5.1 (e.g., nitrilase).

In other embodiments a POI is a lyase enzyme, including, but not limited to, an EC 4 (lyase) enzyme selected from EC 4.1.2.10 (e.g., mandelonitrile lyase), EC 4.1.3.3 (e.g., N-acetylneuraminate lyase), EC 4.2.1.1 (e.g., carbonate dehydratase), EC 4.2.2.—(e.g., rhamnogalacturonanlyase), EC 4.2.2.10 (e.g., pectin lyase), EC 4.2.2.22 (e.g., pectate trisaccharide-lyase), EC 4.2.2.23 (e.g., rhamnogalacturonan endolyase) and EC 4.2.2.3 (e.g., mannuronate-specific alginate lyase).

In certain other embodiments a POI is an isomerase enzyme, including, but not limited to, an EC 5 (isomerase) enzyme selected from EC 5.1.3.3 (e.g., aldose 1-epimerase), EC 5.1.3.30 (e.g., D-psicose 3-epimerase), EC 5.4.99.11

(e.g., isomaltulose synthase) and EC 5.4.99.15 (e.g., (1 4)-a-D-glucan 1-a-D-glucosylmutase).

In yet other embodiments, a POI is a ligase enzyme, including, but not limited to, an EC 6 (ligase) enzyme selected from EC 6.2.1.12 (e.g., 4-coumarate:coenzyme A ligase) and EC 6.3.2.28 (e.g., L-amino-acid alpha-ligase).

Optimal conditions for the production of the proteins will vary with the choice of the host cell, and with the choice of the protein(s) to be expressed. Such conditions may be readily ascertained by one skilled in the art through routine experimentation and/or optimization.

The protein of interest can be purified or isolated after expression. The protein of interest may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the protein of interest may be purified using a standard anti-protein of interest antibody column. Ultrafiltration and diafiltration techniques, in conjunction with protein concentration, are also useful. The degree of purification necessary will vary depending on the intended use of the protein of interest. In certain instances, no purification of the protein will be necessary.

In certain other embodiments, to confirm that a genetically modified fungal cell of the disclosure produces an increased level of a protein of interest, various methods of screening may be performed. The expression vector may encode a polypeptide fusion to the target protein which serves as a detectable label or the target protein itself may serve as the selectable or screenable marker. The labeled protein may be detected via western blotting, dot blotting (methods available at the Cold Spring Harbor Protocols website), ELISA, or, if the label is GFP, whole cell fluorescence or FACS. For example, a 6-histidine tag would be included as a fusion to the target protein, and this tag would be detected by western blotting. If the target protein expresses at sufficiently high levels, SDS-PAGE combined with Coomassie/silver staining, may be performed to detect increases in variant host cell expression over parental (control) cell, in which case no label is necessary. In addition, other methods may be used to confirm the improved level of a protein of interest, such as, the detection of the increase of protein activity or amount per cell, protein activity or amount per milliliter of medium, allowing cultures or fermentations to continue efficiently for longer periods of time, or through a combination of these methods.

The detection of specific productivity is another method to evaluate the protein production. Specific productivity (Qp) can be determined by the following equation:

$$Qp = gP/gDCW \cdot hr$$

wherein "gP" is grams of protein produced in the tank, "gDCW" is grams of dry cell weight (DCW) in the tank, "hr" is fermentation time in hours from the time of inoculation, which include the time of production as well as growth time.

VI. Fermentation

In certain embodiments, the present disclosure provides methods of producing a protein of interest comprising fermenting a modified fungal cell, wherein the variant fungal cell secrets the protein of interest. In general, fermentation methods well known in the art are used to ferment the variant fungal cells. In some embodiments, the fungal cells are grown under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within batch cultures, cells progress through a static lag phase to a high growth log phase and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Certain embodiments of the instant disclosure are related to fermentation procedures for culturing fungi. Fermentation procedures for production of cellulase enzymes are known in the art. For example, cellulase enzymes can be produced either by solid or submerged culture, including batch, fed-batch and continuous-flow processes. Culturing is generally accomplished in a growth medium comprising an aqueous mineral salts medium, organic growth factors, a carbon and energy source material, molecular oxygen, and, of course, a starting inoculum of the filamentous fungal host to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation media.

The composition of the aqueous mineral medium can vary over a wide range, depending in part on the microorganism and substrate employed, as is known in the art. The mineral media should include, in addition to nitrogen, suitable amounts of phosphorus, magnesium, calcium, potassium, sulfur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

The fermentation reaction is an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion.

The fermentation temperature can vary somewhat, but for filamentous fungi such as *Trichoderma reesei*, the temperature generally will be within the range of about 20° C. to 40° C., generally preferably in the range of about 25° C. to 34° C.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. With filamentous fungi, the pH normally is within the range of about 2.5 to 8.0; with *Trichoderma reesei*, the pH normally is within the range of about 3.0 to 7.0. Preferences for pH range of microorganisms are dependent on the media employed to some extent, as well as the particular microorganism, and thus change somewhat with change in media as can be readily determined by those skilled in the art.

Preferably, the fermentation is conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily washed off. It may be a problem, however, in the case of non-water-soluble substrates, and require added product-treatment steps such as suitable washing steps.

As described above, the time to reach this level is not critical and may vary with the particular microorganism and fermentation process being conducted. However, it is well known in the art how to determine the carbon source concentration in the fermentation medium and whether or not the desired level of carbon source has been achieved.

The fermentation can be conducted as a batch or continuous operation, fed batch operation is much to be preferred for ease of control, production of uniform quantities of products, and most economical uses of all equipment.

If desired, part or all of the carbon and energy source material and/or part of the assimilable nitrogen source such as ammonia can be added to the aqueous mineral medium prior to feeding the aqueous mineral medium to the fermenter.

Each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermenter, cell density measurable by dry cell weights, light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermenter employed is not critical.

The collection and purification of (e.g., cellulase) enzymes from the fermentation broth can also be done by procedures known to one of skill in the art. The fermentation broth will generally contain cellular debris, including cells, various suspended solids and other biomass contaminants, as well as the desired cellulase enzyme product, which are preferably removed from the fermentation broth by means known in the art.

Suitable processes for such removal include conventional solid-liquid separation techniques such as, e.g., centrifugation, filtration, dialysis, microfiltration, rotary vacuum filtration, or other known processes, to produce a cell-free filtrate. It may be preferable to further concentrate the fermentation broth or the cell-free filtrate prior to crystallization using techniques such as ultrafiltration, evaporation or precipitation.

Precipitating the proteinaceous components of the supernatant or filtrate may be accomplished by means of a salt, e.g., ammonium sulfate, followed by purification by a variety of chromatographic procedures, e.g., ion exchange chromatography, affinity chromatography or similar art recognized procedures.

VII. Exemplary Embodiments

Certain exemplary embodiments include:
1. An isolated polynucleotide encoding a variant Ace3 transcription factor (TF) protein, wherein the variant Ace3 TF comprises at least 90% sequence identity to amino acid positions 1-672 of SEQ ID NO: 2 and comprises a genetic modification of one or more C-terminal amino acid residues selected from positions 673-689 of SEQ ID NO: 2.
2. The polynucleotide of embodiment 1, wherein variant Ace3 TF comprises a functional N-terminal binuclear zinc cluster ($Zn_2Cys_6$) DNA binding domain comprising at least 95% sequence identity to SEQ ID NO: 29.
3. The polynucleotide of embodiment 1, wherein the genetic modification of one or more C-terminal amino acid residues selected from positions 673-689 of SEQ ID NO: 2 is an amino acid deletion, an amino acid insertion, an amino acid substitution, or a combination thereof.
4. The polynucleotide of embodiment 3, wherein the genetic modification of one or more C-terminal amino acid residues comprises a deletion of at least the last seven (7) C-terminal amino acid positions 683-689 of SEQ ID NO: 2.
5. The polynucleotide of embodiment 3, wherein the genetic modification of one or more C-terminal amino acid residues comprises a deletion of at least the last eight (8) C-terminal amino acid positions 682-689 of SEQ ID NO: 2.
6. The polynucleotide of embodiment 3, wherein the genetic modification of one or more C-terminal amino acid residues comprises a deletion of at least the last nine (9) C-terminal amino acid positions 681-689 of SEQ ID NO: 2.
7. The polynucleotide of embodiment 3, wherein the genetic modification of one or more C-terminal amino acid residues comprises a deletion of at least the last ten (10) C-terminal amino acid positions 680-689 of SEQ ID NO: 2.
8. The polynucleotide of embodiment 3, wherein the genetic modification of one or more C-terminal amino acid residues comprises a deletion of at least the last eleven (11) C-terminal amino acid positions 679-689 of SEQ ID NO: 2.
9. The polynucleotide of embodiment 3, wherein the genetic modification of one or more C-terminal amino acid residues comprises a deletion of at least the last twelve (12) C-terminal amino acid positions 678-689 of SEQ ID NO: 2.
10. The polynucleotide of embodiment 3, wherein the genetic modification of one or more C-terminal amino acid residues comprises a deletion of at least the last thirteen (13) C-terminal amino acid positions 677-689 of SEQ ID NO: 2.
11. The polynucleotide of embodiment 3, wherein the genetic modification of one or more C-terminal amino acid residues comprises a deletion of at least the last fourteen (14) C-terminal amino acid positions 676-689 of SEQ ID NO: 2.
12. The polynucleotide of embodiment 3, wherein the genetic modification of one or more C-terminal amino acid residues comprises a deletion of at least the last fifteen (15) C-terminal amino acid positions 675-689 of SEQ ID NO: 2.
13. The polynucleotide of embodiment 3, wherein the genetic modification of one or more C-terminal amino acid residues comprises a deletion of at least the last sixteen (16) C-terminal amino acid positions 674-689 of SEQ ID NO: 2.
14. The polynucleotide of embodiment 3, wherein the genetic modification of one or more C-terminal amino acid residues comprises a deletion of at least the last seventeen (17) C-terminal amino acid positions 673-689 of SEQ ID NO: 2.
15. The polynucleotide of embodiment 3, wherein the variant Ace3 TF comprises an amino acid sequence selected from any one of SEQ ID NO: 9 through SEQ ID NO: 18.

16. The polynucleotide of embodiment 3, wherein the genetic modification of one or more C-terminal amino acid residues selected from positions 673-689 of SEQ ID NO: 2 is a deletion of one or more amino acid residue selected from positions 673-683 of SEQ ID NO: 2.

17. The polynucleotide of embodiment 3, wherein the genetic modification of one or more C-terminal amino acid residues selected from positions 673-689 of SEQ ID NO: 2 is a deletion of two consecutive amino acid residues selected from positions 673-674 of SEQ ID NO: 2, positions 674-675 of SEQ ID NO: 2, positions 675-676 of SEQ ID NO: 2, positions 676-677 of SEQ ID NO: 2, positions 677-678 of SEQ ID NO: 2, positions 678-679 of SEQ ID NO: 2, positions 679-680 of SEQ ID NO: 2, positions 680-681 of SEQ ID NO: 2, positions 681-682 of SEQ ID NO: 2, positions 682-683 of SEQ ID NO: 2 and positions 683-684 of SEQ ID NO: 2.

18. The polynucleotide of embodiment 3, wherein the genetic modification of one or more C-terminal amino acid residues selected from positions 673-689 of SEQ ID NO: 2 is a deletion of three consecutive amino acid residues selected from positions 673-675 of SEQ ID NO: 2, positions 674-676 of SEQ ID NO: 2, positions 675-677 of SEQ ID NO: 2, positions 676-678 of SEQ ID NO: 2, positions 677-679 of SEQ ID NO: 2, positions 678-680 of SEQ ID NO: 2, positions 679-681 of SEQ ID NO: 2, positions 680-682 of SEQ ID NO: 2, positions 681-683 of SEQ ID NO: 2, positions 682-684 of SEQ ID NO: 2 and positions 683-685 of SEQ ID NO: 2.

19. The polynucleotide of embodiment 3, wherein the variant Ace3 TF comprises a substitution of one or more C-terminal amino acid residues selected from amino acid positions 672-683 of SEQ ID NO: 2.

20. The polynucleotide of embodiment 19 wherein the variant Ace3 TF further comprises a deletion of at least the last seven (7) C-terminal amino acid positions 683-689 of SEQ ID NO: 2.

21. The polynucleotide of embodiment 3, wherein the variant Ace3 TF comprises an insertion of one or more amino acid residues at a C-terminal amino acid position selected from amino acid positions 673-683 of SEQ ID NO: 2.

22. An isolated *Trichoderma* sp. mutant cell comprising a mutated ace3 gene encoding a variant Ace3 transcription factor (TF) protein, wherein the variant Ace3 TF protein comprises at least 90% sequence identity to amino acid positions 1-672 of SEQ ID NO: 2 and comprises one or more mutated C-terminal amino acid residues selected from positions 673-689 of SEQ ID NO:2.

23. The mutant cell of embodiment 22, wherein the variant Ace3 TF protein upregulates the expression of a gene encoding a lignocellulosic degrading enzyme in the absence of an inducing substrate, when the mutant cell is fermented under suitable conditions for the production of a lignocellulosic degrading enzyme.

24. The mutant cell of embodiment 23, wherein the lignocellulosic degrading enzyme is selected from the group consisting of a cellobiohydrolase, an endoglucanase and a β-glucosidase.

25. The mutant cell of embodiment 22, wherein the variant Ace3 TF protein comprises a functional N-terminal binuclear zinc cluster DNA binding domain comprising at least 95% sequence identity to SEQ ID NO: 29.

26. The mutant cell of embodiment 22, comprising an introduced expression cassette encoding a protein of interest (POI), wherein the introduced cassette comprises an upstream (5') promoter sequence derived from a gene encoding lignocellulosic degrading enzyme operably linked to a downstream (3') open reading frame (ORF) sequence encoding a POI.

27. The mutant cell of embodiment 22, wherein the one or more mutated C-terminal amino acid residues selected from positions 673-689 of SEQ ID NO: 2 comprises an amino acid deletion, an amino acid insertion, an amino acid substitution, or a combination thereof.

28. The mutant cell of embodiment 26, wherein the mutant cell is capable of producing the POI in the absence of an inducing substrate when fermented under suitable conditions for the production of the POI.

29. A protein of interest (POI) produced by the mutant cell of any one of embodiments 22-28.

30. A genetically modified *Trichoderma* sp. fungal cell derived from a parental *Trichoderma* sp. cell comprising an ace3 gene encoding an Ace3 transcription factor (TF) protein comprising at least 90% sequence identity to SEQ ID NO: 2, wherein the genetically modified cell comprises a modified ace3 gene encoding a variant Ace3 TF protein comprising at least 90% sequence identity to amino acid positions 1-672 of SEQ ID NO: 2 and comprising a genetic modification of one or more C-terminal amino acid residues selected from positions 673-689 of SEQ ID NO: 2.

31. The modified cell of embodiment 30, wherein the Ace3 TF protein comprises a functional N-terminal binuclear zinc cluster DNA binding domain comprising at least 95% sequence identity to SEQ ID NO: 29.

32. The modified cell of embodiment 30, wherein the variant Ace3 TF protein upregulates the expression of a gene encoding a lignocellulosic degrading enzyme in the absence of an inducing substrate, when fermented under suitable conditions for the production of a lignocellulosic degrading enzyme.

33. The modified cell of embodiment 32, wherein the lignocellulosic degrading enzyme is selected from the group consisting of a cellobiohydrolase, an endoglucanase and a β-glucosidase.

34. The modified cell of embodiment 30, comprising an introduced expression cassette encoding a protein of interest (POI), wherein the introduced cassette comprises an upstream (5') promoter sequence derived from a gene encoding lignocellulosic degrading enzyme operably linked to a downstream (3') open reading frame (ORF) sequence encoding a POI.

35. The modified cell of embodiment 30, wherein the one or more mutated C-terminal amino acid residues selected from positions 673-689 of SEQ ID NO: 2 comprises an amino acid deletion, an amino acid insertion, an amino acid substitution, or a combination thereof.

36. The modified cell of embodiment 34, wherein the modified cell produces the POI in the absence of an inducing substrate when fermented under suitable conditions for the production of the POI.

37. The modified cell of embodiment 34, wherein the modified cell produces an increased amount of the POI in the presence of an inducing substrate relative to the amount of the same POI produced by the parental cell when fermented under identical conditions for the production of a POI in the presence of an inducing substrate.

38. The modified cell of embodiment 35, wherein the one or more mutated C-terminal amino acid residues selected from positions 673-689 of SEQ ID NO: 2 comprises a deletion of at least the last seven (7) C-terminal amino acid positions 683-689 of SEQ ID NO: 2.

39. The modified cell of embodiment 35, wherein the one or more mutated C-terminal amino acid residues selected from positions 673-689 of SEQ ID NO: 2 comprises a deletion of at least the last eight (8) C-terminal amino acid positions 682-689 of SEQ ID NO: 2.

40. The modified cell of embodiment 35, wherein the one or more mutated C-terminal amino acid residues selected from positions 673-689 of SEQ ID NO: 2 comprises a deletion of at least the last nine (9) C-terminal amino acid positions 681-689 of SEQ ID NO: 2.

41. The modified cell of embodiment 35, wherein the one or more mutated C-terminal amino acid residues selected from positions 673-689 of SEQ ID NO: 2 comprises a deletion of at least the last ten (10) C-terminal amino acid positions 680-689 of SEQ ID NO: 2.

42. The modified cell of embodiment 35, wherein the one or more mutated C-terminal amino acid residues selected from positions 673-689 of SEQ ID NO: 2 comprises a deletion of at least the last eleven (11) C-terminal amino acid positions 679-689 of SEQ ID NO: 2.

43. The modified cell of embodiment 35, wherein the one or more mutated C-terminal amino acid residues selected from positions 673-689 of SEQ ID NO: 2 comprises a deletion of at least the last twelve (12) C-terminal amino acid positions 678-689 of SEQ ID NO: 2.

44. The modified cell of embodiment 35, wherein the one or more mutated C-terminal amino acid residues selected from positions 673-689 of SEQ ID NO: 2 comprises a deletion of at least the last thirteen (13) C-terminal amino acid positions 677-689 of SEQ ID NO: 2.

45. The modified cell of embodiment 35, wherein the one or more mutated C-terminal amino acid residues selected from positions 673-689 of SEQ ID NO: 2 comprises a deletion of at least the last fourteen (14) C-terminal amino acid positions 676-689 of SEQ ID NO: 2.

46. The modified cell of embodiment 35, wherein the one or more mutated C-terminal amino acid residues selected from positions 673-689 of SEQ ID NO: 2 comprises a deletion of at least the last fifteen (15) C-terminal amino acid positions 675-689 of SEQ ID NO: 2.

47. The modified cell of embodiment 35, wherein the one or more mutated C-terminal amino acid residues selected from positions 673-689 of SEQ ID NO: 2 comprises a deletion of at least the last sixteen (16) C-terminal amino acid positions 674-689 of SEQ ID NO: 2.

48. The modified cell of embodiment 35, wherein the one or more mutated C-terminal amino acid residues selected from positions 673-689 of SEQ ID NO: 2 comprises a deletion of at least the last seventeen (17) C-terminal amino acid positions 673-689 of SEQ ID NO: 2.

49. The modified cell of embodiment 35, wherein the variant Ace3 TF comprises an amino acid sequence selected from any one of SEQ ID NO: 9 through SEQ ID NO: 18.

50. The modified cell of embodiment 35, wherein the genetic modification of one or more C-terminal amino acid residues selected from positions 673-689 of SEQ ID NO: 2 is a deletion of one or more amino acid residue selected from positions 673-683 of SEQ ID NO: 2.

51. The modified cell of embodiment 35, wherein the genetic modification of one or more C-terminal amino acid residues selected from positions 673-689 of SEQ ID NO: 2 is a deletion of two consecutive amino acid residues selected from positions 673-674 of SEQ ID NO: 2, positions 674-675 of SEQ ID NO: 2, positions 675-676 of SEQ ID NO: 2, positions 676-677 of SEQ ID NO: 2, positions 677-678 of SEQ ID NO: 2, positions 678-679 of SEQ ID NO: 2, positions 679-680 of SEQ ID NO: 2, positions 680-681 of SEQ ID NO: 2, positions 681-682 of SEQ ID NO: 2, positions 682-683 of SEQ ID NO: 2 and positions 683-684 of SEQ ID NO: 2.

52. The modified cell of embodiment 35, wherein the genetic modification of one or more C-terminal amino acid residues selected from positions 673-689 of SEQ ID NO: 2 is a deletion of three consecutive amino acid residues selected from positions 673-675 of SEQ ID NO: 2, positions 674-676 of SEQ ID NO: 2, positions 675-677 of SEQ ID NO: 2, positions 676-678 of SEQ ID NO: 2, positions 677-679 of SEQ ID NO: 2, positions 678-680 of SEQ ID NO: 2, positions 679-681 of SEQ ID NO: 2, positions 680-682 of SEQ ID NO: 2, positions 681-683 of SEQ ID NO: 2, positions 682-684 of SEQ ID NO: 2 and positions 683-685 of SEQ ID NO: 2.

53. The modified cell of embodiment 35, wherein the variant Ace3 TF comprises a substitution of one or more C-terminal amino acid residues selected from amino acid positions 672-683 of SEQ ID NO: 2.

54. The modified cell of embodiment 53, wherein the variant Ace3 TF further comprises a deletion of at least the last seven (7) C-terminal amino acid positions 683-689 of SEQ ID NO: 2.

55. The modified cell of embodiment 35, wherein the variant Ace3 TF comprises an insertion of one or more amino acid residues at a C-terminal amino acid position selected from amino acid positions 673-683 of SEQ ID NO: 2.

56. The modified cell of any one of embodiments 32, 36 or 37, wherein the inducing substrate is selected from lactose, sophorose, gentibiose and cellulose.

57. A lignocellulosic degrading enzyme produced by the modified cell of embodiment 32.

58. A protein of interest (POI) produced by the modified cell of embodiment 34.

59. A genetically modified *Trichoderma* sp. fungal cell derived from a parental *Trichoderma* sp. cell comprising a mutated ace3 gene encoding a variant Ace3 transcription factor (TF) protein comprising at least 90% sequence identity to SEQ ID NO: 4 wherein the N-terminus of SEQ ID NO: 4 do not comprise an intact binuclear zinc ($Zn_2Cys_6$) DNA binding set forth in SEQ ID NO: 29, wherein the genetically modified cell comprises a modified ace3 gene encoding a variant Ace3 TF protein comprising at least 90% sequence identity to positions 1-672 of SEQ ID NO: 2 wherein the N-terminus of SEQ ID NO: 2 comprises an intact binuclear zinc ($Zn_2Cys_6$) DNA binding set forth in SEQ ID NO: 29 and comprises a genetic modification of one or more C-terminal amino acid residues selected from positions 673-689 of SEQ ID NO: 2.

60. The modified cell of embodiment 59, wherein the variant Ace3 TF protein upregulates the expression of a gene encoding a lignocellulosic degrading enzyme in the absence of an inducing substrate, when fermented under suitable conditions for the production of a ligno-cellulosic degrading enzyme.

61. The modified cell of embodiment 59, wherein the variant Ace3 TF protein upregulates the expression of a gene encoding a lignocellulosic degrading enzyme in the presence of an inducing substrate such that the modified cell produces an increased amount of the lignocellulosic degrading enzyme relative to the amount of the same lignocellulosic degrading enzyme produced by the parental cell in the presence of the same inducing substrate, when the modified and parental cells are fermented under the same conditions for the production of a lignocellulosic degrading enzyme.

62. The modified cell of embodiment 59, comprising an introduced expression cassette encoding a protein of interest (POI), wherein the introduced cassette comprises an upstream (5') promoter sequence derived from a gene encoding lignocellulosic degrading enzyme operably linked to a downstream (3') open reading frame (ORF) sequence encoding a POI.

63. The modified cell of embodiment 62, wherein the modified cell produces the POI in the absence of an inducing substrate when fermented under suitable conditions for the production of the POI.

64. The modified cell of embodiment 62, wherein the modified cell produces an increased amount of the POI in the presence of an inducing substrate relative to the parental cell comprising the same introduced expression cassette encoding the same POI, when the modified and parental cells are fermented under the same conditions for the production of a POI in the presence of an inducing substrate.

65. The modified cell of embodiment 59, wherein the one or more mutated C-terminal amino acid residues selected from positions 673-689 of SEQ ID NO: 2 comprises an amino acid deletion, an amino acid insertion, an amino acid substitution, or a combination thereof.

66. The modified cell of embodiment 59, wherein the one or more mutated C-terminal amino acid residues selected from positions 673-689 of SEQ ID NO: 2 comprises a deletion of at least the last seven (7) C-terminal amino acid positions 683-689 of SEQ ID NO: 2.

67. The modified cell of embodiment 59, wherein the one or more mutated C-terminal amino acid residues selected from positions 673-689 of SEQ ID NO: 2 comprises a deletion of at least the last eight (8) C-terminal amino acid positions 682-689 of SEQ ID NO: 2.

68. The modified cell of embodiment 59, wherein the one or more mutated C-terminal amino acid residues selected from positions 673-689 of SEQ ID NO: 2 comprises a deletion of at least the last nine (9) C-terminal amino acid positions 681-689 of SEQ ID NO: 2.

69. The modified cell of embodiment 59, wherein the one or more mutated C-terminal amino acid residues selected from positions 673-689 of SEQ ID NO: 2 comprises a deletion of at least the last ten (10) C-terminal amino acid positions 680-689 of SEQ ID NO: 2.

70. The modified cell of embodiment 59, wherein the one or more mutated C-terminal amino acid residues selected from positions 673-689 of SEQ ID NO: 2 comprises a deletion of at least the last eleven (11) C-terminal amino acid positions 679-689 of SEQ ID NO: 2.

71. The modified cell of embodiment 59, wherein the one or more mutated C-terminal amino acid residues selected from positions 673-689 of SEQ ID NO: 2 comprises a deletion of at least the last twelve (12) C-terminal amino acid positions 678-689 of SEQ ID NO: 2.

72. The modified cell of embodiment 59, wherein the one or more mutated C-terminal amino acid residues selected from positions 673-689 of SEQ ID NO: 2 comprises a deletion of at least the last thirteen (13) C-terminal amino acid positions 677-689 of SEQ ID NO: 2.

73. The modified cell of embodiment 59, wherein the one or more mutated C-terminal amino acid residues selected from positions 673-689 of SEQ ID NO: 2 comprises a deletion of at least the last fourteen (14) C-terminal amino acid positions 676-689 of SEQ ID NO: 2.

74. The modified cell of embodiment 59, wherein the one or more mutated C-terminal amino acid residues selected from positions 673-689 of SEQ ID NO: 2 comprises a deletion of at least the last fifteen (15) C-terminal amino acid positions 675-689 of SEQ ID NO: 2.

75. The modified cell of embodiment 59, wherein the one or more mutated C-terminal amino acid residues selected from positions 673-689 of SEQ ID NO: 2 comprises a deletion of at least the last sixteen (16) C-terminal amino acid positions 674-689 of SEQ ID NO: 2.

76. The modified cell of embodiment 59, wherein the one or more mutated C-terminal amino acid residues selected from positions 673-689 of SEQ ID NO: 2 comprises a deletion of at least the last seventeen (17) C-terminal amino acid positions 673-689 of SEQ ID NO: 2.

77. The modified cell of embodiment 59, wherein the variant Ace3 TF comprises an amino acid sequence selected from any one of SEQ ID NO: 9 through SEQ ID NO: 18.

78. The modified cell of embodiment 59, wherein the genetic modification of one or more C-terminal amino acid residues selected from positions 673-689 of SEQ ID NO: 2 is a deletion of one or more amino acid residue selected from positions 673-683 of SEQ ID NO: 2.

79. The modified cell of embodiment 59, wherein the genetic modification of one or more C-terminal amino acid residues selected from positions 673-689 of SEQ ID NO: 2 is a deletion of two consecutive amino acid residues selected from positions 673-674 of SEQ ID NO: 2, positions 674-675 of SEQ ID NO: 2, positions 675-676 of SEQ ID NO: 2, positions 676-677 of SEQ ID NO: 2, positions 677-678 of SEQ ID NO: 2, positions 678-679 of SEQ ID NO: 2, positions 679-680 of SEQ ID NO: 2, positions 680-681 of SEQ ID NO: 2, positions 681-682 of SEQ ID NO: 2, positions 682-683 of SEQ ID NO: 2 and positions 683-684 of SEQ ID NO: 2.

80. The modified cell of embodiment 59, wherein the genetic modification of one or more C-terminal amino acid residues selected from positions 673-689 of SEQ ID NO: 2 is a deletion of three consecutive amino acid residues selected from positions 673-675 of SEQ ID NO: 2, positions 674-676 of SEQ ID NO: 2, positions 675-677 of SEQ ID NO: 2, positions 676-678 of SEQ ID NO: 2, positions 677-679 of SEQ ID NO: 2, positions 678-680 of SEQ ID NO: 2, positions 679-681 of SEQ ID NO: 2, positions 680-682 of SEQ ID NO: 2, positions 681-683 of SEQ ID NO: 2, positions 682-684 of SEQ ID NO: 2 and positions 683-685 of SEQ ID NO: 2.

81. The modified cell of embodiment 59, wherein the variant Ace3 TF comprises a substitution of one or more C-terminal amino acid residues selected from amino acid positions 672-683 of SEQ ID NO: 2.

82. The modified cell of embodiment 81, wherein the variant Ace3 TF further comprises a deletion of at least the last seven (7) C-terminal amino acid positions 683-689 of SEQ ID NO: 2.

83. The modified cell of embodiment 59, wherein the variant Ace3 TF comprises an insertion of one or more amino acid residues at a C-terminal amino acid position selected from amino acid positions 673-683 of SEQ ID NO: 2.

84. The modified cell of any one of embodiments 61, 64 or 65, wherein the inducing substrate is selected from lactose, sophorose, gentibiose and cellulose.

85. A lignocellulosic degrading enzyme produced by the modified cell of embodiment 61.

86. A protein of interest (POI) produced by the modified cell of embodiment 63.

87. A method for screening for variant Ace3 TF proteins which induce the expression of a gene encoding a lignocellulosic degrading enzyme in the absence of an inducing substrate, the method comprising: (a) constructing a DNA library encoding a plurality of variant Ace3 TF proteins comprising modified amino acid residues at one or more C-terminal amino acid positions selected from positions 673-683 of SEQ ID NO: 2, (b) transforming a plurality of Trichoderma sp. cells with DNA sequences from the DNA library of step (a), and (c) cultivating and screening the plurality of transformed Trichoderma sp. cells under suitable conditions for the production a lignocellulosic degrading enzyme in the absence of an inducing substrate, wherein a screened Trichoderma sp. cell expressing a gene encoding a lignocellulosic degrading enzyme identifies a DNA library sequence therein encoding a variant Ace3 TF protein which induces the expression of a lignocellulosic degrading enzyme gene in the absence of an inducing substrate.

88. The method of embodiment 87, further comprising isolating a transformed Trichoderma sp. cell comprising a DNA library sequence encoding a variant Ace3 TF protein which induces the expression of a lignocellulosic degrading enzyme the absence of an inducing substrate.

89. The method of embodiment 88, further comprising isolating the DNA sequence encoding the variant Ace3 TF protein.

90. A method for screening for variant Ace3 TF proteins which upregulate the expression of a gene encoding a lignocellulosic degrading enzyme in the presence of an inducing substrate relative to the expression of the same gene encoding the same lignocellulosic degrading enzyme regulated by an Ace3 TF protein with wild-type C-terminus of SEQ ID NO: 2 in the presence of the same inducing substrate, the method comprising: (a) constructing a DNA library encoding a plurality of variant Ace3 TF proteins comprising modified amino acid residues at one or more C-terminal amino acid positions selected from positions 673-683 of SEQ ID NO: 2, (b) transforming a plurality of Trichoderma sp. cells with DNA sequences from the DNA library of step (a), and (c) cultivating and screening the plurality of transformed Trichoderma sp. cells under suitable conditions for the production a lignocellulosic degrading enzyme in the presence of an inducing substrate, wherein a screened Trichoderma sp. cell producing an increased amount a lignocellulosic degrading enzyme relative to the amount of the same lignocellulosic degrading enzyme produced by a Trichoderma sp. control cell comprising a gene encoding an Ace3 TF protein with wild-type C-terminus of SEQ ID NO: 2, identifies a DNA library sequence therein encoding a variant Ace3 TF protein which upregulates the expression of a lignocellulosic degrading enzyme gene in the presence of an inducing substrate.

91. The method of embodiment 90, further comprising isolating a transformed Trichoderma sp. cell comprising a DNA library sequence encoding a variant Ace3 TF protein which upregulates the expression of a lignocellulosic degrading enzyme gene in the presence of an inducing substrate.

92. The method of embodiment 91, further comprising isolating the DNA sequence encoding the variant Ace3 TF protein.

93. A method of screening for variant Ace3 TF proteins which induce the expression of a gene encoding a reporter protein in the absence of an inducing substrate, the method comprising: (a) constructing a DNA library encoding a plurality of variant Ace3 TF proteins comprising modified amino acid residues at one or more C-terminal amino acid positions selected from positions 673-683 of SEQ ID NO: 2, (b) transforming a plurality of Trichoderma sp. cells with DNA sequences from the DNA library of step (a), wherein the transformed Trichoderma sp. cells comprise an introduced expression cassette comprising an upstream (5') cellulase promoter operably linked to an open reading frame (ORF) encoding a reporter protein and (c) cultivating and screening the plurality of transformed Trichoderma sp. cells for the expression of the ORF encoding the reporter protein in the absence of an inducing substrate, wherein a screened Trichoderma sp. cell expressing the ORF encoding the reporter protein identifies a DNA library sequence therein encoding a variant Ace3 TF protein which induces the expression of the ORF encoding the reporter protein in the absence of an inducing substrate.

94. The method of embodiment 93, further comprising isolating a transformed Trichoderma sp. cell comprising a DNA library sequence encoding a variant Ace3 TF protein which induces the expression of the ORF encoding the reporter protein in the absence of an inducing substrate.

95. The method of embodiment 93, further comprising isolating the DNA sequence encoding the variant Ace3 TF protein.

96. A method for screening for variant Ace3 TF proteins which upregulate the expression of a gene encoding a reporter protein in the presence of an inducing substrate relative to the expression of the same gene encoding the same reporter protein regulated by an Ace3 TF protein with wild-type C-terminus of SEQ ID NO: 2 in the presence of the same inducing substrate, the method comprising: (a) constructing a DNA library encoding a plurality of variant Ace3 TF proteins comprising modified amino acid residues at one or more C-terminal amino acid positions selected from positions 673-683 of SEQ ID NO: 2, (b) transforming a plurality of *Trichoderma* sp. cells with DNA sequences from the DNA library of step (a), wherein the transformed *Trichoderma* sp. cells comprise an introduced expression cassette comprising an upstream (5') cellulase promoter operably linked to an open reading frame (ORF) encoding a reporter protein, and optionally comprising a downstream (3') terminator sequence operable in *Trichoderma* sp. cells and (c) cultivating and screening the plurality of transformed *Trichoderma* sp. cells for the expression of the ORF encoding the reporter protein in the presence of an inducing substrate, wherein a screened *Trichoderma* sp. cell producing an increased amount of the reporter protein relative to the amount of the same reporter protein produced by a *Trichoderma* sp. control cell comprising a gene encoding an Ace3 TF protein with wild-type C-terminus of SEQ ID NO: 2 and comprising the expression cassette of step (b), identifies a DNA library sequence therein encoding a variant Ace3 TF protein which upregulates the expression of the ORF encoding the reporter protein in the presence of an inducing substrate.

97. The method of embodiment 96, further comprising isolating a transformed *Trichoderma* sp. cell comprising a DNA library sequence encoding a variant Ace3 TF protein which upregulates the expression of the ORF encoding the reporter protein in the presence of an inducing substrate 98. The method of embodiment 97, further comprising isolating the DNA sequence encoding the variant Ace3 TF protein.

99. The method of embodiment 87 or embodiment 90, wherein the lignocellulosic degrading enzyme is selected from the group consisting of a cellobiohydrolase, an endoglucanase and a β-glucosidase.

100. The method of embodiment 93 or embodiment 96, wherein the cellulase promoter is selected from the group consisting of a cellobiohydrolase promoter sequence, an endoglucanase promoter sequence, a β-glucosidase promoter sequence and a xylanase promoter sequence.

101. The method of any one of embodiments 87, 90, 93 or 96, wherein the inducing substrate is selected from lactose, sophorose, gentibiose and cellulose.

102. A method for producing a lignocellulosic degrading enzyme in a *Trichoderma* sp. fungal cell in the absence of an inducing substrate, the method comprising: (a) isolating a mutant *T. reesei* cell comprising a mutated ace3 gene encoding a variant Ace3 transcription factor (TF) protein, wherein the variant Ace3 TF protein comprises at least 90% sequence identity to amino acid positions 1-672 of SEQ ID NO: 2 and comprises one or more mutated C-terminal amino acid residues selected from positions 673-689 of SEQ ID NO: 2, and (b) fermenting the isolated mutant cell under suitable conditions for production of a lignocellulosic degrading enzyme, wherein the suitable fermentation conditions do not include an inducing substrate.

104. The method of embodiment 103, wherein the lignocellulosic degrading enzyme is selected from the group consisting of a cellobiohydrolase, an endoglucanase and a β-glucosidase.

105. A method for producing a lignocellulosic degrading enzyme in a genetically modified *Trichoderma* sp. fungal cell in the absence of an inducing substrate, the method comprising: (a) obtaining a *Trichoderma* sp. fungal cell comprising an ace3 gene encoding a wild-type Ace3 transcription factor (TF) protein comprising at least 90% sequence identity to amino acid positions 1-689 of SEQ ID NO: 2, (b) genetically modifying the ace3 gene of the *Trichoderma* sp. cell of step (a), wherein the modified ace3 gene encodes a variant Ace3 TF protein comprising at least 90% sequence identity to amino acid positions 1-672 of SEQ ID NO: 2 and comprising one or more mutated C-terminal amino acid residues selected from positions 673-689 of SEQ ID NO: 2, and (c) fermenting the modified *Trichoderma* sp. cell of step (b) under suitable conditions for production of a lignocellulosic degrading enzyme, wherein the suitable fermentation conditions do not include an inducing substrate.

106. The method of embodiment 105, wherein the C-terminus of the wild-type Ace3 TF protein comprises at least 95% sequence identity to amino acid positions 673-689 of SEQ ID NO: 2.

107. A method for producing a lignocellulosic degrading enzyme in a genetically modified *Trichoderma* sp. fungal cell in the absence of an inducing substrate, the method comprising: (a) obtaining a *Trichoderma* sp. fungal cell comprising an ace3 gene encoding a variant Ace3 TF protein comprising at least 90% sequence identity to the Ace3-S TF protein of SEQ ID NO: 4, (b) genetically modifying the ace3 gene of the *Trichoderma* sp. cell of step (a), wherein the modified ace3 gene encodes a variant Ace3 TF protein comprising at least 90% sequence identity to amino acid positions 1-672 of SEQ ID NO: 2 and comprising one or more mutated C-terminal amino acid residues selected from positions 673-689 of SEQ ID NO: 2, and (c) fermenting the modified *Trichoderma* sp. cell of step (b) under suitable conditions for production of a lignocellulosic degrading enzyme, wherein the suitable fermentation conditions do not include an inducing substrate.

108. The method of embodiment 107, wherein the variant Ace3 TF protein comprising at least 90% sequence identity to the Ace3-S TF protein of SEQ ID NO: 4 does not comprise an intact binuclear zinc ($Zn_2Cys_6$) DNA binding set forth in SEQ ID NO: 29.

109. The method of embodiment 107, wherein the genetically modified ace3 gene encoding a variant Ace3 TF protein comprising at least 90% sequence identity to amino acid positions 1-672 of SEQ ID NO: 2 comprises an intact binuclear zinc ($Zn_2Cys_6$) DNA binding set forth in SEQ ID NO: 29.

110. A method for producing a protein of interest (POI) in a modified *Trichoderma* sp. cell in the absence of an inducing substrate, the method comprising: (a) obtaining a *Trichoderma* sp. fungal cell comprising an ace3 gene encoding a wild-type Ace3 transcription factor (TF) protein comprising at least 90% sequence identity to amino acid positions 1-689 of SEQ ID NO: 2, (b) genetically modifying the ace3 gene of the *Trichoderma* sp. cell of step (a), wherein the modified ace3 gene encodes a variant Ace3 TF protein comprising at least 90% sequence identity to amino acid positions 1-672 of SEQ ID NO: 2 and comprising one or more mutated C-terminal amino acid residues selected from positions 673-689 of SEQ ID NO: 2, (c) introducing an expression cassette encoding a POI into the modified *Trichoderma* sp. cell of step (b), wherein the expression cassette comprises an upstream (5') promoter sequence derived from a gene encoding lignocellulosic degrading enzyme operably linked to a downstream (3') open reading frame (ORF) sequence encoding a POI, and (d) fermenting the modified *Trichoderma* sp. cell of step (c) under suitable conditions for production of the POI, wherein the suitable fermentation conditions do not include an inducing substrate.

111. The method of embodiment 110, wherein steps (b) and (c) are performed simultaneously or in either order.

112. A method for producing a protein of interest (POI) in a modified *Trichoderma* sp. cell in the absence of an inducing substrate, the method comprising: (a) obtaining a *Trichoderma* sp. fungal cell comprising an ace3 gene encoding a variant Ace3 TF protein comprising at least 90% sequence identity to the Ace3-S TF protein of SEQ ID NO: 4, (b) genetically modifying the ace3 gene of the *Trichoderma* sp. cell of step (a), wherein the modified ace3 gene encodes a variant Ace3 TF protein comprising at least 90% sequence identity to amino acid positions 1-672 of SEQ ID NO: 2 and comprising one or more mutated C-terminal amino acid residues selected from positions 673-689 of SEQ ID NO: 2, (c) introducing an expression cassette encoding a POI into the modified *Trichoderma* sp. cell of step (b), wherein the expression cassette comprises an upstream (5') promoter sequence derived from a gene encoding lignocellulosic degrading enzyme operably linked to a downstream (3') open reading frame (ORF) sequence encoding a POI, and (d) fermenting the modified *Trichoderma* sp. cell of step (c) under suitable conditions for production of the POI, wherein the suitable fermentation conditions do not include an inducing substrate.

113. The method of embodiment 110, wherein steps (b) and (c) are performed simultaneously or in either order.

EXAMPLES

It should be understood that the following Examples, while indicating embodiments of the disclosure, are given by way of illustration only. From the above discussion and these Examples, one of skill in the art can make various changes and modifications of the disclosure to adapt it to various usages and conditions. Such modifications are also intended to fall within the scope of the claimed invention.

Example 1

Ace3-L Protein Comprising C-Terminal Truncations

A. Overview

Ace3 is a *T. reesei* transcriptional factor which regulates cellulase and hemi-cellulase production under inducing conditions (e.g., in the presence of lactose). Likewise, a highly functional form of the Ace3 transcription factor named "Ace3L" has been identified and described in PCT Publication No. WO2018/067599. For example, as described in the WO2018/067599 publication, a *T. reesei* strain expressing the Ace3L transcription factor (e.g., SEQ ID NO: 6), not only showed enhanced (increased) protein production in the presence of an inducer (e.g., lactose, sophorose), but also showed significantly increased protein production in the absence of an inducer.

The Ace3 transcription factor has two (2) known variants at its C-terminus. For example, the ace3 gene in *T. reesei* strain QM6a encodes an Ace3-S protein (FIG. 1) comprising a full length (wild-type) C-terminus encoded by the ace3 gene, while the same ace3 gene in *T. reesei* strains of RL-P37 and RUT-C30 contains a premature stop codon resulting in an eleven (11) amino acid truncation of the encoded protein (FIG. 1; SEQ ID NO: 6). Additionally, as shown in FIG. 1, the Ace3L protein comprises an intact binuclear zinc cluster ($Zn_2Cys_6$) DNA binding domain at the N-terminus (FIG. 3; SEQ ID NO: 6) relative to the Ace3-S protein SEQ ID NO: 4). An Ace3-LC variant was generated by reverting the premature stop codon to a glutamine codon; it hence comprises an intact binuclear zinc cluster ($Zn_2Cys_6$) DNA binding domain at the N-terminus and a full-length (wild-type) sequence at the C-terminus.

As described and exemplified herein, the truncated C-terminus of the Ace3 protein and the intact N-terminal binuclear zinc cluster ($Zn_2Cys_6$) DNA binding domain of the Ace3 protein are both essential features for its function in increasing protein production both in the absence and presence of an inducer. In the present example, Applicant further evaluated the C-terminal amino acid region of the Ace3 protein by selectively truncating the C-terminal amino acid resides as described below. The *T. reesei* parental cells used in the following examples were derived from *T. reesei* strain RL-P37 (NRRL Deposit No. 15709), wherein the *T. reesei* pyr4 gene has been deleted, as generally described by Sheir-Neiss and Montenecourt, 1984.

B. Expression Vectors and Strain Construction

Two (2) sets of expression vectors with Ace3 C-terminal truncations were constructed. The first set of six (6) vectors contain C-terminal truncations ranging from zero (0) to twenty-five (25) amino acids at a five (5) amino acid increment (see, TABLE 1; set 1). The second set of twelve (12) vectors contain truncations ranging from six (6) to nineteen (19) amino acids at a one (1) amino acid increment (see, TABLE 1; set 2).

These eighteen (18) Ace3-LC_C-term variant expression vectors were constructed using standard molecular biological procedures. These vectors were designed to enable targeted integration of ace3 expression cassette at the glucoamylase (gla1) locus in *T. reesei*. They harbor the 5' and 3' flanks of the *T. reesei* gla1 locus needed for targeted integration. The 5' flank sequence comprises a 1.5 Kb homology box homologous to the DNA sequence corresponding to scaffold_1:1489226-1490662. The 3' flank DNA sequence comprises a 1.5 Kb homology box homologous to the DNA sequence corresponding to scaffold_1: 1492835-1494335. These sequences were designed to target the gla1 gene (JGI protein ID Trire2_1885) and replace the region of the genome between the 5' and 3' Flanks (scaffold_1: 1490663-1492834) with the intervening cassette sequences. The expression vectors also comprise a heterologous *T. reesei* dic1 promoter sequence (scaffold_8: 1376871-1378833, e.g. see PCT Publication No. WO2018/ 067599) operably linked to the ace3 ORF coding sequences with the native ace3 gene terminator. In addition, the vectors contain a pyr4 marker with its native promoter and terminator for selection of *T. reesei* transformants. A repeat of the pyr4 promoter was included to enable excision of the pyr4 gene after integration at the gla1 locus. The vectors also contain with the bacterial ColE1 on and AmpR gene for replication and selection in *E. coli*, the yeast 2μ on and ura3 genes for replication and selection in *S. cerevisiae*. A representative vector map is shown in FIG. 2, depicting vector pYL72 containing the ORF encoding the Ace3-LC protein (SEQ ID NO: 2; i.e., comprising the full-length, wild-type C-terminus). The other vectors (e.g., pYL73, pYL74, etc.) comprise ORF sequences encoding various C-terminally truncated Ace3 proteins (TABLE 1).

The expression vectors presented in TABLE 1 were digested with PmeI to release the fragments for targeted integration and separated with agarose gel electrophoresis. Correct fragments were isolated from the gel using a gel extraction kit (Qiagen) according to the manufacturer's protocol. Cas9 nuclease and a synthetic single guide RNA (sgRNA) (SEQ ID NO: 70) that is targeted at a 23 bp sequence within the gla1 gene, were assembled in vitro according the manufacturer's protocol (Synthego), as generally set forth in PCT Publication No. WO/2016/100568. Approximately ten (10) μg of purified fragment and the assembled Cas9-sgRNA complex were used to transform protoplasts of a pyr4⁻ mutant of *T. reesei* (RL-P37) strain. The transformation was performed using the polyethylene glycol (PEG) mediated protoplast transformation protocol (Ouedraogo et al., 2015; Penttila et al., 1987).

The transformants were grown on Vogel's minimal medium agar plates to select for uridine prototrophy acquired by the pyr4 marker. Growing clones were screened for correct integration by PCR using primers listed in TABLE 2. Clones giving expected signals were purified to single cell clones and re-screened for correct integration and clone purity by PCR using primers listed in TABLE 2. The PCR products were sequenced by Sanger sequencing to verify the presence of designated ace3 C-terminal truncation variants. The purified and sequence verified Ace3 C-terminal truncation variants are listed in TABLE 3.

TABLE 1

ACE3-LC EXPRESSION VECTORS WITH C-TERMINAL TRUNCATIONS

| | Ace3 variants | C-terminal truncation* | SEQ ID NO |
|---|---|---|---|
| Vector # (Set1) | | | |
| pYL72 | ace3LC-Cterm-WT | QM6a, No C-term truncation | 2 |
| pYL73 | ace3LC -Cterm-5AA | 5 AA | 7 |
| pYL74 | ace3LC -Cterm-10AA | 10 AA | 12 |
| pYL75 | ace3LC -Cterm-15AA | 15 AA | 16 |
| pYL76 | ace3LC -Cterm-20AA | 20 AA | 21 |
| pYL77 | ace3LC -Cterm-25AA | 25 AA | 22 |
| Vector # (Set 2) | | | |
| pYL84 | ace3LC -Cterm-6AA | 6 AA | 8 |
| pYL85 | ace3LC-Cterm-7AA | 7 AA | 9 |
| pYL86 | ace3LC-Cterm-8AA | 8 AA | 10 |
| pYL87 | ace3LC-Cterm-9AA | 9 AA | 11 |
| pYL88 | ace3LC-Cterm-11AA | 11 AA | 6 |
| pYL89 | ace 3 LC-Cterm-12AA | 12 AA | 13 |
| pYL90 | ace 3 LC-Cterm-13AA | 13 AA | 14 |
| pYL91 | ace 3 LC-Cterm-14AA | 14 AA | 15 |
| pYL92 | ace 3 LC-Cterm-16AA | 16 AA | 17 |
| pYL93 | ace 3 LC-Cterm-17AA | 17 AA | 18 |
| pYL94 | ace 3 LC-Cterm-18AA | 18 AA | 19 |
| pYL95 | ace 3 LC-Cterm-19AA | 19 AA | 20 |

*AA is abbreviation for Amino Acids

TABLE 2

PCR PRIMERS FOR SCREENING CORRECT TRANSFORMANTS

| Primer | | Sequence | SEQ ID NO |
|---|---|---|---|
| *To check the presence of Ace 3LC-C-term variant expression cassette* | | | |
| (TP218) | ace3-int-for-8 | CGCATGGTAATTACGCAGA | 23 |
| (TP220) | pyr4-rev-1 | GTCCATGAGCTTGAACAGGT | 24 |
| *To check the integration junction at gla 5'* | | | |
| (TP125) | gla-up-for | AGCAGATCCCGTTACCGATTCA | 25 |
| (TP123) | Pdic1-int-rev | GTCGAGTCCACGTCGTCTCT | 26 |
| *To check the integration junction at gla 3'* | | | |
| (TP221) | Tpyr4-for | TGTTATGACGTACCAGTTGGGATGA | 27 |
| (TP222) | gla-dn-rev | CCGCTCAGGCATACGAGCGA | 28 |

TABLE 3

*T. REESEI* STRAINS

| Strain # | Strain genotype |
|---|---|
| LT338 | RL-P37, Parental strain |
| LT378 | RL-P37 gla1::ace3LC-CtermWT |
| LT380 | RL-P37 gla1::ace3LC-Cterm-5AA |
| LT382 | RL-P37 gla1::ace3LC-Cterm-10AA |
| LT384 | RL-P37 gla1::ace3LC-Cterm-15AA |
| LT386 | RL-P37 gla1::ace3LC-Cterm-20AA |
| LT388 | RL-P37 gla1::ace3LC-Cterm-25AA |
| LT416 | RL-P37 gla1::ace3LC-Cterm-6AA |
| LT418 | RL-P37 gla1::ace3LC-Cterm-7AA |
| LT420 | RL-P37 gla1::ace3LC-Cterm-8AA |
| LT422 | RL-P37 gla1::ace3LC-Cterm-9AA |
| LT424 | RL-P37 gla1::ace3LC-Cterm-11AA |
| LT426 | RL-P37 gla1::ace3LC-Cterm-12AA |
| LT428 | RL-P37 gla1::ace3LC-Cterm-13AA |
| LT430 | RL-P37 gla1::ace3LC-Cterm-14AA |
| LT432 | RL-P37 gla1::ace3LC-Cterm-16AA |
| LT434 | RL-P37 gla1::ace3LC-Cterm-17AA |
| LT436 | RL-P37 gla1::ace3LC-Cterm-18AA |
| LT438 | RL-P37 gla1::ace3LC-Cterm-19AA |

C. Cultivation of the Different ace3 Transformants

The parental (LT338) and transformed (daughter) *T. reesei* cells (TABLE 3) described above were tested under both "non-inducing" (glucose) and "inducing" (glucose/sophorose or lactose) conditions. For example, in the "non-inducing" condition, cells were grown in 1.25 ml liquid broth of defined medium, supplemented with 2% glucose (weight/volume) in a regular twenty-four (24) well microtiter plate (MTP). In the "inducing" condition, cells were grown in 1.25 ml liquid broth of defined medium supplemented with 2% lactose or 2% glucose/sophorose (weight/volume) in a twenty-four (24) well MTP, wherein lactose or sophorose serves as a potent inducer for cellulase enzyme expression.

The MTP cultures were incubated at 28° C., 250 rpm, 85% humidity for five (5) days. Following incubation, the supernatants from all cultures were harvested and the total secreted protein was measured by the Bradford dye-binding assay at 595 nm using the Bio-Rad reagent (Thermo Scientific®; Catalogue No.: 23236), and five (5) dilutions of bovine serum albumin (BSA) as a standard according to manufacturer's protocol.

D. Ace3-LC Variants with a Ten to Fifteen Amino Acid C-Terminal Truncation Are Functional As shown in FIG. 7, Applicant evaluated total protein production with the first set of strains expressing Ace3-LC variants (TABLE 1; set 1 and TABLE 3) with five (5), ten (10), fifteen (15), twenty (20) and twenty-five (25) amino acid truncations at C-terminus (e.g., see TABLE 1; set 1; TABLE 3 and FIG. 7). As indicated in FIG. 7, the parental control strain RL-P37 can only produce high amount of protein on lactose (i.e., under inducing conditions) and produced a minimal basal level of protein on glucose (i.e., under non-inducing condition). Daughter cells expressing Ace3-L with a ten (10) amino acid truncation (SEQ ID NO: 12), or a fifteen (15) amino acid truncation (SEQ ID NO: 16), demonstrated an increase in protein production under both lactose (inducing) and glucose (non-inducing) conditions. Thus, as presented in FIG. 7, the fold change increase is approximately 1.8× on glucose, and 3× on lactose relative to the protein level produced by the parental strain (RL-P37) on lactose.

For example, this improvement in total protein production is similar to the improvement in protein production observed for the Ace3-L protein comprising the eleven (11) amino acid truncation (SEQ ID NO: 6) described in PCT Publication No. WO2018/067599. The truncation of five (5) amino acids (SEQ ID NO: 7) showed a similar protein expression level as the parental strain on both lactose and glucose. Truncation of zero (0) amino acids (i.e., Ace3-LC; WT C-terminus; SEQ ID NO: 2), twenty (20) amino acids (SEQ ID NO: 21), or twenty-five (25) amino acids (SEQ ID NO: 22) significantly reduced total protein production both on lactose and glucose. These results demonstrate that truncation of the Ace3 protein's C-terminus is essential for its function in up-regulating protein production. Likewise, as indicated in FIG. 7, there is an upper and lower limit to the number of amino acid truncations permitted at the Ace3 C-terminus.

E. Ace3-LC Variants with a Seven to Seventeen Amino Acid C-Terminal Truncation Are Functional To further explore the upper and lower limits of Ace3 C-terminal amino acid truncations permissible, Applicant constructed and tested *T. reesei* strains comprising Ace3-LC with C-terminal truncations between five (5) and twenty (20) amino acids (i.e., using one (1) amino acid increments of truncation; e.g., see TABLE 1, TABLE 3 and FIG. 8). For example, truncation of five (5) or six (6) amino acids (FIG. 8) showed similar result as the parental strain (i.e., basal protein production on glucose, and high production on lactose). In contrast, truncation of at least seven (7) to seventeen (17) amino acids showed improved production on both glucose and lactose, which is similar to previous observation with an eleven (11) amino acid truncation in Ace3-L protein (FIG. 8). Furthermore, truncation of eighteen (18) or more C-terminal amino acids significantly reduced protein production to the basal level both on lactose and glucose (FIG. 8).

Thus, as described above, the (Ace3) C-terminus plays an essential role in the function of the Ace3 protein (i.e., regulation of protein production), both in the presence of an inducer and in the absence of inducer. For example, strains expressing an Ace3-LC protein with truncations of seven (7) to seventeen (17) amino acids showed an approximately 2-fold improvement in total protein production under glucose (non-inducing) conditions compared to the parental strain RL-P37 under lactose (inducing) conditions, and they also showed an approximately 3-fold improvement in total protein production under lactose (inducing) conditions compared to the parental strain RL-P37 under lactose (inducing) conditions. In contrast, strains expressing an Ace3-LC with either the wild-type C-terminus, or a C-terminus with truncations of five (5), six (6), eighteen (18) or more amino acid produced a minimal amount of protein under glucose (non-inducing) conditions, and they either produced similar or reduced amount of protein under lactose (inducing) conditions compared to the parental strain under lactose (inducing) conditions. Thus, as demonstrated herein, *T. reesei* strains comprising an Ace3-LC protein having at least a seven (7) amino acid truncation (SEQ ID NO: 9) and up to a seventeen (17) amino acid truncation (SEQ ID NO: 18) comprise an enhanced protein production phenotype (relative to the other strains tested), which enhanced protein production phenotype was observed both in the presence of an inducer and in the absence of inducer.

Example 2

Reversion of Ace3 Truncation

A. Overview

The industrially important *Trichoderma* strains Rut-C30 and RL-P37 are mutagenized derivatives of *Trichoderma* natural isolate QM6a (Le Crom et al., 2009; Sheir-Neiss and Montenecourt, 1984), with strain NG14 being the last common ancestor. A genomic comparison of NG14 to QM6a identified one hundred twenty-six (126) single nucleotide polymorphisms (SNPs) and twenty-two (22) insertions and deletions (indels) between the original strain QM6a (PMID: 19805272).

Among these was a point-mutation in a gene encoding a transcription factor which was predicted to result in an eleven (11) amino acid C-terminal truncation based on the computationally predicted gene structure available at the time. Later, this transcription factor would be named Ace3 after a knock-out of the gene resulted in significant loss of cellulase and hemi-cellulase production under inducing conditions (e.g., in the presence of lactose; Hakkinen et al., 2014). Previously Applicant has shown that the eleven (11) amino acid truncation is essential for the Ace3-L (a specific variant of Ace3) function in improving protein production both in the presence and absence of an inducer when it is overexpressed (e.g., see PCT Publication No. WO2018/067599).

As set forth above in Example 1, Applicant has determined the precise number of C-terminal (amino acid) truncations (i.e., 7~17 amino acids) required for improving protein production. In the present example, Applicant has molecularly reverted the C-terminal truncation point mutation at the ace3 locus back to the "wild type" (C-terminal) sequence of QM6a, which encodes the full-length Ace3 protein comprising a wild-type N-terminus (FIG. 1A; SEQ ID NO: 2) and a wild-type C-terminus (FIG. 1B; SEQ ID NO: 2) ending in glycine (G). As described below, strains expressing the full-length Ace3 transcription factor (SEQ ID NO: 2) showed decreased protein production.

B. *T. reesei* Host Strain

The *T. reesei* parental strain described in the instant example was derived from *T. reesei* strain RL-P37 (NRRL Deposit No. 15709), as described by Sheir-Neiss and Montenecourt (1984). A strain, herein named "T4abc pyr2", is a mutagenized derivative of RL-P37, with notable mutations in the pyr2 gene such that the strain requires uridine for growth and a nik1 (M743T) mutation that increases total protein production (e.g., see, U.S. Patent Publication No. 2018/0037919).

C. Expression Vector and Strain Construction

The *Trichoderma* ace3 reversion cassette plasmid, pRATT346, was prepared using standard molecular biology procedures, such that one skilled in the art may readily recreate this plasmid from the relevant DNA parts disclosed. The pRATT34 plasmid included a DNA sequence having a 2.0 Kb homology box homologous to the DNA sequence corresponding to Scaffold 8, 422475 to 424516 (Left Flank). The nucleotide corresponding to Scaffold 8, 424132 within this Left Flank was a cytosine (C) as in the genome of QM6a, as opposed to a thymine (T) as in the genome of NG14 and derivatives including T4abc. Also included within the plasmid was a DNA sequence having a 1.8 Kb homology box homologous to the DNA sequence corresponding to Scaffold 8, 424588 to 426381 (Right Flank). These sequences were designed to target the ace3 gene and replace the regions of the genome between the Left and Right Flanks (Scaffold 8, 424517 to 424587) with the intervening cassette sequences.

These intervening cassette sequences included a pyr2 selection marker from *Trichoderma* atroviride intended to minimize homology to the endogenous *T. reesei* pyr2 in the genome of the strain to be transformed. Immediately upstream of the pyr2 selection marker was a directly repeated duplication of the 3'-end of the marker (Repeat), which facilitates the subsequent loss of the marker and isolation of useful pyr2 mutant derivatives of the transformants/disruptants. In a subset of transformants with the correctly targeted intervening cassette sequence, the cytosine (C) nucleotide in the Left Flank would also be incorporated into the genome replacing the mutant thymine (T) nucleotide (Scaffold 8, 424132). The ace3 reversion allele (encoding full-length Ace3; SEQ ID NO: 2) described herein contains both the nucleotide reversion at Scaffold 8, 424132 and the insertion of the repeat-flanked pyr2 marker between Scaffold 8, 424517 to 424587.

Thus, strain T4abc pyr2 was transformed with the ace3 reversion cassette from pRATT346 using PEG-mediated transformation and plated with Vogel's minimal medium (Vogel, 1956) containing 1.2 M sorbitol to select for candidates based on uridine prototrophy acquired by the pyr2 marker. *Trichoderma* transformations are well known and described in the art (e.g., see U.S. Pat. No. 5,246,853). Individual transformants were isolated and propagated by transfer to Vogel's minimal medium. PCR analysis was used to identify transformants in which the ace3 reversion cassette integrated at the ace3 locus by homologous recombination, using methods known to one skilled in the art per guidance below.

Only a subset of recombinant cells may successfully utilize the homologous flanks to correctly target the disruption of the gene of interest, so many transformants may need to be screened to identify one with the desired event. PCR can be used to test which recombinant cells have the desired targeted disruption. Primers must be designed that amplify across each of the homology box regions, where one primer primes at a location within the selectable marker greater than 100 bp from the closest end and the other primes at a location greater than 100 bp beyond the end of a homology box region within the adjacent genomic sequence. Cells likely containing the correct targeted disruption will successfully create PCR products spanning the Left Flank and Right Flank of the disruption cassette, whereas unsuccessful transformation events will not generate a product of the expected size. At this stage the culture may be a mix of transformed and untransformed cells, so a step of purification may be needed. Purification of the culture can be tested by PCR for loss of a short PCR product spanning the disruption site.

Following spore purification, further PCR analysis was done to ensure integration occurred correctly and that the transformants were homokaryotic. Then a portion of the ace3 gene spanning the reversion mutation was PCR amplified and sequenced to determine whether this mutation in the Left Flank was incorporated during the integration event. The generated strain with confirmed homologous integration of the ace3 reversion cassette was named "T4abc ace3_rev".

D. Fermentation of the ace3 Reversion Transformant

Three (3) strains were evaluated in shake flask fermentations for their protein production, which included strains "T4abc" (containing the ace3 truncation allele), "T4abc ace3_rev" (containing the ace3 full-length allele), and "T4abc del-cbh1" (containing a deletion of the cbh1 cellobiohydrolase gene). Each strain was evaluated in two (2) independent shake flasks (e.g., Flask A and Flask B).

Liquid defined (LD) culture medium (e.g., see, U.S. Pat. No. 8,455,631), contained the following components: Casamino acids, 9 g/L; (NH$_4$)$_2$SO$_4$, 5 g/L; MgSO$_4$·7H$_2$O, 1 g/L; KH$_2$PO$_4$, 4.5 g/L; CaCl$_2$·2H$_2$O, 1 g/L, PIPPS, 33 g/L, 400× *T. reesei* trace elements, 2.5 ml/L; pH adjusted to 5.5 with NaOH. After sterilization, lactose or a glucose/sophorose mixture was added to a final concentration of 1.6% w/v.

To create a seed culture, the spores of each strain were added separately to 50 mL of YEG (5 g/L yeast extract, 22 g/L glucose, H$_2$O) in a 250 mL flask. The cultures were grown for thirty-six to forty-eight (36-4)8 hours at 28° C. and 200 rpm in a shaking incubator. After incubation, 0.3 mL of seed culture were added to 50 mL of LD medium in a baffled shake flask. This production culture was grown for five (5) days at 28° C. and 180 rpm. Secreted protein was harvested by centrifugation to pellet cells, and then collecting the supernatant. Proteins were precipitated from the supernatant with an equal volume of trichloroacetic acid (TCA), followed by dissolution in 0.1 N sodium hydroxide (NaOH). Total protein was then measured with a BCA protein assay (ThermoFisher Scientific, Grand Island, N.Y., USA) per manufacturer protocol. BCA assay numbers were normalized to the average of T4abc cultures, which were run in parallel to minimize the influence of any week-to-week variation in total protein production efficiency.

As shown in FIG. 9, the total secreted protein titer decreased 73% when the ace3 mutation was reverted in the T4abc background, such that it encoded the full-length Ace3 (e.g., SEQ ID NO: 2), relative to the T4abc parental strain which encoded the truncated version of Ace3 C-terminus (e.g., SEQ ID NO: 6). By comparison, deletion of the gene encoding the most prominent secreted protein (Cbh1) reduced the total secreted protein titer by only 47%.

Example 3

Ace3 C-Terminal Amino Acid Variants

As generally described above in Examples 1 and 2, Applicant has demonstrated that a defined number of amino acid truncations (e.g., 7-17) at Ace3LC C-terminus are required for improving protein productivity. In addition, as briefly set forth above in the Detailed Description, Applicant contemplates that other genetic modifications of the Ace3 C-terminus (e.g., substitutions, insertions, internal (C-terminal) deletions, combinations thereof, etc.) are equally suitable genetic modifications for improving protein productivity.

The instant example describes compositions and methods for constructing Ace3 C-terminal variant libraries and screening such libraries for improved protein productivity. For example, C-terminal variant libraries for Ace3 can be generated by one skilled in the art by replacement of the coding sequence for Ace3-LC coding for amino acids 641 through 689 of SEQ ID NO: 2 from plasmid pYL72 (FIG. 6) and by reference to the sequence identification number (SEQ ID NO) provided for each library and the exemplary plasmid pA3L02 (FIG. 11) for SEQ ID NO: 32. Thus, Applicant describes herein methods for constructing and screening three (3) different Ace3 C-terminal libraries including, a site substitution library (Library 1), a scanning insertion library (Library 2) and scanning deletion library (Library 3). Thus, the three library examples described herein are not meant to be limiting, but rather exemplify the overall approach, and may be readily adapted by the skilled artisan to design/construct other Ace3 C-terminal variant libraries and screen the same for improve protein productivity.

Library 1 is a site substitution library, wherein the codon for each amino acid corresponding to amino acid positions 673 through 683 of SEQ ID NO: 2 are substituted (mut) with a "NNK" codon, wherein "N" is any nucleotide and "K" is "G" or "T" nucleotide. The Library 1 degenerate DNA sequences for each coded amino acid position corresponding to amino acids 641 through 689 of SEQ ID NO: 2, are set forth as SEQ ID NO: 32-42, respectively and presented below in TABLE 4. For comparison, SEQ ID NO: 31 corresponds to the native DNA sequence for each coded amino acid position corresponding to amino acids 641 through 689 of SEQ ID NO: 2 (e.g., see SEQ ID NO: 30, comprising amino acids positions 641 to 689 of SEQ ID NO:2).

TABLE 4

LIBRARY 1: ACE3-LC EXPRESSION VECTORS WITH C-TERMINAL SUBSTITUTIONS

| Vector # | Ace3 Variant | Mutant AA position* | SEQ ID NO** |
|---|---|---|---|
| pYL72 | ace3-LC C-term WT | none | 31 |
| pA3L02 | ace3-LC mut 673m | 673 | 32 |
| pA3L03 | ace3-LC mut 674m | 674 | 33 |
| pA3L04 | ace3-LC mut 675m | 675 | 34 |
| pA3L05 | ace3-LC mut 676m | 676 | 35 |
| pA3L06 | ace3-LC mut 677m | 677 | 36 |
| pA3L07 | ace3-LC mut 678m | 678 | 37 |
| pA3L08 | ace3-LC mut 679m | 679 | 38 |
| pA3L09 | ace3-LC mut 680m | 680 | 39 |
| pA3L10 | ace3-LC mut 681m | 681 | 40 |
| pA3L11 | ace3-LC mut 682m | 682 | 41 |
| pA3L12 | ace3-LC mut 683m | 683 | 42 |

*AA is abbreviation for Amino Acid
**SEQ ID NO corresponds to the variant nucleic acid sequence replacing the nucleotide sequence encoding Ace3-LC amino acids 641 to 689 in plasmid pYL72.

Library 2 is a scanning insertion library, wherein the three (3) codon sequence "NDT" (codon 1)—"NDT" (codon 2)—"NNK" (codon 3) is inserted after (3') each codon corresponding to amino acids 672 through 683 of SEQ ID NO: 2, wherein "N" is any nucleotide, "D" is an "A", "G" or "T" nucleotide, and "K" is a "G" or "T" nucleotide. The Library 2 degenerate DNA sequences for each coded amino acid position corresponding to amino acids 641 through 689 of SEQ ID NO: 2 are set forth as SEQ ID NO: 43-54, respectively and presented below in TABLE 5.

TABLE 5

LIBRARY 2: ACE3-LC EXPRESSION VECTORS WITH C-TERMINAL INSERTIONS

| Vector # | Ace3 variants | AA position proceeding insertion* | SEQ ID NO** |
|---|---|---|---|
| pYL72 | ace3-LC C-term WT | none | 31 |
| pA3L13 | ace3-LC ins__672i | 672 | 43 |
| pA3L14 | ace3-LC ins__673i | 673 | 44 |
| pA3L15 | ace3-LC ins__674i | 674 | 45 |
| pA3L16 | ace3-LC ins__675i | 675 | 46 |
| pA3L17 | ace3-LC ins__676i | 676 | 47 |
| pA3L18 | ace3-LC ins__677i | 677 | 48 |
| pA3L19 | ace3-LC ins__678i | 678 | 49 |
| pA3L20 | ace3-LC ins__679i | 679 | 50 |
| pA3L21 | ace3-LC ins__680i | 680 | 51 |
| pA3L22 | ace3-LC ins__681i | 681 | 52 |
| pA3L23 | ace3-LC ins__682i | 682 | 53 |
| pA3L24 | ace3-LC ins__683i | 683 | 54 |

*AA is abbreviation for Amino Acids
**SEQ ID NO corresponds to the variant nucleic acid sequence replacing the nucleotide sequence encoding Ace3-LC amino acids 641 to 689 in plasmid pYL72.

Library 3 is a scanning deletion library, wherein each codon corresponding to an amino acid position 673 through 683 of SEQ ID NO: 2 is modified as follows: starting at the codon corresponding to amino acid position 673 of SEQ ID NO: 2, the position 673 codon and the next two adjacent and downstream (3') codons (i.e., nine (9) nucleotides in total) are deleted from the Ace3 coding sequence. The Library 3 DNA sequences for each coded amino acid position corresponding to amino acids 641 through 689 of SEQ ID NO: 2 are disclosed as SEQ ID NO: 55-65 and presented below in TABLE 6.

TABLE 6

LIBRARY 3: ACE3-LC EXPRESSION VECTORS WITH C-TERMINAL INTERNAL DELETIONS

| Vector # | Ace3 variants | Deleted AA positions* | SEQ ID NO** |
|---|---|---|---|
| pYL72 | ace3-LC C-term WT | none | 31 |
| pA3L26 | ace3-LC del__673d | 673-674-675 | 55 |
| pA3L27 | ace3-LC del__674d | 674-675-676 | 56 |
| pA3L28 | ace3-LC del__675d | 675-676-677 | 57 |
| pA3L29 | ace3-LC del__676d | 676-677-678 | 58 |
| pA3L30 | ace3-LC del__677d | 677-678-679 | 59 |
| pA3L31 | ace3-LC del__678d | 678-679-680 | 60 |
| pA3L32 | ace3-LC del__679d | 679-680-681 | 61 |
| pA3L33 | ace3-LC del__680d | 680-681-682 | 62 |
| pA3L34 | ace3-LC del__681d | 681-682-683 | 63 |
| pA3L35 | ace3-LC del__682d | 682-683-684 | 64 |
| pA3L36 | ace3-LC del__683d | 683-684-685 | 65 |

*AA is abbreviation for Amino Acids
**SEQ ID NO corresponds to the variant nucleic acid sequence replacing the nucleotide sequence encoding Ace3-LC amino acids 641 to 689 in plasmid pYL72.

By pooling the degenerate library plasmid clones comprising the mutated amino acid position (e.g., from Library 1), one skilled in the art can reduce the number of *Trichoderma reesei* transformations needed. For example, the entirety of Library 3 could reasonably be pooled for *Trichoderma reesei* transformation. Thus, pooling can be done after isolation and sequencing of individual plasmid clones, or by pooling random *E. coli* transformants prior to plasmid extraction, when there is high confidence in correct modification of the pYL72 plasmid in >90% of *E. coli* transformants, and there are >100 *E. coli* transformants for the pool.

Thus, *Trichoderma reesei* cells (e.g., RL-P37) are transformed as described above in Example 1, but with pooled construct libraries described above to target Ace3 variants to the gla1 locus. For each transformed library, >60 transformants are cultivated and assayed for protein production as described in Example 1. The cell cultures can be preserved to enable molecular characterization of transformants of interest. Transformants with integrations of plasmids pYL72 (Ace3-LC) and pYL88 (Ace3-LC C-term-11) are included in at least triplicate per twenty-four (24) well plate, as negative and positive controls. For example, from the "NNK" degeneracy in Library 1, it would be expected that 1/32 clones will have a stop codon, thereby encoding one of the truncated Ace3 variants described in Example 1, wherein these clones (truncated Ace3 variants) serve as internal positive controls and validation of methods implemented.

Likewise, some *Trichoderma* transformants carrying Ace3 variants (e.g., such as the pYL88 (Ace3-LC C-term-11) transformants) will be able to produce elevated amounts of secreted cellulases and hemicellulases during fermentation, relative to pYL72 (Ace3-LC) transformants in the absence of an inducer. To determine the sequence of the Ace3 variants integrated at gla1 locus in these transformants, the variants can be molecularly characterized by methods known in the art as follows.

Genomic DNA is extracted from the individual transformants and the C-terminal portion of the Ace3 variant at the gla1 locus is PCR amplified from each transformant individually, using a forward primer (SEQ ID NO: 23, TABLE 2) that primes approximal 500 bp upstream (5') to the codon encoding amino acid position 670 of SEQ ID NO: 2, and a reverse primer (SEQ ID 24, TABLE 2) that primes specifically in the pyr4 gene and approximal 900 bp downstream (3') of the stop codon of Ace3 variants. The purified PCR products are then sequenced with additional primers nested or by other sequencing methods known to one of skill in the art. Subsequently, via analysis of the sequencing results, the Ace3 variants demonstrating enhanced protein production in the absence of inducer are readily determined.

As appreciated by one of skill in the art, some false positives may be obtained in the screen. Thus, one of skill in the art can generate derivatives of pYL72 containing the specific Ace3 variant identified and evaluate additional transformants with specific Ace3 variant as described above for the pools.

In the case that transformants with different Ace3 variants show an inducer-independent phenotype intermediate between the pYL72 (Ace3-LC) and pYL88 (Ace3-LC C-term-11) control transformants, where practically possible, the individual mutations of these variants may be combined and similarly evaluated as described above.

Likewise, the optimal amino acid sequences of any Ace3 variants identified from such screened library pools (e.g., from Library 1, Library 2 and/or Library 3) as described above can be combined and further subjected to subsequent rounds focused library screening and evaluated as above. For example, depending on the sample size of transformants screened, some amino acid substitutions for a given position may not be represented in the site substitution library (Library 1). There may be incentive to isolate or generate individual plasmid clones with variants for the most useful positions wherein all possible substitutions can be evaluated individually (e.g., as opposed to the pools initially used for Library 1). Additionally, for useful Ace3 variants identified from the scanning insertion library (Library 2), there may be incentive to test further variants at the most useful positions, for example, by increasing the insert length to six (6), nine (9), or more amino acid residues and/or reducing the insertion to two (2) or one (1) amino acid residue(s). Furthermore, for useful variants identified from the scanning deletion library (Library 3), there may be incentive to generate and test further variants at the most useful positions, for example, by increasing the number of adjacent deleted residues, as practical, to four (4), six (6), eight (8) or the like amino acid residue(s) and/or reducing the deletion size to two (2) or one (1) amino acid residue(s).

Example 4

Ace3 with C-Terminal Substitutions

A. Overview

In the present example, Applicant has molecularly substituted the last eleven (11) amino acid residues of the Ace3-LC (SEQ ID NO: 2) C-terminus with either a V5 epitope tag, or a V5-(6×His) tandem tag (FIG. 12). As described below, *Trichoderma* strains expressing the Ace3-LC with C-terminal V5 tag substitutions (i.e., Ace3-LC-V5) and the Ace3-LC with C-terminal V5-(6×His) tandem tag (i.e., Ace3-LC-V5-(6×His)) substitutions showed increased protein production both in the presence and the absence of an inducing substrate.

B. Host Strain, Expression Vectors and Strain Construction.

*T. reesei* strain T4abc (e.g., described above in Example 2) was used as the parental strain in instant example. The *Trichoderma* ace3 C-terminal substitution cassette plasmids pYL18 (Ace3-LC-V5) and pYL19 (Ace3-LC-V5-(6×His)) were prepared using standard molecular biology procedures, such that one skilled in the art may readily recreate this plasmid from the relevant DNA parts disclosed. More particularly, the DNA sequences for the coding sequences of the Ace3 C-terminal substitution variants starting at the codon corresponding to amino acid residue 641 of SEQ ID NO: 2 are set forth as SEQ ID NO: 67 for Ace3-LC-V5 and SEQ ID NO: 69 for Ace3-LC-V5-(6×His).

The expression vectors comprise a vector backbone with the bacterial ColE1 on and AmpR gene for replication and selection in *E. coli*, and the 2μ on and URA3 gene for replication and selection in *Saccharomyces cerevisiae*. In addition, *T. reesei* telomere sequences ("TrTEL"), *T. reesei* pyr2 selection marker, a *T. reesei* promoter sequence of gene dic1, and the Ace3-LC variant, with its native terminator sequence are present. A representative vector map is shown in FIG. 13, depicting vector pYL18 containing the Ace3-LC variant with the last eleven (11) amino acid substituted with a fourteen (14) amino acid V5 tag sequence.

The expression vectors were inserted (transformed) into a *T. reesei* parental host strain (comprising a non-functional pyr2 gene) by polyethylene glycol (PEG)-mediated protoplast transformation (Ouedraogo et al., 2015; Penttila et al., 1987). The transformants were grown on Vogel's minimal medium agar plates to select for uridine prototrophy acquired by the pyr2 marker. Stable transformants were obtained by transferring on Vogel's agar plate for two successive rounds, followed by two successive rounds of growth on non-selective PDA plates, and one round on Vogel's agar plate, after which single colonies were obtained by plating dilutions of a spore suspension.

C. Fermentation of the Ace3 C-Terminal Substitution Transformants

The parental and transformed (daughter) *T. reesei* host cells described above were tested under both "non-inducing" and "inducing" conditions as described above in Example 1. For example, as presented in FIG. 14, the parental *T. reesei* cells only produced high levels of secreted proteins in the presence of the sophorose inducer. In contrast, the variant (daughter) *T. reesei* cells, comprising and expressing Ace3-L (i.e., comprising the eleven (11) amino acid truncation), produced high amounts of secreted protein, under both inducing (Glu/Sop) and non-inducing (Glu) conditions. In addition, the variant (daughter) *T. reesei* cells comprising and expressing Ace3-LC-V5 tag (i.e., comprising a fourteen (14) amino acid substitution of the last eleven (11) amino acids) and the *T. reesei* cells comprising and expressing Ace3-LC-V5-(6×His) dual tag (i.e., comprising a twenty-three (23) amino acid substitution of the last eleven (11) amino acids) also demonstrated high protein productivities (FIG. 14) under both inducing (Glu/Sop) and non-inducing (Glu) conditions, albeit of approximately 10% lower than the Ace3-L variant.

Based on the foregoing, these results demonstrate that additional genetic modifications of the Ace3 C-terminus including, but not limited to, substitutions, insertions, internal (C-terminal) deletions, and combinations thereof are equally suitable genetic modifications for improving protein productivity in *Trichoderma* sp. cells, under both inducing (Glu/Sop) and non-inducing (Glu) substrate conditions.

REFERENCES

PCT International Publication No. WO1992/06183
PCT International Publication No. WO1992/06209
PCT International Publication No. WO1992/06221
PCT International Publication No. WO1992/10581
PCT International Publication No. WO1998/15619
PCT International Publication No. WO2002/12465
PCT International Publication No. WO2005/028636
PCT International Publication No. WO2006/074005
PCT International Publication No. WO2006/74005
PCT International Publication No. WO2016/100568
U.S. Pat. No. 6,022,725
U.S. Pat. No. 6,268,328
Boel et al., *EMBO J* 3:1581-1585, 1984.
Cao et al., *Science,* 9: 991-1001, 2000.
Campbell et al., *Curr. Genet.,* 16: 53-56, 1989.
Chen et al., "Engineering of *Trichoderma reesei* for enhanced degradation of lignocellulosic biomass by truncation of the cellulase activator ACE3 ", *Biotechnol Biofuels* 13:62, 2020.
Colot et al., *PNAS* 103(27):10352-10357, 2006.
Devereux et al., *Nucleic Acids Res.* 12:387-395, 1984.
Hakkinen, M., Valkonen, M. J., Westerholm-Parvinen, A., Aro, N., Arvas, M., Vitikainen, M., Penttila, M., Salo-heimo, M., and Pakula, T. M., "Screening of candidate regulators for cellulase and hemicellulase production in *Trichoderma reesei* and identification of a factor essential for cellulase production", *Biotechnol Biofuels* 7, 14, 2014.
Harkki et al., *BioTechnol.,* 7: 596-603, 1989.
Harkki et al., *Enzyme Microb. Technol.,* 13: 227-233, 1991.
Ilmen et al., "Regulation of cellulase gene expression in the filamentous fungus *Trichoderma reesei*", *Applied and Environmental Microbiology,* 63(4)-1298-1306, 1997.
Kriegler, Gene Transfer and Expression: A Laboratory Manual, 1990.
Le Crom et al., "Tracking the roots of cellulase hyper-production by the fungus *Trichoderma reesei* using massively parallel DNA sequencing", *PNAS* 106 (38): 16151-16156, 2009.
Mullaney et al., *MGG* 199:37-45, 1985.
Needleman and Wunsch, *J. Mol. Biol.,* 48:443, 1970.
Nunberg et al., *Mol. Cell Biol.* 4:2306, 1984.
Ouedraogo, J. P., Arentshorst, M., Nikolaev, I., Barends, S., and Ram, A. F., "I-Scel-mediated double-strand DNA breaks stimulate efficient gene targeting in the industrial fungus *Trichoderma reesei*" Applied micro-biology and biotechnology 99, 10083-10095, 2015.
Pearson and Lipman, *Proc. Natl. Acad. Sci. USA* 85:2444, 1988.
Penttila, M., Nevalainen, H., Ratto, M., Salminen, E., and Knowles, J., "A versatile transformation system for the cellulolytic filamentous fungus *Trichoderma reesei*", *Gene* 61, 155-164, 1987.
Sambrook et al., Molecular Cloning, *A Laboratory Manual,* 2$^{nd}$ Edition, *Cold Spring Harbor Laboratory Press*, Cold Spring, New York, 1989.
Sambrook et al., *Molecular Cloning, A Laboratory Manual,* 4$^{th}$ Edition, *Cold Spring Harbor Laboratory Press*, Cold Spring, New York, 2012.
Sheir-Neiss and Montenecourt, "Characterization of the secreted cellulases of *Trichoderma reesei* wild type and mutants during controlled fermentations", Applied Microbiology and Biotechnology, 20(1):46-53, 1984.
Smith and Waterman, *Adv. Appl. Math.* 2:482, 1981.
Yelton et al., *PNAS USA* 81:1470-1474, 1984.
Zhang et al., "The transcription factor ACE3 controls cellulase activities and lactose metabolism via two additional regulators in the fungus *Trichoderma reesei*", *J. Biol. Chem.,* 294(48):18435-18450, 2019.

---

The invention claimed is:

1. A method for producing a lignocellulosic degrading enzyme in a genetically modified *Trichoderma* sp. fungal cell comprising:

obtaining a *Trichoderma* sp. fungal cell comprising an ace3 gene encoding a wild-type Ace3 transcription factor (TF) protein comprising at least 90% sequence identity to amino acid positions 1-689 of SEQ ID NO: 2, genetically modifying the ace3 gene of the *Trichoderma* sp. cell, wherein the modified ace3 gene encodes a variant Ace3 TF protein consisting of an amino acid sequence selected from any one of SEQ ID NO: 9 through 18, and fermenting the modified *Trichoderma* sp. cell under suitable conditions for production of a lignocellulosic degrading enzyme, wherein the suitable fermentation conditions do not include an inducing substrate.

2. The method of claim 1, wherein the variant Ace3 TF comprises a functional N-terminal binuclear zinc cluster ($Zn_2Cys_6$) DNA binding domain comprising at least 95% sequence identity to SEQ ID NO: 29.

3. A method for producing a protein of interest (POI) in a modified *Trichoderma* sp. cell comprising:

obtaining a *Trichoderma* sp. fungal cell comprising an ace3 gene encoding a wild-type Ace3 transcription factor (TF) protein comprising at least 90% sequence identity to amino acid positions 1-689 of SEQ ID NO: 2, genetically modifying the ace3 gene of the *Trichoderma* sp. cell, wherein the modified ace3 gene encodes a variant Ace3 TF protein consisting of an amino acid sequence selected from any one of SEQ ID NO: 9 through 18, introducing an expression cassette encoding a POI into the modified *Trichoderma* sp. cell, wherein the expression cassette comprises an upstream promoter sequence derived from a gene encoding lignocellulosic degrading enzyme operably linked to a downstream open reading frame (ORF) sequence encoding a POI, and fermenting the modified *Trichoderma* sp. cell under suitable conditions for production of the POI, wherein the suitable fermentation conditions do not include an inducing substrate.

4. The method of claim 3, wherein the lignocellulosic degrading enzyme is a cellobiohydrolase, an endoglucanase or a xylanase.

5. The method of claim 3, wherein the variant Ace3 TF comprises a functional N-terminal binuclear zinc cluster ($Zn_2Cys_6$) DNA binding domain comprising at least 95% sequence identity to SEQ ID NO: 29.

* * * * *